US005859221A

United States Patent [19]
Cook et al.

[11] Patent Number: 5,859,221
[45] Date of Patent: Jan. 12, 1999

[54] 2'-MODIFIED OLIGONUCLEOTIDES

[75] Inventors: Phillip Dan Cook, San Marcos; Andrew Mamoru Kawasaki, Oceanside, both of Calif.

[73] Assignee: ISIS Pharmaceuticals, Inc., Carlsbad, Calif.

[21] Appl. No.: 468,037

[22] Filed: Jun. 6, 1995

Related U.S. Application Data

[63] Continuation-in-part of Ser. No. 854,634, filed as PCT/US91/00243, Jan. 11, 1991, abandoned, and a continuation-in-part of Ser. No. 835,932, filed as PCT/US91/05720, Aug. 12, 1991, Pat. No. 5,670,633, which is a continuation-in-part of Ser. No. 566,977, Aug. 13, 1990, abandoned, said Ser. No. 854,634, is a continuation-in-part of Ser. No. 463,358, Jan. 11, 1990, abandoned, and Ser. No. 566,977, Aug. 13, 1990, abandoned.

[51] Int. Cl.$^6$ ............... C07H 21/04; C07H 21/00; C12Q 1/68
[52] U.S. Cl. ............ 536/23.1; 536/24.5; 536/25.3; 435/6; 435/91.1; 435/91.3
[58] Field of Search ............ 514/44; 536/23.1, 536/24.5; 435/25.3, 6, 91.1

[56] References Cited

U.S. PATENT DOCUMENTS

| | | | |
|---|---|---|---|
| 4,381,344 | 4/1983 | Rideout et al. | 435/87 |
| 4,511,713 | 4/1985 | Miller et al. | 536/27 |
| 4,689,320 | 8/1987 | Kaji | 514/44 |
| 4,760,017 | 7/1988 | McCormick | 435/6 |
| 4,876,335 | 10/1989 | Yamane et al. | 536/27 |
| 4,965,350 | 10/1990 | Inoue et al. | 536/28 |
| 5,013,830 | 5/1991 | Ohtsuka et al. | 536/27 |
| 5,134,066 | 7/1992 | Rogers et al. | 435/91.3 |
| 5,138,045 | 8/1992 | Cook et al. | 536/27 |
| 5,212,295 | 5/1993 | Cook | 536/26.7 |
| 5,214,135 | 5/1993 | Srivastava et al. | 536/26.7 |
| 5,223,618 | 6/1993 | Cook et al. | 544/276 |
| 5,378,825 | 1/1995 | Cook et al. | 536/25.3 |
| 5,466,786 | 11/1995 | Buhr et al. | 536/26.26 |

FOREIGN PATENT DOCUMENTS

| | | |
|---|---|---|
| 2017369 | 5/1990 | Canada . |
| 0 260 032 A2 | 3/1988 | European Pat. Off. . |
| 0 269 574 A2 | 6/1988 | European Pat. Off. . |
| 0287313 | 10/1988 | European Pat. Off. . |
| 0 339 330 A2 | 11/1989 | European Pat. Off. . |
| 0 339 842 A2 | 11/1989 | European Pat. Off. . |
| 0 399 330 | 5/1990 | European Pat. Off. . |
| 0417999 | 3/1991 | European Pat. Off. . |
| 3915462 A1 | 6/1990 | Germany . |
| 41 10085 A1 | 10/1992 | Germany . |
| WO 90/15814 | 12/1990 | WIPO . |
| WO 91/06556 | 5/1991 | WIPO . |
| WO 91/10671 | 7/1991 | WIPO . |
| WO 91/15499 | 10/1991 | WIPO . |
| WO 92/02258 | 2/1992 | WIPO . |
| WO 92/03568 | 3/1992 | WIPO . |
| WO 92/07065 | 4/1992 | WIPO . |
| WO 92/22651 | 12/1992 | WIPO . |

OTHER PUBLICATIONS

Arnott and Hukins, "Optimised Parameters for A–DNA and B–DNA" *Biochemical and Biophysical Research Comm.*, 1970, 47, 1504–1510.

Beaucage, et al., "Deoxynucleoside phosphoramidites—A new class of key intermediates for deoxypolynucleotide synthesis", *Tetrahedron Letters*, 1981, 22, 1859–1862.

Beaucage, et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Bhat, et al., "A Simple and Convenient Method for the Selective N–Acylations of Cytosine Nucleosides" *Nucleosides & Nucleotides*, 1989, 8, 179–183.

Borer, et al., "Stability of ribonucleic acid double–stranded helices", *J. Mol. Biol.*, 1974, 86, 843–853.

Buhtke, et al., "Facile synthesis of 2'–amino–2–deoxynucleoside from the corresponding arabino derivative", *Nucleic Acid Chemistry*, 1986, Part Three, 149–152.

Chen and Wu, "Studies on Fluroalkylation and Fluroalkoxylation. Part 33. Direct Trifluoromethylation of Aryl Halides with Fluorosulphonyldifluoromethyl Iodide in the Presence of Copper: an Electron Transfer Induced Process" *J. Chem. Soc., Perkin Transactions*, 1989, 1, 2385–2387.

Chladek, et al., "Facile Synthesis of 2'–Amino–2'Deoxyadenosine", *J. Carbohydrates, Nucleosides & Nucleotides*, 1980, 7, 63–75.

Dignam, et al., "Accurate transcription initiation by RNA polymerase II in a soluble extract from isolated mammalian nuclei", *Nucleic Acids Res.*, 1983, 11, 1475–1489.

Eckstein, et al., "Polynucleotides Containing 2'–Chloro–2'–Deoxyribose", *Biochemistry*, 1972,11, 4336–4344.

Fox, et al., "Nucleosides. XVIII. Synthesis of 2'Fluorothymidine, 2'–Fluorodexyuridine, and Other 2'–Halogeno–2'–Deoxy Nucleosides$_{1,2}$", *J. Org. Chem.*, 1964, 29, 558–564.

Freskos, "Synthesis of 2'Deoxypyrimidine Nucleosides Via Copper (I) Iodide Catalysis", *Nucleosides & Nucleotides*, 1989, 8, 1075–1076.

(List continued on next page.)

*Primary Examiner*—John L. LeGuyader
*Assistant Examiner*—Andrew Wang
*Attorney, Agent, or Firm*—Woodcock Washburn Kurtz Mackiewicz & Norris LLP

[57] ABSTRACT

Compositions and methods are provided for the treatment and diagnosis of diseases amenable to modulation of the production of selected proteins. In accordance with preferred embodiments, oligonucleotides and oligonucleotide analogs are provided which are specifically hybridizable with a selected sequence of RNA or DNA wherein at least one of the 2'-deoxyfuranosyl moieties of the nucleoside unit is modified. Treatment of diseases caused by various viruses and other causative agents is provided.

6 Claims, 9 Drawing Sheets

OTHER PUBLICATIONS

Gaffney, et al., "A New Strategy for the Protection of eoxyguanosine During Oligonucleotide Synthesis", *Tetrahedron Letters*, 1982, 23, 2257–2260.

Gait, M.J., Ed., "Oligonucleotide Synthesis. A Practical Approach", Chapter 13, Atkinson and Smith, Authors, IRL Press, 1984.

Graham, et al., "Tritium Labeling of Antisense Oligonucleotides by Exchange with Tritiated Water", *Nucleic Acids. Res.*, 1993, 16, 3737–3743.

Greenberg in *Current Protocols in Molecular Biology*, Ausubel, et al., Eds., John Wiley & Sons, New York.

Guschlbauer, et al., "Nucleoside conformation is Determined by the Electronegativity of the Sugar Substituent", *Nucleic Acids Res.*, 1980, 8, 1421.

Hansske, et al., "2'and 3'–ketonucleosides and their arabino and XYLO reductin products", *Tetrahedron*, 1984, 40, 125–135.

De las Heras, et al., "3'C–Cyano–3'–Deoxythymidine", *Tetrahedron Letters*, 1988, 29, 941–944.

Hertel, et al., "Synthesis of 2–deoxy–2, 2–difluoro–D–ribose and 2–deoxy–2,2–difluoro–D–ribofuranosyl nucleosides", *J. Org. Chem.*, 1988, 53, 2406–2409.

Ikehara, et al., "Studies of Nucleosides and Nucleotides–LXV[1] Purine Cyclonucleosides–26 A Versatile Method for the Synthesis of Purine O–Cyclo–Nucleosides. The First Synthesis of 8,2'–Anhydro–8–Oxy 9–β–D–Arabinofuranosylguanine", *Tetrahedron*, 1975, 31, 1369–1372.

Ikehara, et al., "Studies of Nucleosides and Nucleotides–LXXXIV[1] Purine Cyclonucleosides—34 A New Method for the Synthesis of 2'–substituted 2'–deoxyadenosines", *Tetradedron*, 1978, 34, 1133–1138.

Ikehara, et al., "Purine 8–cyclonucleosides", *Accounts of Chemical Research*, 1969, 2, 47–53.

Ikehara, et al., "Improved Synthesis of 2'–fluoro–2'–deoxyadenosine and Synthesis and Carbon–13 NMR Spectrum of its 3', 5'cyclic Phosphate Derivative", *Nucleosides & Nucleotides*, 1983, 2, 373–385.

Ikehara, et al., "Studies of Nucleosides and Nucleotides–LXXXII.[1] cyclonucleosides. (39).[2] synthesis and properties of 2'halogen–2'–deoxyadenosines", *Chem. Pharm. Bull.*, 1978, 26, 2449–2453.

Ikehara, et al., "A Linear Relationship Between Electronegativity of 2'–Substituents and Conformation of Adenine Nucleosides", *Tetrahedron Letters*, 1979, 42, 4073–4076.

Ikehara, et al., Polynucleotides. LII.synthesis and properties of poly (2'–deox–2'–fluoroadenylic acid), *Nucleic Acids Research*, 1978, 5, 1877–1887.

Ikehara, et al., "Studies of Nucleosides and Nucleotides–LXXXVII.[1], Purine cyclonucleosides. XLII. synthesis of 2'deoxy–2'fluorofunaosine", *Chem. and Pharm. Bull.*, 1981, 29, 1034–1038.

Ikehara, et al., "Purine cyclonucleosides. (43) . synthesis and properties of 2'halogen–2'–deoxyguanosines[1]", *Chem. and Pharm. Bull.*, 1981, 29, 3281–3285.

Ikehara, et al., "Polynucleotides. LVI. Synthesis and Properties of Poly(2'–deoxy–2'–fluoroinosinic Acid)", *Nucleic Acids Res.*, 1978, 5, 3315–3324.

Ikehara, et al., "Polynucleotides. L. synthesis and properties of poly (2'chloro–2'–deoxyadenylic acid) and poly (2'–bromo–2'–deoxyadenylic acid", *Nucleic Acids Res.*, 1978, 4, 4249–4260.

Ikehara, et al., "Recognition by restriction endonuclease EcoR1 of deoxyoctanucleotides containing modified sugar moieties", *European J. Biochem.*, 1984, 139, 447–450.

Imazawa, et al., "Nucleosides and nucleotides. XII.[1] Synthesis and properties of 2'–deoxy–2'–mercaptouridine and its derivates", *Chem. Pharm. Bull.*, 1975, 23, 604–610.

Inoue, et al., "Synthesis and hybridization studies on two complementary nona (2'–O–methyl) ribonucleotides", *Nucleic Acid Res.*, 1987, 15, 6131–6148.

Jones, *Oligonucleotide Synthesis*—A Practical Approach, M.J. Gait, Ed., IRL Press, Washington, D.C. 1985.

Castle, et al., "Imidazo[4, 5–D] pyridazines. I. Synthesis of 4,7–disubstituted derivatives", *Journal of Organic Chemistry*, 1958, 23, 1534–1538.

Jones, et al., "Transient protection: Efficient one–flask synthesis of protected deoxynucleosides", *J. Am. Chem. Soc.*, 1982, 104, 1316–1319.

Jarvi, et al., "Synthesis and biological evaluation of dideoxunucleosides containing a difluoromethylene unit", *Nucleosides & Nucleotides*, 1989, 8, 1111–1114.

Kingston, R.E. et al., "Calcium Phosphate Transfection", *Current Proocols in Molecular Biology* 1990, Supplement 14, 911–919.

Koole, et al., "Synthesis of phosphate–methylated DNA fragments using 9–fluorenylmethoxycarbonyl as transient base protecting group", *J. Org. Chem.*, 1989, 54, 1657–1664.

Jones, et al., "4'–substituted nucleosides. 5. hydroxymethylation of nucleoside 5'–aldehydes",*J. Org. Chem.*, 1979, 44, 1309–1317.

Marcus–Sekura, "Comparative inhibition of chloramphenicol acetyltransferase gene expression by antisense oligonucleotide analogues having alkyl phosphotriester, methylphosphonate and phosphorothioate linkages", *Nucleic Acids Res.*, 1987, 15, 5749–5763.

Markiewicz, et al., "Simultaneous Protection 3'–and 5'–Hydroxyl Groups of Nucleosides", *Nucleic Acid Chemistry*, Part 3, pp. 222–231, L. B. Townsend, et al., Eds., J. Wiley and Sons, New York, 1986.

Miller,et al., "A New Approach to Chemotherapy Based on Molecular Biology and Nucleic Acid Chemistry: Matagen (Masking Tape for Gene Expression" *Anti–Cancer Drug Design*, 1987, 2, 117–128.

Ogilvie, et al., "Solution and solid phase chemical synthesis of arabinonucleotides", *Can J. Chem.*, 1989, 831–839.

Caruthers, M., "Synthesis of Oligonucleotides and Oligonucleotide Analogues", in *Oligonucleotides. Antisense Inhibitors of Gene Expression.*, J.S. Cohen, Ed., CRC Press, Inc., 7–24, (1989).

Owen, et al., "Transcriptional activation of a conserved sequence element by ras requires a nuclear factor distinct from c–fos or c–jun", *Proc. Natl. Acad. Sci USA*, 1990, 87, 3866–3870.

Parkes, et al., "A short synthesis of 3'–cyano–3'–Deoxythymidine", *Tetrahedron Letters*, 1988, 29, 2995–2996.

Petersheim et al., "Base–Stacking and Base–Pairing contributions to helix stability: thermodynamics of double–helix formation with CCGG, CCGGp, CCGGAp, ACCGGp, CCGGUp, and ACCGGUp", *Biochemistry*, 1983, 22, 256–263.

Puglisi, et al., "Absorbance melting curves of RNA", *Methods in Enzymology*, 1989, 180, 304–325.

Ranganathan, "Modification of the $2^1$–Position of Purine Nucleosides: Synthesis of $2^1$–Deoxyadenosine Analogs", *Tetrahedron Letters*, 1977, 15, 1291–1294.

Rao, et al., "A Novel One–step Procedure for the Conversion of Thymidine into 2,3'-Anhydrothymidine", *J. Chem. Soc. Chem. Commun.*, 1989, 997–998.

Reese, et al., "4–(1,2,4–Triazol–l–yl) –and 4–(3–Nitro–1,2,4,–triazol–1–yl)–1–(β–D–2,3,5–tri–O–acetylarabinofuranosyl) pyrimidin–2 (1H)–ones. Valuable Intermediates in the Synthesis of Derivatives of 1–(β–D–Arabinofuranosyl) cytosine (Ara–C)", *J. Chem. Soc. Perkin Trans. I*, 1982, 1171–1176.

Robins, et al., "Nucleic acid related compounds. 41. Restricted furanose conformations of 3', 5'O–(1,1,3,3–tetraisopropyldisilox–1,3–diyl) nucleosides provide a convenient evaluation of anomeric configuration", *Can. J. Chem.*, 1983, 61, 1911–1920.

Robins, et al., "Nucleic Acid Related Compounds. 42. A General Procedure for the Efficient Deoxygenation of Secondary Alcohols. Regiospecific and Stereoselective Conversion of Ribonucleosides to 2'–Deoxynucleosides", *J. Am. Chem. Soc.*, 1983, 105, 4059–4065.

Robins, et al., "Synthesis of 2'–Deoxytubercidin, 2'–Deoxyadenosine, and Related 2'–Deoxynucleosides via a Novel Direct Stereospecific Sodium Salt Glycosylation Procedure", *J. Am. Chem. Soc.*, 1984, 106, 6379–6382.

Sambrook, et al., "Molecular Cloning. A Laboratory Manual", Cold Spring Harbor Laboratory Press, 1989, vol. 2, pp. 11.31–11.32.

Schwartz, et al., "A microtransfection method using the luciferase–encoding reporter gene for the assay of human immunodeficiency virus LTR promoter activity", *Gene*, 1990, 88, 197–205.

Seela, et al., "Palindromic Octa–and Dodecanucleotides Containing 2'–Deoxytubercidin: Synthesis, Hairpin Formation, and Recognition by the Endodeoxyribonuclease", *Biochemistry*, 1987, 26, 2233–2238.

Shibahara, et al., "Inhibition of Human Immunodeficiency Virus (HIV–1) Replication by Synthetic Oligo–RNA Derivatives" *Nucleic Acids Research*, 1987, 17, 239–252.

Sproat, et al., "New synthetic routes to protected purine 2'–O–methylriboside–3'–O–phosphoramidites using a novel alkylation procedure", *Nucleic Acids Research*, 1990, 18, 41–49.

Sproat, et al., "Highly Efficient Chemical Synthesis of 2'–O–methylioligoribunocleotides and Tetrabiotinylated Derivatives; Novel Probes That are Resistant to Degradation by RNA or DNA Specific Nucleases", *Nucleic Acids Research*, 1989, 17, 3373–3386.

Suciu et al., "Synthesis of 9–(2,5–dideoxy–β–D–glycero–pent–4–enofuranosyl) adenine", *Carbohydrate Research*, 1975, 44, 112–115.

Markiewicz, et al., "Simultaneous Protection of 3'–and 5'–Hydroxyl Groups of Nucleosides", *Nucleic Acid Chemistry*, 1986, 229–231.

Stufkens, et al., "Dynamic Jahn–Teller Effect in the Excited States of $SeCl_6^{2-}$, $SeBr_6^{2-}$, and $TeBr_6^{2-}$", *Recueil des Travaux Chimiques des Pays–Bas* 1970, 89, 1185–1201.

Zon, "Oligonucleotide Analogues as Potential Chemotherapy Agents", *Pharm. Res.*, 1988, 5 (9), 539–549.

Stein, et al., "Oligodeoxynucleotides as Inhibitors of Gene Expression: A Review", *Cancer Research*, 1988, 48, 2659–2668.

Walder, et al., "Antisense DNA and RNA: Progress and Prospects", *Genes & Development*, 1988, 2, 502–504.

Marcus–Sekura, "Techniques for Using Antisense Oligodeoxyribonucleotides to Study Gene Expression", *Anal. Biochemistry*, 1988, 172, 289–295.

Zon, "Synthesis of Backbone–Modified DNA Analogues for Biological Applications", *J. Protein Chemistry*, 1987, 6, 131–145.

Van der Krol, et al., "Modulation of Aukaryotic Gene Expression by Complementary RNA or DNA Sequences", *BioTechniques*, 1988, 6, 958–976.

Walder, et al., "Role of RNase H in Hybrid–Arrested Translation by Antisense Oligonucleotides", *Proc. Natl. Acad. Sci. USA* 1988, 85, 5011–5015.

Stein, et al., "Physicochemical properties of phosphorothioate oligodeoxynucleotides", *Nucleic Acids Research*, 1988, 16, 3209–3221.

Agarwal, et al., "Synthesis and Enzymatic Properties of Deoxyribooligonucleotides Containing Methyl and Phenylphosphonate Linkages" *Nucleic Acid Research* 1979, 6, 3009–3024.

Miller, et al., "Nonionic nucleic acid analogues. Synthesis and characterization of dideoxyribonucleoside methylphosphonates", *Biochemistry* 1979, 18, 5134–5143.

Jayaraman, et al., "Selective Inhibition of *Escherichia Coli* Protein Synthesis and Growth by Nonionic Oligonucleotides Complementary to the 3' end of 16S rRNA", *Proc. Natl. Acad. Sci. USA* 1981, 78 (3), 1537–1541.

Miller, et al., "Biochemical and Biological Effects of Nonionic Nucleic Acid Methylphosphonates", *Biochemistry* 1981, 20, 1874–1880.

Miller, et al., "Synthesis and properties of adenine and thymine nucleoside alkyl phosphotriesters, the neutral analogs of dinucleoside monophosphates", *J. Am. Chem. Soc.* 1971, 93, 6657–6664.

Agris, et al., "Inhibition of Vesicular Stomatitis Virus Protein Synthesis and Infection by Sequence–Specific Oligodeoxyribonucleoside Methylphosphonates", *Biochemistry* 1986, 25, 6268–6275.

Smith et al., "Antiviral effect of an oligo (nucleoside methylphosphonate) complementary to the splice junction of herpes simplex virus type 1 immediate early pre–mRNAs 4 and 5", *Proc. Natl. Acad. Sci. USA,* 1986, 83, 2787–2791.

Ruby, et al., "An Early Hierarchic Role of U1 Small Nuclear Ribonucleoprotein in Splicesome Assembly", *Science,* 1988, 242, 1028–1035.

Tidd et al., "Evaluation of N–ras Oncogene Anti–Sense, Sense and Nonsense Sequence Methylphosphonate Oligonucleotide Analogues", *Anti–Cancer Drug Design* 1988, 3, 117–127.

Roelen et al., "Synthesis of Nucleic Acid Methylphos–Phonothioates", *Nucleic Acids Research* 1988, 16 (15), 7633–7645.

Agarwal, et al., "Oligodeoxynucleoside Phosphoramidates and Phosphorothioates as Inhibitors of Human Immunodeficiency Virus" *Proc. Natl. Acad. Sci. USA,* 1988, 85, 7079–7083.

Matsukura, M. et al., "Phosphorothioate Analogs of Oligodeoxynucleotides: Inhibitors of Replication and Cytopathic Effects of Human Immunodeficiency Virus", *Proc. Natl. Acad. Sci. USA,* 1987, 84, 7706–7710.

Brill, et al., "Synthesis of Oligodeoxynucleoside Phosphorodithioates Via Thioamidites", *J. Am. Chem. Soc.* 1989, 111, 2321–2322.

Jäger, A. et al., "Oligonucleotide N–alkylphosphoramidates: Synthesis and binding to polynucleotides", *Biochemistry* 1988, 27, 7237–7246.

Letsinger et al., "Effects of Pendant Groups at Phosphorus on Binding Properties of D–ApA Analogues", *Nucleic Acids Research,* 1986, 14, 3487–3499.

Cazenave, C. et al., "Enzymatic amplification of translation inhibition of rabbit β–globin mRNA mediated by anti–messenger oligodeoxynucleotides covalently linked to intercalating agents", *Nucleic Acids Research,* 1987, 15, 4717–4736.

Constant et al., "Heterodimeric Molecules Including Nucleic Acid Bases and 9–Aminoacridine Spectroscopic Studies, Conformations, and Interactions with DNA", *Biochemistry,* 1988, 27, 3997–4003.

Yeung, et al., "Photoreactives and Thermal Properties of Psoralen Cross–Links", *Biochemistry* 1988, 27, 3204–3210.

Meyer, et al., "Efficient, Specific Cross–Linking and Cleavage of DNA by Stable, Synthetic Complementary Oligodeoxynucleotides", *J. Am. Chem. Soc.* 1989, 11, 8517–8519.

Knorre, et al., "Complementary–Addressed Sequence–Specific) Modification of Nucleic Acids", *Progress in Nucleic Acid Research and Molecular Biology* 1985, 32, 291–321.

Le Doan et al., "Sequence–Targeted Chemical Modifications of Nucleic Acids by Complementary Oligonucleotides Covalently Linked to Porphyrins", *Nucleic Acid Research,* 1987, 15, 8643–8659.

Sigman, "Nuclease Activity of 1,10–Phenanthroline–Copper Ion", *Acc. Chem. Res.,* 1986, 19, 180–186.

Dreyer, et al., "Sequence–specific cleavage of single–stranded DNA: Oligodeoxynucleotide–EDTA–Fe (II)", *Proc. Natl. Acad. Sci. USA,* 1985, 82, 968–972.

Weissberger, A., Ed., "Imidazole and its Derivatives" in The Chemistry of Heterocyclic Compounds, Interscience Publishers, Inc., New York, 1953, 447.

Biggadike, et al., "Short convergent route to homochiral carbocylic 2'–deoxynucleosides and carbocyclic robonucleosides", *J. Chem. Soc. Chem. Commun.* 1987, 1083–1984.

Outten, et al., "Synthetic 1–methoxybenzo [d] naphtho [1,2–b]pyran–6–one c–glycosides", *J. Org. Chem.* 1987, 52, 5064–5066.

Revankar et al., "Synthesis and Antiviral/Antitumor of Certain 3–Seazaguanine Nucleosides and Nucleotides", *J. Med. Chem.* 1984, 24, 1389–1396.

Uhlmann, et al., "Antisense Oligonucleotides. A New Therapeutic Principle", *Chemical Reviews,* 1990, 90(4), 534–584.

Divakar, et al., "Approaches to the Synthesis of 2'–Thio Analogues of Pyrimidine Ribosides", *J. Chem. Soc., Perkins Trans., I,* 1990, 969–974.

Divakar, et al., "Reaction Between 2,2'–Anhydro–1–β–D–arrabinofuranosyluracil and Thiolate Ions", *J. Chem. Soc., Perkins Trans. I,* 1982, 1625–1628.

Ryan, et al., "Synthesis of 2–Thio–D–ribose and 2'–Thioadenosine Derivatives", *J. Org. Chem.,* 1971, 36 (18), 2646–2657.

Stull et al., Antigene, ribozyme, and aptamer nucleic acid drugs: progress and prospects, Pharmaceutical Research, v. 12(4), pp. 465–483, 1995.

Christofferson et al., Ribozymes as human therapeutic agents, Journal of Medicinal Chemistry, v. 38(12), pp. 2023–2037, 1995.

San et al., Safety and short term toxicity of a novel cationic lipid formulation for human gene therapy, Human Gene Therapy, v. 4, pp. 781–788, 1993.

Monia et al., Evaluation of 2' modified oligonucleotides containing 2' deoxy gaps as antisense inhibitors of gene expression, Journal of Biological Chemistry, vol. 268(19), pp. 14514–14522, May 1993.

Kawasaki et al., Uniformly modified 2'–deoxy–2'–fluoro phosphorothioate oligonucleotides as nucleasse resistant antisense compounds with high affinity and specificity for RNA targets, Journal of Medicinal Chemistry, vol. 36, pp. 831–841, 1993.

Inoue et al., Sequence dependent hydrolysis of RNA using modified oligonucleotide splints and RNase H, FEBS Letters, vol. 215(2), pp. 327–330, May 1987.

Khurshid et al., *FEBS Letters* 1972, 28:1,25.

Kielanowska et al., *Nucleic Acids Research* 1976, 3:3,817.

Kusmierek et al., *ACTA Biochimica Polonica* 1973, 20:4, 365.

Pike et al., *J. Org. Chem.* 1974, 39:25, 3674.

Ransford et al., *J. Carbohydrates—Nucleosides—Nucleotides* 1974, 1:3,275.

Rottman et al., *Biochemistry* 1974, 13, 2762.

Singer et al., *Biochemistry* 1976, 15:23,5052.

Tazawa et al., *Biochemistry* 1972, 11, 4931.

2'-MODIFIED OLIGONUCLEOTIDES

This application is a continuation-in-part of U.S. patent application Ser. No. 07/835,932 (now U.S. Pat. No. 5,670,633), filed Mar. 5, 1992 which is the U.S. national phase application of International application PCT/US91/05720, filed Aug. 12, 1991 (now abandoned), which is a continuation-in-part of U.S. patent application Ser. No. 07/566,977, filed Aug. 13, 1990 (now abandoned). This application is also a continuation-in-part of U.S. patent application Ser. No. 07/854,634 (now abandoned), filed Jul. 1, 1992 which is the U.S. national phase application of International application PCT/US91/00243, filed Jan. 11, 1991 (now abandoned), which is a continuation-in-part of U.S. patent application Ser. No. 07/463,358, filed Jan. 11, 1990 (now abandoned), and U.S. patent application Ser. No. 07/566,977, filed Aug. 13, 1990 (now abandoned).

FIELD OF THE INVENTION

This invention is directed to nuclease resistant oligonucleotides which are useful as therapeutics, diagnostics, and research reagents. Sugar-modified oligonucleotides which are resistant to nuclease degradation and are capable of modulating the activity of DNA and RNA are provided.

BACKGROUND OF THE INVENTION

It has been recognized that oligonucleotides can be used to modulate mRNA expression by a mechanism that involves the complementary hybridization of relatively short oligonucleotides to mRNA such that the normal, essential functions of these intracellular nucleic acids are disrupted. Hybridization is the sequence-specific base pair hydrogen bonding of an oligonucleotide to a complementary RNA or DNA.

One deficiency of oligonucleotides for these purposes is their susceptibility to enzymatic degradation by a variety of ubiquitous nucleases which may be intracellularly and extracellularly located. Unmodified, "wild type", oligonucleotides are not useful as therapeutic agents because they are rapidly degraded by nucleases. Therefore, modification of oligonucleotides for conferring nuclease resistance on them has been a focus of research directed towards the development of oligonucleotide therapeutics and diagnostics.

In addition to nuclease stability, the ability of an oligonucleotide to bind to a specific DNA or RNA with fidelity is a further important factor.

The relative ability of an oligonucleotide to bind to complementary nucleic acids is compared by determining the melting temperature of a particular hybridization complex. The melting temperature ($T_m$), a characteristic physical property of double helices, is the temperature (in 0° C.) at which 50% helical versus coil (unhybridized) forms are present. $T_m$ is measured by using UV spectroscopy to determine the formation and breakdown (melting) of hybridization. Base stacking, which occurs during hybridization, is accompanied by a reduction in UV absorption (hypochromicity). Consequently, a reduction in UV absorption indicates a higher $T_m$. The higher the $T_m$, the greater the strength of the binding of the nucleic acid strands.

Therefore, oligonucleotides modified to exhibit resistance to nucleases and to hybridize with appropriate strength and fidelity to its targeted RNA (or DNA) are greatly desired for use as research reagents, diagnostic agents and as oligonucleotide therapeutics. Various 2'-substitutions have been introduced in the sugar moiety of oligonucleotides. The nuclease resistance of these compounds has been increased by the introduction of 2'-substituents such as halo, alkoxy and allyloxy groups.

Ikehara et al. [*European Journal of Biochemistry* 139, 447 (1984)] have reported the synthesis of a mixed octamer containing one 2'-deoxy-2'-fluoroguanosine residue or one 2'-deoxy-2'-fluoroadenine residue. Guschlbauer and Jankowski [*Nucleic Acids Res.* 8, 1421 (1980)] have shown that the contribution of the 3'-endo increases with increasing electronegativity of the 2'-substituent. Thus, 2'-deoxy-2'-fluorouridine contains 85% of the C3'-endo conformer.

Furthermore, evidence has been presented which indicates that 2'-substituted-2'-deoxyadenosine polynucleotides resemble double-stranded RNA rather than DNA. Ikehara et al. [*Nucleic Acids Res.*, 5, 3315 (1978)] have shown that a 2'-fluoro substituent in poly A, poly I, or poly C duplexed to its complement is significantly more stable than the ribonucleotide or deoxyribonucleotide poly duplex as determined by standard melting assays. Ikehara et al. [*Nucleic Acids Res.*, 4, 4249 (1978)] have shown that a 2'-chloro or bromo substituent in poly(2'-deoxyadenylic acid) provides nuclease resistance. Eckstein et al. [*Biochemistry*, 11, 4336 (1972)] have reported that poly(2'-chloro-2'-deoxyuridylic acid) and poly(2'-chloro-2'-deoxycytidylic acid) are resistant to various nucleases. Inoue et al. [*Nucleic Acids Research*, 15, 6131 (1987)] have described the synthesis of mixed oligonucleotide sequences containing 2'-OMe substituents on every nucleotide. The mixed 2'-OMe-substituted oligonucleotide hybridized to its RNA complement as strongly as the RNA—RNA duplex which is significantly stronger than the same sequence RNA-DNA heteroduplex ($T_m$s, 49.0 and 50.1 versus 33.0 degrees for nonamers). Shibahara et al. [*Nucleic Acids Research*, 17, 239 (1987)] have reported the synthesis of mixed oligonucleotides containing 2'-OMe substituents on every nucleotide. The mixed 2'-OMe-substituted oligonucleotides were designed to inhibit HIV replication.

It is believed that the composite of the hydroxyl group's steric effect, its hydrogen bonding capabilities, and its electronegativity versus the properties of the hydrogen atom is responsible for the gross structural difference between RNA and DNA. Thermal melting studies indicate that the order of duplex stability (hybridization) of 2'-methoxy oligonucleotides is in the order of RNA—RNA>RNA-DNA>DNA—DNA.

U.S. Pat. No. 5,013,830, issued May 7, 1991, discloses mixed oligonucleotides comprising an RNA portion, bearing 2'-O-alkyl substituents, conjugated to a DNA portion via a phosphodiester linkage. However, being phosphodiesters, these oligonucleotides are susceptible to nuclease cleavage.

European Patent application 339,842, filed Apr. 13, 1989, discloses 2'-O-substituted phosphorothioate oligonucleotides, including 2'-O-methylribooligonucleotide phosphorothioate derivatives. This application also discloses 2'-O-methyl phosphodiester oligonucleotides which lack nuclease resistance.

European Patent application 260,032, filed Aug. 27, 1987, discloses oligonucleotides having 2'-O-methyl substituents on the sugar moiety. This application also makes mention of other 2'-O-alkyl substituents, such as ethyl, propyl and butyl groups.

International Publication Number WO 91/06556, published May 16, 1991, discloses oligomers derivatized at the 2' position with substituents, which are stable to nuclease activity. Specific 2'-O-substituents which were incorporated into oligonucleotides include ethoxycarbonylmethyl (ester form), and its acid, amide and substituted amide forms.

European Patent application 399,330, filed May 15, 1990, discloses nucleotides having 2'-O-alkyl substituents.

International Publication Number WO 91/15499, published Oct. 17, 1991, discloses oligonucleotides bearing 2'-O-alkyl, -alkenyl and -alkynyl substituents.

It has been recognized that nuclease resistance of oligonucleotides and fidelity of hybridization are of great importance in the development of oligonucleotide therapeutics. Oligonucleotides possessing nuclease resistance are also desired as research reagents and diagnostic agents.

BRIEF DESCRIPTION OF THE INVENTION

In accordance with the present invention, compositions which are resistant to nuclease degradation and those that modulate the activity of DNA and RNA are provided. These compositions are comprised of sugar-modified oligonucleotides, which are specifically hybridizable with preselected nucleotide sequences of single-stranded or double-stranded target DNA or RNA. The sugar-modified oligonucleotides recognize and form double strands with single-stranded DNA and RNA.

The nuclease resistant oligonucleotides of the present invention consist of a single strand of nucleic acid bases linked together through linking groups. The oligonucleotides of this invention may range in length from about 5 to about 50 nucleic acid bases. However, in accordance with a preferred embodiment of this invention, a sequence of about 12 to 25 bases in length is optimal.

The individual nucleotides of the oligonucleotides of the present invention are connected via phosphorus linkages. Preferred phosphorous linkages include phosphodiester, phosphorothioate and phosphorodithioate linkages, with phosphodiester and phosphorothioate linkages being particularly preferred.

Preferred nucleobases of the invention include adenine, guanine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine.

In accordance with this invention at least one of the 2'-deoxyribofuranosyl moiety of at least one of the nucleosides of an oligonucleotide is modified. A halo, alkoxy, aminoalkoxy, alkyl, azido, or amino group may be added. For example, F, CN, $CF_3$, $OCF_3$, OCN, O-alkyl, S-alkyl, SMe, $SO_2Me$, $ONO_2$, $NO_{21}$ $NH_3$, $NH_2$, NH-alkyl, $OCH_2CH=CH_2$ (allyloxy), $OCH_3=CH_2$, OCCH, where alkyl is a straight or branched chain of $C_1$ to $C_{20}$, with unsaturation within the carbon chain.

The present invention also includes oligonucleotides formed from a plurality of linked-β-nucleosides including 2'-deoxy-erythro-pentofuranosyl-β-nucleosides. These nucleosides are connected by charged phosphorus linkages in a sequence that is specifically hybridizable with a complementary target nucleic acid. The sequence of linked nucleosides is divided into at least two subsequences. The first subsequence includes β-nucleosides, having 2'-substituents, linked by charged 3'-5' phosphorous linkages. The second subsequence consists of 2'-deoxy-erythro-pentofuranosyl-β-nucleosides linked by charged 3'-5' phosphorous linkages bearing a negative charge at physiological pH. In further preferred embodiments there exists a third subsequence whose nucleosides are selected from those selectable for the first subsequence. In preferred embodiments the second subsequence is positioned between the first and third subsequences. Such oligonucleotides of the present invention are also referred to as "chimeric" or "gapped" oligonucleotides, or "chimeras."

The resulting novel oligonucleotides of the invention are resistant to nuclease degradation and exhibit hybridization properties of higher quality relative to wild-type DNA—DNA and RNA-DNA duplexes and phosphorus-modified oligonucleotide duplexes containing methylphosphonates, phophoramidates and phosphate triesters.

The invention is also directed to methods for modulating the production of a protein by an organism comprising contacting the organism with a composition formulated in accordance with the foregoing considerations. It is preferred that the RNA or DNA portion which is to be modulated be preselected to comprise that portion of DNA or RNA which codes for the protein whose formation is to be modulated. Therefore, the oligonucleotide to be employed is designed to be specifically hybridizable to the preselected portion of target DNA or RNA.

This invention is also directed to methods of treating an organism having a disease characterized by the undesired production of a protein. This method comprises contacting the organism with a composition in accordance with the foregoing considerations. The composition is preferably one which is designed to specifically bind with mRNA which codes for the protein whose production is to be inhibited.

The invention further is directed to diagnostic methods for detecting the presence or absence of abnormal RNA molecules, or abnormal or inappropriate expression of normal RNA molecules in organisms or cells.

The invention is also directed to methods for the selective binding of RNA for use as research reagents and diagnostic agents. Such selective and strong binding is accomplished by interacting such RNA or DNA with oligonucleotides of the invention which are resistant to degradative nucleases and which display greater fidelity of hybridization than any other known oligonucleotide.

DETAILED DESCRIPTION OF PREFERRED EMBODIMENTS

Figure 1:
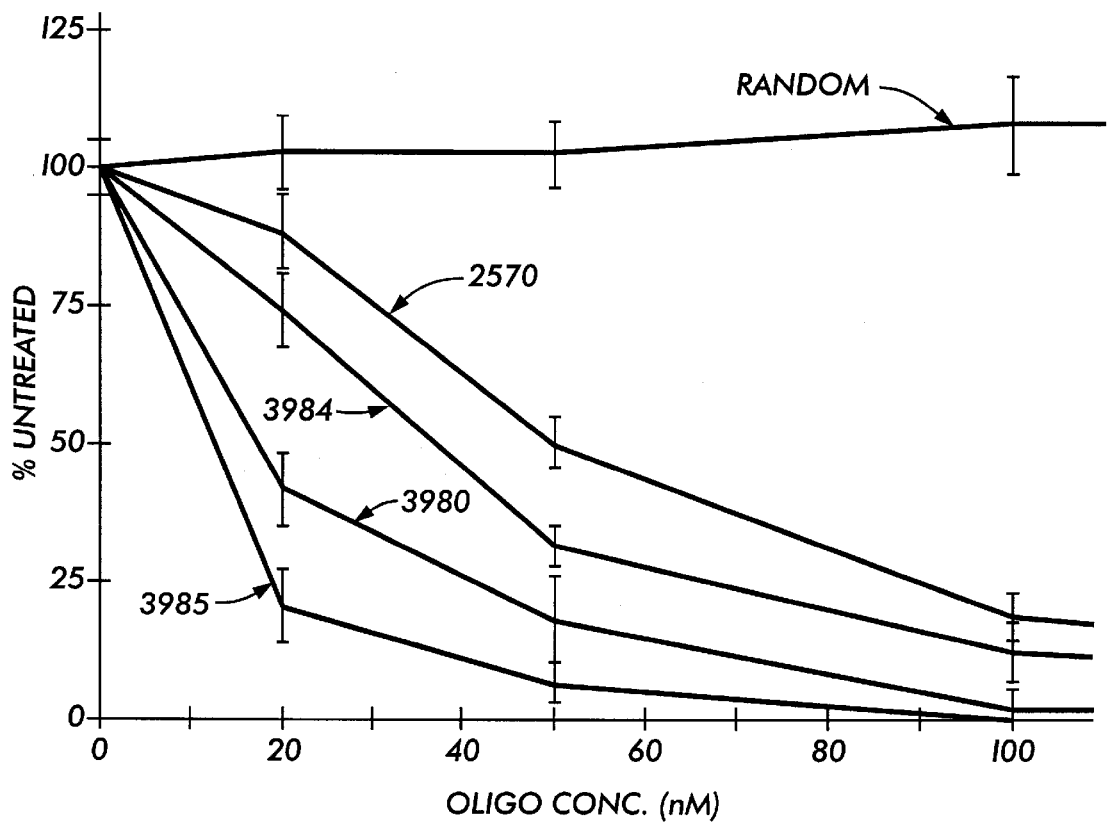
FIG. 1 is a graph showing dose response activity of oligonucleotides of the invention and a reference compound.

The compositions useful for modulating the activity of an RNA or DNA molecule in accordance with this invention generally comprise a sugar-modified oligonucleotide which is specifically hybridizable with a preselected nucleotide sequence of a single-stranded or double-stranded target DNA or RNA molecule, and which is nuclease resistant.

It is generally desirable to select a sequence of DNA or RNA which is involved in the production of a protein whose synthesis is ultimately to be modulated or inhibited in its entirety. The oligonucleotides of the invention are conveniently synthesized using solid phase synthesis of known methodology, and is designed to be complementary to or specifically hybridizable with the preselected nucleotide sequence of the target RNA or DNA. Nucleic acid synthesizers are commercially available and their use is understood by persons of ordinary skill in the art as being effective in generating any desired oligonucleotide of reasonable length.

The oligonucleotides of the invention also include those that comprise nucleosides connected by charged linkages, and whose sequences are divided into at least two subsequences. The first subsequence includes 2'-substituted-nucleosides linked by a first type of linkage. The second subsequence includes nucleosides linked by a second type of linkage. In a preferred embodiment there exists a third subsequence whose nucleosides are selected from those selectable for the first subsequence, and the second subsequence is positioned between the first and the third subsequences. Such oligonucleotides of the invention are known as "chimeras," or "chimeric" or "gapped" oligonucleotides.

In the context of this invention, the term "oligonucleotide" refers to a plurality of nucleotides joined together in a specific! sequence from naturally and non-naturally occurring nucleobases. Preferred nucleobases of the invention are joined through a sugar moiety via phosphorus linkages, and include adenine, guanine, adenine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine. The sugar moiety may be deoxyribose or ribose. The oligonucleotides of the invention may also comprise modified nucleobases or nucleobases having other modifications consistent with the spirit of this invention, and in particular modifications that increase their nuclease resistance in order to facilitate their use as therapeutic, diagnostic or research reagents.

The oligonucleotides of the present invention are about 5 to about 50 bases in length. It is more preferred that the oligonucleotides of the invention have from 8 to about 40 bases, and even more preferred that from about 12 to about 25 bases be employed.

It is desired that the oligonucleotides of the invention be adapted to be specifically hybridizable with the nucleotide sequence of the target RNA or DNA selected for modulation. Oligonucleotides particularly suited for the practice of one or more embodiments of the present invention comprise 2'-sugar modified oligonucleotides wherein one or more of the 2'-deoxy ribofuranosyl moieties of the nucleoside is modified with a halo, alkoxy, aminoalkoxy, alkyl, azido, or amino group. For example, the substitutions which may occur include F, CN, $CF_3$, $OCF_3$, OCN, O-alkyl, S-alkyl, SMe, $SO_2Me$, $ONO_2$, $NO_2$, $NH_3$, $NH_2$, NH-alkyl, $OCH=CH_2$ and OCCH. In each of these, alkyl is a straight or branched chain of $C_1$ to $C_{20}$, having unsaturation within the carbon chain. A preferred alkyl group is $C_1$–$C_9$ alkyl. A further preferred alkyl group is $C_5$–$C_{20}$ alkyl.

A first preferred group of substituents include 2'-deoxy-2'-fluoro substituents. A further preferred group of substituents include $C_1$–$C_{20}$ alkoxyl substituents. An additional preferred group of substituents include cyano, fluoromethyl, thioalkoxyl, fluoroalkoxyl, alkylsulfinyl, alkylsulfonyl, allyloxy and alkeneoxy substituents.

In further embodiments of the present invention, the individual nucleotides of the oligonucleotides of the invention are connected via phosphorus linkages. Preferred phosphorus linkages include phosphodiester, phosphorothioate and phosphorodithioate linkages. In one preferred embodiment of this invention, nuclease resistance is conferred on the oligonucleotides by utilizing phosphorothioate internucleoside linkages.

In further embodiments of the invention, nucleosides can be joined via linkages that substitute for the internucleoside phosphate linkage. Macromolecules of this type have been identified as oligonucleosides. The term "oligonucleoside" thus refers to a plurality of nucleoside units joined by non-phosphorus linkages. In such oligonucleosides the linkages include an —O—$CH_2$—$CH_2$—O— linkage (i.e., an ethylene glycol linkage) as well as other novel linkages disclosed in U.S. Pat. No. 5,223,618, issued Jun. 29, 1993, U.S. Pat. No. 5,378,825, issued Jan. 3, 1995 and U.S. patent application Ser. No. 08/395,168, filed Feb. 27, 1995. Other modifications can be made to the sugar, to the base, or to the phosphate group of the nucleotide. Representative modifications are disclosed in International Publication Numbers WO 91/10671, published Jul. 25, 1991, WO 92/02258, published Feb. 20, 1992, WO 92/03568, published Mar. 5, 1992, and U.S. Pat. No. 5,138,045, issued Aug. 11, 1992, all assigned to the assignee of this application. The disclosures of each of the above referenced publications are herein incorporated by reference.

In the context of this invention, "hybridization" shall mean hydrogen bonding, which may be Watson-Crick, Hoogsteen or reversed Hoogsteen hydrogen bonding, between complementary nucleobases. For example, adenine and thymine are complementary nucleobases which pair through the formation of hydrogen bonds. "Complementary," as used herein, also refers to sequence compl.ementarity between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity such that stable and specific binding occurs between the oligonucleotide and the DNA or RNA target. It is understood that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, i.e. under physiological conditions in the case of in vivo assays or therapeutic treatment, or in the case of in vitro assays, under conditions in which the assays are performed.

Cleavage of oligonucleotides by nucleolytic enzymes require the formation of an enzyme-substrate complex, or in particular a nuclease-oligonucleotide complex. The nuclease enzymes will generally require specific binding sites located on the oligonucleotides for appropriate attachment. If the oligonucleotide binding sites are removed or blocked, such that nucleases are unable to attach to the oligonucleotides, the oligonucleotides will be nuclease resistant. In the case of restriction endonucleases that cleave sequence-specific palindromic double-stranded DNA, certain binding sites such as the ring nitrogen in the 3- and 7-positions have been identified as required binding sites. Removal of one or more of these sites or sterically blocking approach of the nuclease to these particular positions within the oligonucleotide has provided various levels of resistance to specific nucleases.

This invention provides oligonucleotides possessing superior hybridization properties. Structure-activity relationship studies have revealed that an increase in binding ($T_m$) of certain 2'-sugar modified oligonucleotides to an RNA target (complement) correlates with an increased "A" type conformation of the heteroduplex. Furthermore, absolute fidelity of the modified oligonucleotides is maintained. Increased binding of 2'-sugar modified sequence-specific oligonucleotides of the invention provides superior potency and specificity compared to phosphorus-modified oligonucleotides such as methyl phosphonates, phosphate triesters and phosphoramidates as known in the literature.

The only structural difference between DNA and RNA duplexes is a hydrogen atom at the 2'-position of the sugar moiety of a DNA molecule versus a hydroxyl group at the 2'-position of the sugar moiety of an RNA molecule (assuming that the presence or absence of a methyl group in the uracil ring system has no effect). However, gross conformational differences exist between DNA and RNA duplexes.

It is known from X-ray diffraction analysis of nucleic acid fibers [Arnott and Hukins, *Biochemical and Biophysical Research Communication*, 47, 1504–1510 (1970)] and analysis of crystals of double-stranded nucleic acids that DNA takes a "B" form structure and RNA takes the more rigid "A" form structure. The difference between the sugar puckering (C2' endo for "B" form DNA and C3' endo for "A" form RNA) of the nucleosides of DNA and RNA is the major conformational difference between double-stranded nucleic acids.

The primary contributor to the conformation of the pentofuranosyl moiety is the nature of the substituent at the 2'-position. Thus, the population of the C3'-endo form increases with respect to the C2'-endo form as the electronegativity of the 2'-substituent increases. For example, among 2'-deoxy-2'-haloadenosines, the 2'-fluoro derivative exhibits the largest population (65%) of the C3'-endo form, and the 2'-iodo exhibits the lowest population (7%). Those of adenosine (2'-OH) and deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoroadenosine) is further correlated to the stabilization of the stacked conformation. Research indicates that dinucleoside phosphates have a stacked conformation with a geometry similar to that of A—A but with a greater extent of base—base overlapping than A—A. It is assumed that the highly polar nature of the C2'-F bond and the extreme preference for C3'-endo puckering may stabilize the stacked conformation in an "A" structure.

Data from UV hypochromicity, circular dichromism, and $^1$H NMR also indicate that the degree of stacking decreases as the electronegativity of the halo substituent decreases. Furthermore, steric bulk at the 2'-position of the sugar moiety is better accommodated in an "A" form duplex than a "B" form duplex.

Thus, a 2'-substituent on the 3'-nucleotidyl unit of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent.

The 2'-iodo substituted nucleosides possess the lowest C3'-endo population (7%) of the halogen series. Thus, based solely on steric effects, one would predict that a 2'-iodo (or other similar group) would contribute stacking destabilization properties, and thus reduced binding ($T_m$) of the oligonucleotides. However, the lower electronegativity and high hydrophobicity of the iodine atom (or another similar group) complicates the ability to predict stacking stabilities and binding strengths.

Studies with a 2'-OMe modification of 2'-deoxy guanosine, cytidine, and uridine dinucleoside phosphates exhibit enhanced stacking effects with respect to the corresponding unmethylated species (2'-OH). In this case, the hydrophobic attractive forces of the methyl group tend to overcome the destablilizing effects of its steric bulk.

2'-Fluoro-2'-deoxyadenosine has been determined to have an unusually high population of 3'-endo puckered form among nucleosides. Adenosine, 2'-deoxyadenosine and other derivatives have less than 40% of their population in the 3'-endo conformation. It is known that a nucleoside residue in well-stacked oligonucleotides favors 3'-endo ribofuranose puckering.

Melting temperatures (complementary binding) are increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

Compounds of the invention can be utilized as diagnostics, therapeutics and as research reagents and kits. They can be utilized in pharmaceutical compositions by adding an effective amount of an oligonucleotide of the invention to a suitable pharmaceutically acceptable diluent or carrier. They further can be used for treating organisms having a disease characterized by the undesired production of a protein. The organism can be contacted with an oligonucleotide of the invention having a sequence that is capable of specifically hybridizing with a strand of target nucleic acid that codes for the undesirable protein.

The formulation of therapeutic compositions and their subsequent administration is believed to be within the skill of those in the art. In general, for therapeutics, a patient in need of such therapy is administered an oligomer in accordance with the invention, commonly in a pharmaceutically acceptable carrier, in doses ranging from 0.01 µg to 100 g per kg of body weight depending on the age of the patient and the severity of the disease state being treated. Further, the treatment may be a single dose or may be a regimen that may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the oligomer may either be increased in the event the patient does not respond significantly to current dosage levels, or the dose may be decreased if an alleviation of the symptoms of the disease state is observed, or if the disease state has been ablated.

In some cases it may be more effective to treat a patient with an oligomer of the invention in conjunction with other traditional therapeutic modalities. For example, a patient being treated for AIDS may be administered an oligomer in conjunction with AZT, or a patient with atherosclerosis may be treated with an oligomer of the invention following angioplasty to prevent reocclusion of the treated arteries.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to several years.

Following successful treatment, it may be desirable to have the patient undergo maintenance therapy to prevent the recurrence of the disease state, wherein the oligomer is administered in maintenance doses, ranging from 0.01 µg to 100 g per kg of body weight, once or more daily, to once every several years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

The present invention can be practiced in a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular machinery is susceptible to such therapeutic and/or prophylactic treatment. Seemingly diverse organisms such as bacteria, yeast, protozoa, algae, plant and higher animal forms, including warm-blooded animals, can be treated in this manner. Further, since each of the cells of multicellular eukaryotes also includes both DNA-RNA transcription and RNA-protein translation as an integral part of their cellular activity, such therapeutics and/or diagnostics can also be practiced on such cellular populations. Furthermore, many of the organelles, e.g. mitochondria and chloroplasts, of eukaryotic cells also include transcription and translation mechanisms. As such, single cells, cellular populations or organelles also can be included within the definition of organisms that are capable of being treated with the therapeutic or diagnostic oligonucleotides of the invention. As used herein, therapeutics is meant to include both the eradication of a disease state, killing of an organism, e.g. bacterial, protozoan or other infection, or control of aberrant or undesirable cellular growth or expression.

The present novel approach to obtaining stronger binding is to prepare RNA mimics that bind to target RNA. Therefore, a random structure-activity relationship approach was undertaken to discover nuclease resistant oligonucleotides that maintain appropriate hybridization properties.

A series of 2'-deoxy-2'-modified nucleosides of adenine, guanine, cytosine, thymidine and certain analogs of these nucleobases have been prepared and incorporated into oligonucleotides via solid phase nucleic acid synthesis. These novel oligonucleotides were assayed for their hybridization properties and their ability to resist degradation by nucleases compared to the unmodified oligonucleotides. Initially, small electronegative atoms or groups were selected because they would not be expected to sterically interfere with required Watson-Crick base pair hydrogen bonding (hybridization). However, electronic changes due to the electronegativity of the atom or group in the 2'-position may profoundly affect the sugar conformation. Structure-activity relationship studies revealed that the sugar-modified oligonucleotides hybridized to the target RNA more strongly than the unmodified 2'-deoxy oligonucleotides.

2'-Substituted oligonucleotides were synthesized by standard solid phase nucleic acid synthesis using an automated synthesizer such as Model 380B (Perkin-Elmer/Applied Biosystems) or MilliGen/Biosearch 7500 or 8800. Triester, phosphoramidite, or hydrogen phosphonate coupling chemistries [*Oligonucleotides. Antisense Inhibitors of Gene Expression*. M. Caruthers, p. 7, J. S. Cohen (Ed.), C R C Press, Boca Raton, Fla., 1989] are used with these synthesizers to provide the desired oligonucleotides. The Beaucage reagent [*J. Amer. Chem. Soc.*, 112, 1253 (1990)] or elemental sulfur [Beaucage et al., *Tet. Lett.*, 22, 1859 (1981)] is used with phosphoramidite or hydrogen phosphonate chemistries to provide 2'-substituted phosphorothioate oligonucleotides.

The requisite 2'-substituted nucleosides (A, G, C, T(U), and other modified nucleobases) were prepared by modification of several literature procedures as described below.

Procedure 1. Nucleophilic Displacement of 2'-Leaving Group in Arabino Purine Nucleosides. Nucleophilic displacement of a leaving group in the 2'-up position (2'-deoxy-2'-(leaving group)arabino sugar) of adenine or guanine or their analog nucleosides. General synthetic procedures of this type have been described by Ikehara et al., *Tetrahedron*, 34, 1133 (1978); ibid., 31, 1369 (1975); *Chemistry and Pharmaceutical Bulletin*, 26, 2449 (1978); ibid., 26, 240 (1978); Ikehara, *Accounts of Chemical Research*, 2, 47 (1969); and Ranganathan, *Tetrahedron Letters*, 15, 1291 (1977).

Procedure 2. Nucleophilic Displacement of 2,2'-Anhydro Pyrimidines. Nucleosides thymine, uracil, cytosine or their analogs are converted to 2'-substituted nucleosides by the intermediacy of 2,2'-cycloanhydro nucleoside as described by Fox et al., *Journal of Organic Chemistry*, 29, 558 (1964).

Procedure 3. 2'-Coupling Reactions. Appropriately 3',5'-sugar and base protected purine and pyrimidine nucleosides having a unprotected 2'-hydroxyl group are coupled with electrophilic reagents such as methyl iodide and diazomethane to provide the mixed sequences containing a 2'-OMe group H. Inoue et al., *Nucleic Acids Research*, 15, 6131.

Procedure 4. 2-Deoxy-2-substituted Ribosylations. 2-Substituted-2-deoxyribosylation of the appropriately protected nucleic acid bases and nucleic acids base analogs has been reported by Jarvi et al., *Nucleosides & Nucleotides*, 8, 1111–1114 (1989) and Hertel et al., *Journal of Organic Chemistry*, 53, 2406 (1988).

Procedure 5. Enzymatic Synthesis of 2'-Deoxy-2'-Substituted Nucleosides. The 2-Deoxy-2-substituted glycosyl transfer from one nucleoside to another with the aid of pyrimidine and purine ribo or deoxyribo phosphorolyses has been described by Rideout and Krenitsky, U.S. Pat. No. 4,381,344 (1983).

Procedure 6. Conversion of 2'-Substituents Into New Substituents. 2'-Substituted-2'-deoxynucleosides are converted into new substituents via standard chemical manipulations. For example, Chladek et al. [*Journal of Carbohydrates, Nucleosides & Nucleotides*, 7, 63 (1980)] describes the conversion of 2'-deoxy-2'-azidoadenosine, prepared from arabinofuranosyladenine, into 2'-deoxy-2'-aminoadenosine.

Procedure 7. Free Radical Reactions. Conversions of halogen substituted nucleosides into 2'-deoxy-2'-substituted nucleosides via free radical reactions has been described by Parkes and Taylor [*Tetrahedron Letters*, 29, 2995 (1988)].

Procedure 8. Conversion of Ribonucleosides to 2'-Deoxy-2'-Substituted Nucleoside. Appropriately 3',5'-sugar and base protected purine and pyrimidine nucleosides having a unprotected 2'-hydroxyl group are converted to 2'-deoxy-2'-substituted nucleosides by the process of oxidation to the 2'-keto group, reaction with nucleophilic reagents, and finally 2'-deoxygenation. Procedures of this type have been described by De las Heras, et al. [*Tetrahedron Letters*, 29, 941 (1988)].

Procedure 9. In one process of the invention, 2'-deoxy substituted guanosine compounds are prepared via an (arabinofuranosyl)guanine intermediate obtained via an oxidation-reduction reaction. A leaving group at the 2' position of the arabinofuranosyl sugar moiety of the intermediate arabino compound is displaced via an $SN_2$ reaction with an appropriate nucleophile. This procedure thus incorporates principles of both Procedure 1 and Procedure 8 above. 2'-Deoxy-2'-fluoroguanosine is preferably prepared via this procedure. The intermediate arabino compound was obtained utilizing a variation of the oxidation-reduction procedure of Hansske et al. [*Tetrahedron*, 40, 125 (1984)]. According to this invention, the reduction was effected starting at -78° C. and allowing the reduction reaction to exothermically warm to about -2° C. This results in a high yield of the intermediate arabino compound.

In conjunction with use of a low temperature reduction, utilization of a tetraisopropyldisinloxane blocking group (a "TPDS" group) for the 3' and 5' positions of the starting guanosine compound contributes to an improved ratio of intermediate arabino compound to the ribo compound following oxidation and reduction. Following oxidation and reduction, the $N^2$ guanine amino nitrogen and the 2'-hydroxyl moieties of the intermediate arabino compound are blocked with isobutyryl protecting groups ("Ibu" groups). The tetraisopropyldisiloxane blocking group is removed and the 3' and 5' hydroxy groups are further protected with a second blocking group, a tetrahydropyranyl blocking group ("THP" group). The isobutyryl group is selectively removed from 2'-hydroxyl group followed by derivation of the 2' position with a triflate leaving group. The triflate group was then displaced with inversion about the 2' position to yield the desired 2'-deoxy-2'-fluoroguanosine compound.

In addition to the triflate leaving group, other leaving groups include, but are not limited to, alkylsulfonyl, substituted alkylsulfonyl, arylsulfonyl, substituted arylsulfonyl, heterocyclosulfonyl or trichloroacetimidate. Representative examples include p-(2,4-dinitroanilino)benzenesulfonyl, benzenesulfonyl, methylsulfonyl, p-methylbenzenesulfonyl, p-bromobenzenesulfonyl, trichloroacetimidate, acyloxy, 2,2, 2-trifluoroethanesulfonyl, imidazolesulfonyl and 2,4,6-trichlorophenyl.

The isobutyryl group remaining on the $N^2$ heterocyclic amino moiety of the guanine ring can be removed to yield a completely deblocked nucleoside. However, preferably, for incorporation of the 2'-deoxy-2'-substituted compound into an oligonucleotide, deblocking of the 2 isobutyryl protecting group is deferred until after oligonucleotide synthesis is complete. Normally for use in automated nucleic acid synthesizers, blocking of the $N^2$ guanine moiety with an isobutyryl group is preferred. Thus, advantageously, the $N^2$-isobutyryl-blocked 2'-deoxy-2'-substituted guanosine compounds resulting from the method of the invention can be directly used for oligonucleotide synthesis on automated nucleic acid synthesizers.

For the purpose of illustration, the oligonucleotides of the invention have been used in a rasluciferase fusion system using ras-luciferase transactivation. As described in International Publication Number WO 92/22651, published Dec. 23, 1992 and commonly assigned with this application, the entire contents of which are herein incorporated by reference, the ras oncogenes are members of a gene family that encode related proteins that are localized to the inner face of the plasma membrane. Ras proteins have been shown to be highly conserved at the amino acid level, to bind GTP with high affinity and specificity, and to possess GTPase activity. Although the cellular function of ras gene products is unknown, their biochemical properties, along with their significant sequence homology with a class of signal-transducing proteins known as GTP binding proteins, or G proteins, suggest that ras gene products play a fundamental role in basic cellular regulatory functions relating to the transduction of extracellular signals across plasma membranes.

Three ras genes, designated H-ras, K-ras, and N-ras, have been identified in the mammalian genome. Mammalian ras genes acquire transformation-inducing properties by single point mutations within their coding sequences. Mutations in naturally occurring ras oncogenes have been localized to codons 12, 13, and 61. The most commonly detected activating ras mutation found in human tumors is in codon-12 of the H-ras gene in which a base change from GGC to GTC results in a glycine-to-valine substitution in the GTPase regulatory domain of the ras protein produce. This single amino acid change is thought to abolish normal control of ras protein function, thereby converting a normally regulated cell protein to one that is continuously active. It is believed that such deregulation of normal ras protein function is responsible for the transformation from normal to malignant growth.

The oligonucleotides of the present invention have also been used for modulating the expression of the raf gene, a naturally present cellular gene which occasionally converts to an activated form that has been implicated in abnormal cell proliferation and tumor formation.

The oligonucleotides of the present invention are also specifically hybridizable with nucleic acids relating to protein kinase C (PKC). These oligonucleotides have been found to modulate the expression of PKC.

The following examples illustrate the present invention and are not intended to limit the same.

EXAMPLE 1

Preparation of 2'-Deoxy-2'-fluoro Modified Oligonucleotides.

A. $N^6$-Benzoyl-[2'-deoxy-2'-fluoro-5'-O-(4,4'-dimethoxytrityl)]adenosine-3'-O-(N,N-diisopropyl-β-cyanoethylphosphoramidite.

$N^6$-Benzoyl-9-(2'-fluoro-b-D-ribofuranosyl) adenine was prepared from 9-β-D-arabinofuranosyladenine in a five-step synthesis using a modification of a procedure reported by Ikehara at al. [*Nucleosides and Nucleotides*, 2, 373–385 (1983)]. The $N^6$-benzoyl derivative was obtained in good yield utilizing the method of transient protection with chlorotrimethylsilane. Jones [*J. Am. Chem. Soc.*, 104, 1316 (1982)]. Selective protection of the 3' and 5'-hydroxyl groups of $N^6$-Benzoyl-9-β-D-arabinofuranosyladenine with tetrahydropyranyl (THP) was accomplished by modification of the literature procedure according to Butke et al. [*Nucleic Acid Chemistry*, Part 3, p.149, L. B. Townsend and R. S. Tipson, Eds., J. Wiley and Sons, New York, 1986], to yield $N^6$-Benzoyl-9-[3',5'-di-O-tetrahydropyran-2-yl)-β-D-arabino-furanosyl]adenine in good yield. Treatment of $N^6$-Benzoyl-9-[3',5 -di-O-tetrahydropyran-2-yl)-β-D-arabino-furanosyl]adenine with trifluoromethanesulfonic anhydride in dichloromethane gave the 2'-triflate derivative $N^6$-Benzoyl-9-[2'-O-trifluoromethylsulfonyl-3',5'-di-O-tetrahydropyran-2-yl)-β-D-arabinofuranosyl] adenine which was not isolated due to its lability. Displacement of the 2'-triflate group was effected by reaction with tetrabutylammonium fluoride in tetrahydrofuran to obtain a moderate yield of the 2'-fluoro derivative $N^6$-Benzoyl-9-[2'-fluoro-3',5'-di-O-tetrahydropyran-2-yl)-β-D-arabinofuranosyl] adenine. Deprotection of the THP groups of $N^6$-Benzoyl-9-[2'-fluoro-3',5'-di-O-tetrahydro-pyran-2-yl)-β-D-arabinofuranosyl]adenine was accomplished by treatment with Dowex-SOW in methanol to yield $N^6$-benzoyl-9-(2'-deoxy-2'-fluoro-β-D-ribofuranosyl)adeninein moderate yield. The $^1$H-NMR spectrum was in agreement with the literature values. [Ikehara and Miki, *Chem. Pharm. Bull.*, 26, 2449 (1978)]. Standard methodologies were employed to obtain the 5'-dimethoxytrityl-3'-phosphoramidite intermediates $N^6$-Benzoyl-9-[2'-fluoro-5'-O-(4,4'-dimethoxytrityl)-β-D-ribofuranosyl]adenine and $N^6$-Benzoyl-[2'-deoxy-2'-fluoro -5'-O-(4,4'-dimethoxytrityl)]adenosine-3'-O-(N,N-diisopropyl-β-cyanoethylphosphoramidite. [Ogilyie, *Can J. Chem.*, 67, 831–839 (1989)].

B. $N^6$-Benzoyl-9-β-D-arabinofuranosyladenine.

9-β-D-arabinofuranosyladenine (1.07 g, 4.00 mmol) was dissolved in anhydrous pyridine (20 mL) and anhydrous dimethylformamide (20 mL) under an argon atmosphere. The solution was cooled to 0° C. and chlorotrimethylsilane (3.88 mL, 30.6 mmol) was added slowly to the reaction mixture via a syringe. After stirring the reaction mixture at 0° C. for 30 minutes, benzoyl chloride (2.32 mL, 20 mmol) was added slowly. The reaction mixture was allowed to warm to 20° C. and stirred for 2 hours. After cooling the reaction mixture to 0° C., cold water (8 mL) was added and the mixture was stirred for 15 minutes. Concentrated ammonium hydroxide (8 mL) was slowly added to the reaction mixture to give a final concentration of 2M of ammonia. After stirring the cold reaction mixture for 30 minutes, the solyent was evaporated in vacuo (60 torr) at 20° C. followed by evaporation in vacuo (1 torr) at 40° C. to give an oil. This oil was triturated with diethyl ether (50 mL) to give a solid which was filtered and washed with diethyl ether three times. This crude solid was triturated in methanol (100 mL) at reflux temperature three times and the solyent was evaporated to yield $N^6$-Benzoyl-9-β-D-arabino-furanosyladenine as a solid (1.50 g, 100%).

C. $N^6$-Benzoyl-9-[3',5'-di-O-tetrahydropyran-2-yl)-β-D-arabino furanosyl] adenine.

$N^6$-Benzoyl-9-β-D-arabinofuranosyladenine (2.62 g, 7.06 mmol) was dissolved in anhydrous dimethylformamide (150 mL) under argon and p-toluenesulfonic acid monohydrate (1.32 g, 6.92 mmol) was added. This solution was cooled to 0° C. and dihydropyran (1.26 mL, 13.8 mmol) was added via a syringe. The reaction mixture was allowed to warm to 20° C. Over a period of 5 hours a total of 10 equivalents of dihydropyran were added in 2 equivalent amounts in the fashion described. The reaction mixture was cooled to 0° C. and saturated aqueous sodium bicarbonate was added slowly to a pH of 8, then water was added to a volume of 750 mL. The aqueous mixture was extracted with methylene chloride (4×200 mL), and the organic phases were combined and dried over magnesium sulfate. The solids were filtered and the solyent was evaporated in vacuo (60 torr) at 30° C. to give a small volume of liquid which was evaporated in vacuo (1 torr) at 40° C. to give an oil. This oil was coevaporated with p-xylene in vacuo at 40° C. to give an oil which was dissolved in methylene chloride (100 mL). Hexane (200 mL) was added to the solution and the lower-boiling solyent was evaporated in vacuo at 30° C. to leave a white solid suspended in hexane. This solid was filtered and washed with hexane (3×10 mL) then purified by column chromatography using silica gel and methylene chloride-methanol (93:7) as the eluent. The first fraction yielded the title compound 3 as a white foam (3.19 g, 83%) and a second fraction gave a white foam (0.81 g) which was characterized as the 5'-monotetrahydropyranyl derivative of $N^6$-Benzoyl-9-β-D-arabinofuranosyladenine.

D. $N^6$-Benzoyl-9-[2'-O-trifluoromethylsulfonyl-3',5'-di-O-tetrahydropyran-2-yl)-β-D-arabinofuranosyl] adenine.

$N^6$-Benzoyl-9-[3',5'-di-O-tetrahydropyran-2-yl)-β-D-arabinofuranosyl]adenine (2.65 g, 4.91 mmol) was dissolved in anhydrous pyridine (20 mL) and the solvent was evaporated in vacuo (1 mm Hg) at 40° C. The resulting oil was dissolved in anhydrous methylene chloride (130 mL) under argon anhydrous pyridine (3.34 mL, 41.3 mmol) and N,N-dimethylaminopyridine (1.95 g, 16.0 mmol) were added. The reaction mixture was cooled to 0° C. and trifluoromethanesulfonic anhydride (1.36 mL, 8.05 mmol) was added slowly via a syringe. After stirring the reaction mixture at 0° C. for 1 hour, it was poured into cold aturated aqueous sodium bicarbonate (140 mL). The mixture was shaken and the organic phase was separated and kept at 0° C. The aqueous phase was extracted with methylene chloride (2×140 mL). The organic extracts which were diligently kept cold were combined and dried over magnesium sulfate. The solvent was evaporated in vacuo (60 torr) at 20° C. then evaporated in vacuo (1 torr) at 20° C. to give $N^6$-Benzoyl-9-[2'-O-trifluoromethylsulfonyl-3',5'-di-O-tetrahydropyran-2-yl)-β-D-arabinofuranosyl]adenine as a crude oil which was not purified further.

E. $N^6$-Benzoyl-9-[2'-fluoro-3',5'-di-O-tetrahydro-pyran-2-yl)-β-D-arabinofuranosyl]adenine.

$N^6$-Benzoyl-9-[2'-O-trifluoromethylsulfonyl-3',5'-di-O-tetrahydropyran-2-yl)-β-D-arabinofuranosyl]adenine(4.9 mmol) as a crude oil was dissolved in anhydrous tetrahydrofuran (120 mL) and this solution was cooled to 0° C. under argon. Tetrabutylammonium fluoride as the hydrate (12.8 g, 49.1 mmol) was dissolved in anhydrous tetrahydrofuran (50 mL) and half of this volume was slowly added via a syringe to the cold reaction mixture. After stirring at 0° C. for 1 hour, the remainder of the reagent was added slowly. The reaction mixture was stirred at 0° C. for an additional 1 hour, then the solvent was evaporated in vacuo (60 torr) at 20° C. to give an oil. This oil was dissolved in methylene chloride (250 mL) and washed with brine three times. The organic phase was separated and dried over magnesium sulfate. The solids were filtered and the solvent was evaporated to give an oil. The crude product was purified by column chromatography using silica gel in a sintered-glass funnel and ethyl acetate was used as the eluent. $N^6$-Benzoyl-9-[2'-fluoro-3',5'-di-O-tetrahydropyran-2-yl)-β-D-arabinofuranosyl]adenine was obtained as an oil (2.03 g, 76%).

F. $N^6$-Benzoyl-9-(2'-fluoro-β-D-ribofuranosyl)adenine.

$N^6$-Benzoyl-9-[2'-fluoro-3',5'-di-O-tetrahydropyran-2-yl)-β-D-arabinofuranosyl]adenine (1.31 g, 2.42 mmol) was dissolved in methanol (60 mL), and Dowex 50W×2-100 (4 cm³, 2.4 m.eq) was added to the reaction mixture. The reaction mixture was stirred at 2° C. for 1 hour then cooled to 0° C. Triethylamine (5 mL) was then slowly added to the cold reaction mixture to a pH of 12. The resin was filtered and washed with 30% triethylamine in methanol until the wash no longer contained UV absorbing material. Toluene (50 mL) was added to the washes and the solvent was evaporated at 24° C. in vacuo (60 torr, then 1 torr) to give a residue. This residue was partially dissolved in methylene chloride (30 mL) and the solvent was transferred to a separatory funnel. The remainder of the residue was dissolved in hot (60° C.) water and after cooling the solvent it was also added to the separatory funnel. The biphasic system was extracted, and the organic phase was separated and extracted with water (3×100 mL). The combined aqueous extracts were evaporated in vacuo (60 torr, then 1 torr Hg) at 40° C. to give an oil which was evaporated with anhydrous pyridine (50 mL). This oil was further dried in vacuo (1 torr Hg) at 20° C. in the presence of phosphorous pentoxide overnight to give $N^6$-benzoyl-9-(2'-fluoro-b-D-ribofuranosyl)adenine as a yellow foam (1.08 g, 100%) which contained minor impurities.

G. $N^6$-Benzoyl-9-[2'-fluoro-5'-O-(4,4'-dimethoxy-trityl)-β-D-ribofuranosyl]adenine.

$N^6$-Benzoyl-9-(2'-fluoro-b-D-ribofuranosyl)adenine (1.08 g, 2.89 mmol) which contained minor impurities was dissolved in anhydrous pyridine (20 mL) under argon and dry triethylamine (0.52 mL, 3.76 mmol) was added followed by addition of 4,4'-dimethoxytrityl chloride (1.13 g, 3.32 mmol). After 4 hours of stirring at 20° C. the reaction mixture was transferred to a separatory funnel and diethyl ether (40 mL) was added to give a white suspension. This mixture was washed with water three times (3×10 ml), the organic phase was separated and dried over magnesium sulfate. Triethylamine (1 ml) was added to the solution and the solyent was evaporated in vacuo (60 torr Hg) at 20° C. to give an oil which was evaporated with toluene (20 mL) containing triethylamine (1 mL). This crude product was purified by column chromatography using silica gel and ethyl acetate-triethylamine (99:1) followed by ethyl acetate-methanol-triethylamine (80:19:1) to give the product in two fractions. The fractions were evaporated in vacuo (60 torr, then 1 torr Hg) at 20° C. to give a foam which was further dried in vacuo (1 torr Hg) at 20° C. in the presence of sodium hydroxide to give $N^6$-Benzoyl-9-[2'-fluoro-5-O-(4,4-dimethoxytrityl)-β-D-ribofuranosyl]adenine as a foam (1.02 g, 52%).

H. $N^6$-Benzoyl-[2'-fluoro-5'-O-(4,4-dimethoxy trityl)]adenosine-3'-O-N,N-diisopropyl-β-cyanoethyl phosphoramidite.

$N^6$-Benzoyl-9-[2'-fluoro-5'-O-(4,4'-dimethoxytrityl)-β-D-ribofuranosyl]adenine (1.26 g, 1.89 mmol) was dissolved in anhydrous dichloromethane (13 mL) under argon, diisopropylethylamine (0.82 mL, 4.66 mmol) was added, and the reaction mixture was cooled to 0° C. Chloro (diisopropylamino)-β-cyanoethoxyphosphine (0.88 mL, 4.03 mmol) was added to the reaction mixture which was allowed to warm to 20° C. and stirred for 3 hours. Ethylacetate (80 mL) and triethylamine (1 mL) were added and this solution was washed with brine (3×25 mL). The organic phase was separated and dried over magnesium sulfate. After filtration of the solids the solyent was evaporated in vacuo at 20° C. to give an oil which was purified by column chromatography using silica gel and hexanes-ethyl acetate-triethyl-amine (50:49:1) as the eluent. Evaporation of the fractions in vacuo at 20° C. gave a foam which was evaporated with anhydrous pyridine (20 mL) in vacuo (1 torr) at 26° C. and further dried in vacuo (1 torr Hg) at 20° C. in the presence of sodium hydroxide for 24 h to give $N^6$-Benzoyl-[2'-deoxy-2'-fluoro-5'-O-(4,4'-dimethoxytrityl)]adenosine-3'-O-(N,N-diisopropyl-β-cyanoethylphosphoramidite as a foam (1.05 g, 63%).

I. 2'-Deoxy-2'-fluoro-5'-O-(4,4'-dimethoxytrityl)-uridine-3'-O-(N,N-diisopropyl-β-cyanoethyl-phosphoramidite).

2,2'-Cyclouridine is treated with a solution of 70% hydrogen fluoride/pyridine in dioxane at 120° C. for ten hours to provide after solvent removal a 75% yield of 2'-deoxy-2'-fluorouridine. The 5'-DMT and 3'-cyanoethoxydiisopropylphosphoramidite derivitized nucleoside is obtained by standard literature procedures [Gait, Ed., *Oligonucleotide Synthesis. A Practical Approach*, IRL Press, Washington, D.C. (1984)], or according to the procedure of Example 1A.

J. 2'-Deoxy-2'-fluoro-5'-O-(4,4'-dimethoxytrityl)-cytidine-3'-O-(N,N-diisopropyl-β-cyanoethyl phosphoramidite).

2'-Deoxy-2'-fluorouridine (2.51 g, 10.3 mmol) was converted to corresponding cytidine analog via the method of C. B. Reese, et al., *J. Chem. Soc. Perkin Trans I*, pp. 1171–1176 (1982), by acetylation with acetic anhydride (3.1 mL, 32.7 mmol) in anhydrous pyridine (26 mL) at room temperature. The reaction was quenched with methanol, the solvent was evaporated in vacuo (1 torr) to give an oil which was coevaporated with ethanol and toluene. 3',5'-O-diacetyl-2'-deoxy-2'-fluorouridine was crystallized from ethanol to afford colorless crystals (2.38 g, 81%).

N-4-(1,2,4-triazol-1-yl)-3',5'-O-diacetyl-2'-deoxy-2'-fluorouridine was obtained in a 70% yield (2.37 g) by reaction of 3',5'-O-diacetyl-2'-deoxy-2'-fluorouridine (2.75 g, 9.61 mmol) with 1,2,4-triazole (5.97 g, 86.5 mmol), phosphorus oxychloride (1.73 mL, 18.4 mmol), and triethylamine (11.5 mL, 82.7 mmol) in anhydrous acetonitrile at room temperature. After 90 min the reaction mixture was cooled to ice temperature and triethylamine (7.98 ml, 56.9 mmol) was added followed by addition of water (4.0 ml). The solvent was evaporated in vacuo (1 torr) to give an oil which was dissolved in methylene chloride and washed with saturated aqueous sodium bicarbonate. The aqueous phase was extracted with methylene chloride twice (2×100 mL) and the organic extracts dried with magnesium sulfate. Evaporation of the solvent afforded an oil from which the product N-4-(1,2,4-triazol-1-yl)-3',5'-O-diacetyl-2'-deoxy-2'-fluorouridine was obtained by crystallization from ethanol.

2'-deoxy-2'-fluorocytidine was afforded by treatment of protected triazol-1-yl derivative with concentrated ammonium hydroxide (4.26 mL, 81.2 mmol) in dioxane at room temperature for 6 hours. After evaporation of the solvent the oil was stirred in half-saturated (at ice temperature) ammonia in methanol for 16 hours. The solvent was evaporated and 2'-deoxy-2'-fluoro-cytidine crystallized from ethylacetate-methanol (v/v, 75:25) to give colorless crystals (1.24 g, 75%).

N-4-benzoyl-2'-deoxy-2'-fluorocytidine was prepared by selective benzoylation with benzoic anhydride in anhydrous dimethylformamide, V. Bhat, et al. *Nucleosides Nucleotides*, Vol. 8, pp. 179–183 (1989). The 5'-O-(4,4'-dimethoxytrityl) -3'-O-(N,N-diisopropyl-β-cyanoethyl-phosphoramidite) was prepared in accordance with Example 1A.

K. 9-(3',5'-[1,1,3,3-Tetraisopropyldisilox-1,3-diyl]-β-D-arabinofuranosyl)guanine.

The 3' and 5' positions of guanosine were protected by the addition of a TPDS (1,1,3,3-tetraisopropyldisilox-1,3-diyl) protecting group as per the procedure of Robins et al. [*Can. J. Chem.*, 61, 1911 (1983)]. To a stirred solution of DMSO (160 mL) and acetic anhydride (20 mL) was added the TPDS guanosine (21 g, 0.040 mol). The reaction was stirred at room temperature for 36 hours and then cooled to 0° C. Cold ethanol (400 mL, 95%) was added and the reaction mixture further cooled to -78° C. in a dry ice/acetone bath. NaBH$_4$ (2.0 g, 1.32 mol. eq.) was added. The reaction mixture was allowed to warm up to -2° C., stirred for 30 minutes and again cooled to -78° C. This was repeated twice. After the addition of NaBH$_4$ was complete, the reaction was stirred at 0° C. for 30 minutes and then at room temperature for 1 hour. The reaction was taken up in ethyl acetate (1 L) and washed twice with a saturated solution of NaCl. The organic layer was dried over MgSO$_4$ and evaporated under reduced pressure. The residue was coevaporated twice with toluene and purified by silica gel chromatography using CH$_2$Cl$_2$-MeOH (9:1) as the eluent. Pure product (6.02 g) precipitated from the appropriate column fractions during evaporation of these fractions, and an additional 11.49 g of product was obtained as a residue upon evaporation of the fractions.

L. N$^2$-IsobutyryL-9-(2'-O-isobutyryl-3',5'-[1,1,3,3-tetraisopropyldisilox-1,3-diyl]β-D-arabinofuranosyl) guanine.

9-(3',5'-[1,1,3,3-Tetraisopropyldisilox-1,3-diyl]β-D-arabinofuranosyl)guanine (6.5 g, 0.01248 mol) was dissolved in anhydrous pyridine (156 mL) under argon. DMAP (9.15 g) was added. Isobutyric anhydride (6.12 mL) was slowly added and the reaction mixture stirred at room temperature overnight. The reaction mixture was poured into cold saturated NaHCO$_3$ (156 mL) and stirred for 10 minutes. The aqueous solution was extracted three times w:Lth ethyl acetate (156 mL). The organic phase was washed three times with saturated NaHCO$_3$ and evaporated to dryness. The residue was coevaporated with toluene and purified by silica gel column chromatography using CH$_2$Cl$_2$-acetone (85:15) to yield 5.67 g of product.

M. N$^2$-Isobutyryl-9-(2'-O-isobutyryl-β-D-arabinofuranosyl) guanine.

N$^2$-Isobutyryl-9-(2'-isobutyryl-3',5'-[1,1,3,3-tetraisopropyldisilox-1,3-diyl]-β-D-arabinofuranosyl) guanine (9.83 g, 0.01476 mol) was dissolved in anhydrous THF (87.4 mL) at room temperature under argon. 1M (nBu)$_4$N$^{+F-}$ in THF (29.52 mL, 2 eq.) was added and the reaction mixture stirred for 30 minutes. The reaction mixture was evaporated at room temperature and the residue purified by silica gel column chromatography using EtOAc-MeOH (85:15) to yield 4.98 g (80%) of product.

N. N$^2$-Isobutyryl-9-(2'-O-isobutyryl-3',5'-di-O-[tetrahydropyran-2-yl]-β-D-arabinofuranosyl)guanine.

N$^2$-Isobutyryl-9-(2'-isobutyryl-β-D-arabinofuranosyl) guanine (4.9 g) was dissolved in anhydrous 1,4-dioxane (98 mL) at room temperature under argon. p-Toluenesulphonic acid monohydrate (0.97 g) was added followed by 3,4-dihydro-2H-pyran (DHP, 9.34 mL, 8.8 eq.). The reaction mixture was stirred for 2 hours, then cooled to 0° C. and saturated NaHCO$_3$ (125 mL) was added to quench the reaction. The reaction mixture was extracted three times with 125 mL portions of CH$_2$Cl$_2$ and the organic phase dried over MgSO$_4$. The organic phase was evaporated and the residue dissolved in minimum volume of CH$_2$Cl$_2$, but in an amount sufficient to yield a clear liquid not a syrup, and then dripped into hexane (100 times the volume of CH$_2$Cl$_2$). The precipitate was filtered to yield 5.59 (81.5%) of product.

O. N$^2$-Isobutyryl-9-(3',5'-di-O-[tetrahydropyran-2-yl]-β-D-arabinofuranosyl)guanine.

N$^2$-Isobutyryl-9-(2'-isobutyryl-3',5'-di-O-[tetrahydropyran-2-yl]-β-D-arabinofuranosyl)guanine (5.58 g) was dissolved in pyridine-MeOH-H$_2$O (65:30:15, 52 mL) at room temperature. The solution was cooled to 0° C. and 52 mL of 2N NaOH in EtOH—MeOH (95:5) was added slowly, followed by stirring for 2 hours at 0° C. Glacial acetic acid was added to pH 6, and saturated NaHCO$_3$ was added to pH 7. The reaction mixture was evaporated under reduced pressure and the residue coevaporated with toluene. The residue was then dissolved in EtOAc (150 mL) and washed 3× with saturated NaHCO$_3$. The organic phase was evaporated and the residue purified by silica gel column chromatography using EtOAc-MeOH (95:5) as the eluent, yielding 3.85 g (78.3%) of product.

P. N$^2$-Isobutyryl-9-(3',5'-di-O-[tetrahydropyran-2-yl]-2'-O-trifluoromethylsulfonyl-β-D-arabinofuranosyl)guanine.

N$^2$-Isobutyryl-9-(3',5'-di-O-[tetrahydropyran-2-yl]-β-D-arabinofuranosyl)guanine (3.84 g) was dissolved in anhydrous CH$_2$Cl$_2$ (79 mL), anhydrous pyridine (5 mL) and DMAP (2.93 g) at room temperature under argon. The solution was cooled to 0° C. and trifluoromethanesulfonic anhydride (1.99 mL) was slowly added with stirring. The reaction mixture was stirred at room temperature for 1 hour then poured into 100 mL of saturated NaHCO$_3$. The aqueous phase was extracted three times with cold CH$_2$Cl$_2$. The organic phase was dried over MgSO$_4$, evaporated and coevaporated with anhydrous MeCN to yield a crude product.

Q. N$^2$-Isobutyryl-9-(2'-deoxy-2'-fluoro-3',5'-di-O-[tetrahydropyran-2-yl]-2'-O-trifluoromethylsulfonyl-β-D-ribofuranosyl)guanine.

The crude product from Example 1-P, i.e. N$^2$-isobutyryl-9-(3',5'-di-O-[tetrahydropyran-2-yl]-2'-O-trifluoromethylsulfonyl-β-D-arabinofuranosyl)guanine was dissolved in anhydrous THF (113 mL) under argon at 0° C. 1M (nBu)$_4$N$^+$F$^-$ (dried by coevaporation with pyridine) in THF (36.95 mL) was added with stirring. After 1 hour, a further aliquot of (nBu)$_4$N$^+$F$^-$ in THF (36.95 mL) was added. The reaction mixture was stirred at 0° C. for 5 hours and stored overnight at −30° C. The reaction mixture was evaporated under reduced pressure and the residue dissolved in CH$_2$Cl$_2$ (160 mL) and extracted five times with deionized water. The organic phase was dried over MgSO$_4$ and evaporated. The residue was purified by silica gel column chromatography using EtOAc-MeOH (95:5) to yield 5.25 g of product.

R. N$^2$-Isobutyryl-9-(2'-deoxy-2'-fluoro-β-D-ribofuranosyl) guanine.

N$^2$-isobutyryl-9-(2'-deoxy-2'-fluoro-3',5'-di-O-[tetrahydropyran-2-yl] -β-D-ribofuranosyl)guanine (3.85 g) was dissolved in MeOH (80 mL) at room temperature. Pre-washed Dowex 50W resin (12.32 cm$^3$) was added and the reaction mixture stirred at room temperature for 1 hour. The resin was filtered and the filtrate evaporated to dryness. The resin was washed with pyridine-triethylamine-H$_2$O (1:3:3) until filtrate was clear. This filtrate was evaporated to obtain an oil. The residues from both filtrates were combined in H$_2$O (200 mL) and washed with CH$_2$Cl$_2$ (3×100 mL). The aqueous phase was evaporated to dryness and the residue recrystallized from hot MeOH to yield 0.299 g of product as a white powder. The remaining MeOH solution was purified by silica gel column chromatography to further yield 0.783 g of product by elution with EtOH—MeOH (4:1).

S. N$^2$-Isobutyryl-9-(2'-deoxy-2'-fluoro-5'-O-[4,4-dimethoxytrityl]-β-D-ribofuranosyl)guanine.

N$^2$-isobutyryl-9-(2'-deoxy-2'-fluoro-β-D-ribofuranosyl) guanine (1.09 g) was dissolved in pyridine (20 mL) and triethylamine (0.56 mL) at room temperature under argon. 4,4'-Dimethoxytrityl chloride (1.20 g, 1.15 molar eq.) was added and the reaction mixture stirred at room temperature for 5 hours. The mixture was transferred to a separatory funnel and extracted with diethyl ether (100 mL). The organic phase was washed with saturated NaHCO$_3$ (3×70 mL), and the aqueous phase back-extracted three times with diethyl ether. The combined organic phases were dried over MgSO$_4$ and triethylamine (4 mL) was added to maintain the solution at basic pH. The solvent was evaporated and the residue purified by silica gel column chromatography using EtOAc-triethylamine (100:1) and then EtOAc-MeCH-triethylamine (95:5:1) as eluents yielding 1.03 g of product.

T. N$^2$-Isobutyrl-9-(2'-deoxy-2'-fluoro-5'-O-[4,4-dimethoxytrityl]-guanosine-3'-O-N,N-diisopropyl-β-D-cyanoethyl phosphoramidite.

N$^2$-isobutyryl-9-(2'-deoxy-2'-fluoro-5'-O-[4,4'-dimethoxytrityl])-β-D-ribofuranosyl)guanine (0.587 g) was dissolved in anhydrous CH$_2$Cl$_2$ (31 mL) and diisopropylethylamine (0.4 mL) at room temperature under argon. The solution was cooled to 0° C. and chloro (diisopropylamino) -9-cyanoethoxyphosphine (0.42 mL) was slowly added. The reaction mixture was allowed to warm to room temperature and stirred for 3.5 hours. CH$_2$Cl$_2$-triethylamine (100:1, 35 mL) was added and the mixture washed with saturated NaHCO$_3$ (6 mL). The organic phase was dried over MgSO$_4$ and evaporated under reduced pressure. The residue was purified by silica gel column chromatography using hexane-EtOAc-triethylamine (75:25:1) for 2 column volumes, then hexane-EtOAc-triethylamine (25:75:1), and finally EtOAc-triethylamine. The product-containing fractions were pooled and the solvent evaporated under reduced pressure. The resulting oil was coevaporated twice with MeCN and dried under reduced pressure. The resulting white solid was dissolved in CH$_2$Cl$_2$ (3 mL) and dripped into stirring hexane (300 mL). The resulting precipitate was filtered and dried under reduced pressure to yield 0.673 g (88%) of product.

EXAMPLE 2

Preparation of 2'-Deoxy-2'-cyano Modified Oligonucleotides.

A. N$^6$-Benzoyl-[2'-deoxy-2'-cyano-5'-O-(4,4'-dimethoxytrityl]adenosine-3'-O-(N,N-diisopropyl-β-cyanoethylphosphoramidite).

2'-Deoxy-2'-cyanoadenosine is prepared by the free radical replacement of the 2'-iodo group of 2'-deoxy-2'-iodo-3', 5'-O-(disiloxytetraisopropyl)-N$^6$-benzoyladenosine according to a similar procedure described by Parkes and Taylor [*Tetrahedron Letters*, 29, 2995 (1988)]. 2'-Deoxy-2'-iodoadenosine was prepared by Ranganathan as described in *Tetrahedron Letters*, 15, 1291 (1977), and disilyated as described by Markiewicz and Wiewiorowski [*Nucleic Acid Chemistry*, Part 3, pp. 222–231, L. B. Townsend and R. S. Tipson, Eds., J. Wiley and Sons, New York, 1986. This material is treated with hexamethylditin, AIBN , and t-butylisocyanate in toluene to provide protected 2'-deoxy-2'-cyanoadenosine. This material, after selective deprotection, is converted to its 5'-DMT-3'-phosphoramidite as described in Example 1A.

B. 2'-Deoxy-2'-cyano-5'-O-(4,4'-dimethoxytrityl)-uridine-3'-O-(N,N-diisopropyl-β-cyanoethyl phosphoramidite).

2'-Deoxy-2'-iodouridine (or 5-methyluridine), 3',5'-disilylated as described above, is converted to the 2'-iodo derivative by triphenylphosphonium methyl iodide treatment as described by Parkes and Taylor [*Tetrahedron Letters*, 29, 2995 (1988)]. Application of free radical reaction conditions as described by Parkes and Taylor provides the 2'-cyano group of the protected nucleoside. Deprotection of this material and subsequent conversion to the protected monomer as described above provides the requisite phosphoramidite.

C. 2'-Deoxy-2'-cyano-5'-O-(4,4'-dimethoxytrityl)-cytidine-3'-O-(N,N-diisopropyl-β-cyanoethyl phosphoramidite).

2'-Deoxy-2'-iodocytidine is obtained from the corresponding uridine compound described above via a conventional keto to amino conversion.

D. 2'-Deoxy-2'-cyano-5'-O-(4,4'-dimethoxytrit yl)-guanosine-3'-O-(N,N-diisopropyl-b-cyanoethyl phosphoramidite).

2'-Deoxy-2'-cyanoguanosine is obtained by the displacement of the triflate group in the 2'-position (arabinosugar) of 3',5'-disilylated N$^2$-isobutrylguanosine. Standard deprotection and subsequent reprotection provides the title monomer.

EXAMPLE 3

Preparation of 2'-Deoxy-2'-(trifluoromethyl) Modified oligonucleotides.

The requisite 2'-deoxy-2'-trifluromethyribosides of nucleic acid bases A, G, U(T), and C are prepared by modifications of a literature procedure described by Chen and Wu [*Journal of Chemical Society, Perkin Transactions*, 2385 (1989)]. Standard procedures, as described in Example 1A, are employed to prepare the 5'-DMT and 3'-phosphoramidites as listed below.

A. $N^6$-Benzoyl-[2'-deoxy-2'-trifluoromethyl-5'-O-(4,4'-dimethoxytrityl)]adenosine-3'-O-(N,N-di-isopropyl-β-cyanoethyl phosphoramidite).

B. 2'-Deoxy-2'-trifluoromethyl-5'-O-(4,4'-dimethoxytrityl) uridine-3'-O-(N,N-diisopropyl-β-cyanoethylphosphoramidite).

C. 2'-Deoxy-2'-trifluoromethyl-5'-O-(4,4'-dimethoxytrityl)-cytidine-3'-O-(N,N-diisopropyl-β-cyanoethylphosphoramidite).

D. 2'-Deoxy-2'-trifluoromethyl-5'-O-(4,4'-dimethoxytrity)-guanosine-3'-O-(N,N-diisopropyl-β-cyanoethylphosphoramidite).

EXAMPLE 4

Preparation of 2'-Deoxy-2'-(trifluoromethoxy) Modified oligonucleotides.

The requisite 2'-deoxy-2'-O-trifluromethyribosides of nucleic acid bases A, G, U(T), and C are prepared by modifications of literature procedures described by Sproat et al. [*Nucleic Acids Research*, 18, 41 (1990)] and Inoue et al. [*Nucleic Acids Research*, 15:, 131 (1987)]. Standard procedures, as described in Example 1A, are employed to prepare the 5'-DMT and 3'-phosphoramidites as listed below.

A. N6-Benzoyl-[2'-deoxy-2'-(trifluoromethoxy)-5'-O-(4,4'-dimethoxytrityl)]adenosine-3'-O-(N,N-diisopropyl-β-cyanoethylphosphoramidite).

B. 2'-Deoxy-2'-(trifluoromethoxy)-5'-O-(4,4'-dimethoxytrityl)-uridine-3'-O-(N,N-diisopropyl-β-cyanoethylphosphoramidite).

C. 2'-Deoxy-2'-(trifluoromethoxy)-5'-O-(4,4'-dimethoxytrityl)-cytidine-3'-O-(N,N-diisopropyl-β-cyanoethylphosphoramidite).

D. 2'-Deoxy-2'-(trifluoromethoxy)-5'-O-(4,4'-dimethoxytrityl)-guanosine-3'-O-(N,N-diisopropyl-β-cyanoethylphosphoramidite).

EXAMPLE 5

Preparation of 2'-Deoxy-2'-O-alkyl Modified Oligonucleotides.

Illustrative 2'-O-alkyl (2'-alkoxy) modified oligonucleotides are prepared from appropriate precursor nucleotides that in turn are prepared starting from a commercial nucleoside. The nucleoside, either unblocked or appropriately blocked as necessary to protected exocyclic functional groups on their heterobases, are alkylated at the 2'-O position. This 2'-O-alkylated nucleosides is converted to a 5'-O-dimethoxytrityl protected nucleosides and 3'-O-phosphitylated to give a phosphoramidite. The phosphoramidites are incorporated in oligonucleotides using standard machine cycle solid phase phosphoramidite oligonucleotide chemistry. For illustrative purposes the synthesis of 2-O-nonyladenosine, 2-O-propyluridine, 2-O-methylcytidine, 2'-O-octadecylguanosine, 2-O-[(N-phthalimido)prop-3-yl]-$N^6$-benzoyladenosine and 2-O-[(imidazol-1-yl)but-4-yl]adenosine are given. Other 2'-O-alkylated nucleosides are prepared in a like manner using an appropriate starting alkyl halide in place of the illustrated alkyl halides. For certain 2'-O-aminoalkyl compounds of the invention, protected amines, e.g. phthalimido, were used during alkylation, subsequent tritylation and phosphitylation. After incorporation into the oligonucleotide of interest, the 2'-O-protected aminoalkyl moiety are deblocked to yield the free amino compound, i.e 2'-O—$(CH_2)_n$—$NH_2$.

A. $N^6$-Benzoyl-[2'-deoxy-2'-O-nonyl-5'-O-(4,4'-dimethoxytrityl)]adenosine-3'-O-(N,N-diisopropyl-β-cyanoethylphosphoramidite).

2'-O-Nonyladenosine

To a solution of 10 g of adenosine in 400 ml of dimethyl formamide was added 2.25 g of 60% sodium hydride (oil). After one hour, 8.5 ml of 1-bromononane was added. The reaction was stirred for 16 hours. Ice was added and the solution evaporated in vacuo. Water and ethyl acetate were added. The organic phase was separated, dried, and evaporated in vacuo to give a white solid, which was recrystallized from ethanol to yield 4.8 g of the title compound, m.p. 143°–144° C. analysis for: $C_{19}H_{31}N_5O_4$ Calculated: C, 57.99; H, 7.94; N, 1779. Found: C, 58.13; H, 7.93; N, 17.83.

2'-O-Nonyl-$N^6$-benzoyladenosine

2'-O-Nonyladenosine was treated with benzoyl chloride in a manner similar to the procedure of B. L. Gaffney and R. A. Jones, *Tetrahedron Lett.*, Vol. 23, p. 2257 (1982). After chromatography on silica gel (ethyl acetate-methanol), the title compound was obtained. Analysis for: $C_{26}H_{35}N_5O_5$. Calculated: C, 62.75; H, 7.09; N, 17.07. Found: C, 62.73; H, 14.07; N, 13.87.

2'-O-Nonyl-5'-O-dimethoxytrityl-$N^6$-benzoyladenosine

To a solution of 4.0 g of 2'-O-nonyl-$N^6$-benzoyladenosine in 250 ml of pyridine was added 3.3 g of 4,4'-dimethoxytrityl chloride. The reaction was stirred for 16 hours. The reaction was added to ice/water/ethyl acetate, the organic layer was separated, dried, and concentrated in vacuo to a gum. 5.8 g of the title compound was obtained after chromatography on silica gel (ethyl acetate-methanol triethylamine). Analysis for: $C_{47}H_{53}N_5O_7$. Calculated: C, 70.56; H, 6.68; N, 8.75. Found: C, 70.26; H, 6.70; N, 8.71.

$N^6$-Benzoyl-5'-O-dimethoxytrityl-2'-O-nonyladenosine-3'-O,N,N-diisopropyl-β-cyanoethyl phosphoramidite 2'-o-nonyl-5'-O-dimethoxytrityl-N-benzoyladenosine was treated with (β-cyanoethoxy)chloro(N,N-diisopropyl)-aminephosphane in a manner similar to the procedure of F. Seela and A. Kehne, *Biochemistry*, Vol. 26, p. 2233 (1987). After chromatography on silica gel (E=OAC/hexane), the title compound was obtained as a white foam.

B. 2'-Deoxy-2'-O-propyl-5'-O-(4,4'-dimethoxy-trityl)-uridine-3'-O-(N,N-diisopropyl-β-cyanoethylphosphoramidite).

3',5'-O-(1,1,3,3)Tetraisopropyl-1,3-disiloxanediyluridine

With stirring, uridine (40 g, 0.164 mol) and 1,3-dichloro-1,1,3,3-tetraisopropyldisiloxane (TIPS-Cl, 50 g, 0.159 mol) were added to dry pyridine (250 mL). After stirring for 16 h at 25° C., the reaction was concentrated under reduced pressure to an oil. The oil was dissolved in methylene chloride (800 mL) and washed with sat'd sodium bicarbonate (200 g) scrub column. The product was recovered by elution with methylene chloride-methanol (97:3). The appropriate fractions were combined, evaporated under reduced pressure and dried at 25° C./0.2 mmHg for 1 h to give 65 g (84%) of tan oil; TLC purity 95% (Rf 0.53, ethyl acetate-methanol 95:5); PMR ($CDCl_3$) δ 7.87 (d, 1, H-6), 5.76 (d, 1, H-5), 5.81 (s, 1, H-1').

$N^3$-(4-Toluoyl)-3'-5'-O-(1,1,3,3)tetraisopropyl-1,3-disiloxanediyluridine

4-Toluoyl chloride (19.6 g, 0.127 mol) was added over 30 min to a stirred solution of 3',5'-O-(1,1,3,3)-tetraisopropyl-1,3-disiloxanediyluridine (56 g, 0.115 mol) and triethylamine (15.1 g, 0.15 mol) in dimethylacetamide (400 mL) at 5° C. The mixture was allowed to warm to 25° C. for 3 h and then poured onto ice water (3.5 L) with stirring. The resulting solid was collected, washed with ice water (3×500 mL) and dried at 45° C./0.2 mmHg for 5 h to afford 49 g (70%) of tan solid; mp slowly softens above 45° C.; TLC purity ca. 95% (Rf 0.25, hexanes-ethyl acetate 4:1); PMR (DMSO) δ 7.9 (H-6), 7.9–7.4 (Bz), 5.8 (H-5), 5.65 (HO-2'), 5.6 (H-1'), 2.4 (CH$_3$—Ar).

N$^3$-(4-Toluoyl)-2'-O-propyl-3',5'-O-(1,1,3,3)tetraisopropyl-1,3-disiloxanediyluridine A mixture of N$^3$-(4-toluoyl)-3'-5'-O-(1,1,3,3) tetraisopropyl-1,3-disiloxane-diyluridine (88 g, 0.146 mol, 95% purity), silyer oxide (88 g, 0.38 mol) and toluene (225 mL) was evaporated under reduced pressure. More toluene (350 mL) was added and an additional amount (100 mL) was evaporated. Under a nitrogen atmosphere, propyl iodide was added in one portion and the reaction was stirred at 40° C. for 16 h. The silyer salts were collected and washed with ethyl acetate (3×150 mL). The combined filtrate was concentrated under reduced pressure. The residue was dissolved in a minimum of hexanes, applied on a silica gel column (800 g) and eluted with hexanes-ethyl acetate (9:1→4:1). The appropriate fractions were combined, concentrated under reduced pressure and dried at 25° C./0.2 mmHg for 1 h to provide 68 g (74%) of tan oil; TLC purity 95% (Rf 0.38, hexanes-ethyl acetate 4:1); PMR (CDCl$_3$) δ 8.1–7.3 (m, 6, H-6 and Bz), 5.8 (H-5), 5.76 (H-1').

2'-O-Propyluridine

A solution of N$^3$-(4-toluoyl)-2'-O-propyl-3',5'-O-(1,1,3,3) tetraisopropyl-1,3-disiloxanediyluridine (27 g) in methanol (400 mL) and ammonium hydroxide (50 mL) was stirred for 16 h at 25° C. The reaction was concentrated under reduced pressure to an oil; TLC homogenous (Rf 0.45, ethyl acetate-methanol 95:5).

The oil was dissolved in toluene (100 mL) and the solution was evaporated under reduced pressure to dryness. The residue was dissolved in tetrahydrofuran (300 mL). Tetrabutylammonium fluoride solution (86 mL, 1M in tetrahydrofuran) was added and the reaction was stirred at 25° C. for 16 h. The pH was adjusted to 7 with Amberlite IRC-50 resin. The mixture was filtered and the resin was washed with hot methanol (2×200 mL). To the combined filtrate was added silica gel (40 g). The suspension was concentrated under reduced pressure to a dry powder. The residue was placed on top of a silica gel column (500 g) and eluted with ethyl acetate and then ethyl acetate-methanol (9:1). The appropriate fractions were combined, evaporated under reduced pressure and dried at 90° C./0.2 mmHg for 5 h to yield 8.0 g (70%) of light tan solid; TLC purity 98% (Rf 0.45, ethyl acetate-methanol 4:1); PMR (DMSO) δ 11.37 (H-N$^3$), 7.9 (H-6), 5.86 (H-1'), 5.65 (H-5), 5.2 (HO-3',5').

5'-O-(4,4'-Dimethoxytriphenylmethyl)-2'-O-propyluridine

2'-O-Methyluridine (8.0 g) was evaporated under reduced pressure to an oil with pyridine (100 mL). To the residue was added 4,4'-dimethoxytriphenylmethyl chloride (DMT-Cl, 11.5 g, 0.34 mol) and pyridine (100 mL). The mixture was stirred at 25° C. for 1.5 h and then quenched by the addition of methanol (10 mL) for 30 min. The mixture was concentrated under reduced pressure and. the residue was chromatographed on silica gel (250 g, hexanes-ethyl acetate-triethylamine 80:20:1 and then ethyl acetate-triethylamine 99:1). The appropriate fractions were combined, evaporated under reduced pressure and dried at 25° C./0.2 mmHg for 1 h to provide 17.4 g (100%, 30% from uridine) of tan foam; TLC purity 98% (Rf 0.23, hexanes-ethyl acetate 4:1); PMR (DMSO) δ 11.4 (H-N$^3$), 7.78 (H-6), 7.6–6.8 (Bz), 5.8 (H-1'), 5.3 (H-5'), 5.25 (HO-3'), 3.7 (CH$_3$O—Bz).

[5'-O-(4,4'-dimethoxytriphenylmethyl)-2'-O-propyluridin-3'-O-yl]-N,N-diisopropylaminocyanoethoxyphosphoramidite The product was prepared in the same manner as the adenosine analog above by starting with intermediate 5'-O-(4,4'-dimethoxytriphenylmethyl)-2'-O-propyluridine and using ethyl acetate-hexanes-triethylamine 59:40:1 as the chromatography eluent to give the product as a solid foam in 60% yield (18% from uridine); TLC homogenous diastereomers (Rf 0.58; 0.44, ethyl acetate-hexanes-triethylamine 59:40:1); $^3$P-NMR (CDCl$_3$, H$_3$PO$_4$ std.) 6 148.11; 148.61 (diastereomers) C. 2'-Deoxy-2'-O-methyl-5'-O-(4,4'-dimethoxytrityl)-cytidine-3'-O-(N,N-diisopropyl-.g-cyano- ethylphosphoram:Ldite).

Two methods will be described for the preparation of the intermediate N$^4$-benzoyl-2'-O-methylcytidine. Method A involyes blocking of the 3'-5' sites with the TIPS-Cl reagent to allow alkylation only on the 2' position. Method B uses a direct alkylation of cytidine followed by separation of the resulting mixture. The overall yields are comparable. Method A: 3',5'-O-(1,1,3,3)-Tetraisopropyl-1,3-disiloxanediylcvtidine With stirring, cytidine (40 g, 0.165 mol) and 1,3-dichloro-1,1,3,3-tetraisopropyldisiloxane (TIPS-Cl, 50 g, 0.159 mol) were added to dry pyridine (250 mL). After stirring for 16 h at 25° C., the reaction was concentrated under reduced pressure to an oil. The oil was dissolved in methylene chloride (800 mL) and washed with sat'd sodium bicarbonate (2×300 mL). The organic layer was passed through a silica gel (200 g) scrub column. The product was recovered by elution with methylene chloride:methanol (97:3). The appropriate fractions were combined, evaporated under reduced pressure and dried at 25° C./0.2 mmHg for 1 h to give 59.3 g (77.6) of oil (the product may be crystallized from ethyl acetate as white crystals, mp 242–244. IC.); TLC purity 95% (Rf 0.59, ethyl acetate-methanol 9:1); PMR (DMSO) 6 7.7 (H-6), 5.68 (H-5), 5.61 (HO-2'), 5.55 (H-1'). N$^4$-(Benzoyl)-3'-5'-O-(1,1,3,3)tetraisopropyl-1,3-disiloxanediylcytidine Benzoyl chloride (18.5 g, 0.13 mol) was added over 30 min to a stirred solution of 3',5'-O-(1,1,3,3)-tetraisopropyl-1,3-disilcxanediylcytidine (58 g, 0.12 mol) and triethylamine (15.6 g, 0.16 mol) in dimethylacetamide (400 mL) at 5° C. The mixture was allowed to warm to 25° C. for 16 h and then poured onto ice water (3.5 L) with stirring. The resulting solid was collected, washed with ice water (3×500 mL) and dried at 45° C./0.2 mmHg for 5 h to provide 77 g (100%) of solid; TLC purity ca. 90% (Rf 0.63, chloroform-methanol 9:1); PMR (CDCL$_3$) δ 8.32 (H-6). Lit. mp 100°–101° C.

N$^4$-(Benzoyl)-2'-O-methyl-3',5'-O-(1,1,3,3)tetraisopropyl-1,3-disiloxanediylcytidine A mixture of N$^4$-(benzoyl)-3'-5'-O-(1,1,3,3) tetraisopropyl-1,3-disiloxanediylcytidine (166 g, 0.25 mol, 90% purity), silyer oxide (150 g, 0.65 mol) and toluene (300 mL) was evaporated under reduced pressure. More toluene (500 mL) was added and an additional amount (100 mL) was evaporated. Under a nitrogen atmosphere, methyl iodide was added in one portion and the reaction was stirred at 4° C. for 16 h. The silyer salts were collected and washed with ethyl acetate (3×150 mL). The combined filtrate was concentrated under reduced pressure. The residue was dissolved in a minimum of methylene chloride, applied to a silica gel column (1 kg) and eluted with hexanes-ethyl acetate (3:2®1:1). The appropriate fractions were combined, concentrated under reduced pressure and dried at 45° C./0.2 mmHg for 1 h to yield 111 g (66%) of oil; TLC purity ca. 90% (Rf 0.59, hexanes-ethyl acetate 3:2). PMR (CDCl$_3$) δ 8.8 (br s, 1, H-N$^4$), 8.40 (d, 1, H-6), 8.0–7.4 (m, 6, H-5 and Bz), 5.86 (s, 1, H-1'), 3.74 (s, 3, CH$_3$O-2').

N$^4$-Benzoyl-2'-O-methylcytidine

A solution of N$^4$-(benzoyl)-2'-O-methyl-3',5'-O-(1,1,3,3) tetraisopropyl-1,3-disiloxanediylcytidine (111 g, 0.18 mol) in methanol (160 mL) and tetrahydrofuran (640 mL) was treated with tetrabutylammonium fluoride solution (368 mL, 1M in tetrahydrofuran). The reaction was stirred at 25° C. for 16 h. The pH was adjusted to 7 with Amberlite IRC-50 resin. The mixture was filtered and the resin was washed with hot methanol (2×200 mL). The combined filtrate was concentrated under reduced pressure, absorbed on silica gel (175 g) and chromatographed on silica gel (500 g, ethyl acetate-methanol 19:1®4:1). Selected fractions were combined, concentrated under reduced pressure and dried at 40° C./0.2 mmHg for 2 h to yield 28 g (42.4%, 21.5% from cytidine) of solid; TLC homogenous (Rf 0.37, ethyl acetate). mp 178°–180° C. (recryst. from ethanol); PMR (CDCl$_3$) δ 11.22 (br s, 1, H-N$^4$), 8.55 (d, 1, H-6), 8.1–7.2 (m, 6, H-5 and Bz), 5.89 (d, 1, H-1'), 5.2 (m, 2, HO-3',5'), 3.48 (s, 3, CH$_3$O-2').

Method B
N$^4$-Benzoyl-2'-O-methylcytidine

Cytidine (100 g, 0.41 mol) was dissolved in warm dimethylformamide (65° C., 1125 mL). The solution was cooled with stirring to 0° C. A slow, steady stream of nitrogen gas was delivered throughout the reaction. Sodium hydride (60% in oil, washed thrice with hexanes, 18 g, 0.45 mol) was added and the mixture was stirred at 0° C. for 45 min. A solution of methyl iodide (92.25 g, 40.5 mL, 0.65 mol) in dimethylformamide (400 mL) was added in portions over 4 h at 0° C. The mixture was stirred for 7 h at 25° C. and then filtered. The filtrate was concentrated to dryness under reduced pressure followed by coevaporation with methanol (2×200 mL). The residue was dissolved in methanol (350 mL). The solution was adsorbed on silica gel (175 g) and evaporated to dryness. The mixture was slurried in dichloromethane (500 mL) and applied on top of a silica gel column (1 kg). The column was eluted with a gradient of dichloromethane-methanol (10:1®2:1). The less polar 2',3'-dimethyl side product was removed and the coeluting 2' and 3'-O-methyl product containing fractions were combined and evaporated under reduced pressure to a syrup. The syrup was dissolved in a minimum of hot ethanol (ca. 150 mL) and allowed to cool to 25° C. The resulting precipitate (2' less soluble) was collected, washed with ethanol (2×25 ml) and dried to give 15.2 g of pure 2'-O-methylcytidine; mp 252°–254° C. (lit. mp 252°–254° C.); TLC homogenous (Rf 0.50, dichloromethanemethanol 3:1, (Rf of 3' isomer is 0.50 and the dimethyl product is 0.80). The filtrate was evaporated to give 18 g of a mixture of isomers and sodium iodide.

The pure 2'-O-methylcytidine (15.2 g, 0.060 mol) was dissolved in a solution of benzoic anhydride (14.7 g, 0.12 mol) in dimethylformamide (200 mL). The solution was stirred at 25° C. for 48 h and then evaporated to dryness under reduced pressure. The residue was triturated with methanol (2×200 mL), collected and then triturated with warm ether (300 mL) for 10 min. The solid was collected and triturated with hot 2-propanol (50 mL) and allowed to stand at 4° C. for 16 h. The solid was collected and dried to give 17 g of product. The crude filtrate residue (18 g) of 2'-O-methylcytidine was treated with benzoic anhydride (17.3 g, 0.076 mol) in dimethylformamide (250 mL) as above and triturated in a similar fashion to give an additional 6.7 g of pure product for a total yield of 23.7 g (16% from cytidine) of solid; TLC homogenous (Rf 0.25, chloroform-methanol 5:1, cospots with material produced from the other route.)

N$^4$-Benzoyl-5'-O-(4,4'-dimethoxytriphenylmethyl)-2'-O-methylcytidine

N$^4$-Benzoyl-2'-O-methylcytidine (28 g, 0.077 mol) was evaporated under reduced pressure to an oil with pyridine (400 mL). To the residue was added 4,4'-dimethoxytriphenylmethyl chloride (DMT-Cl, 28.8 g, 0.085 mol) and pyridine (400 mL). The mixture was stirred at 25° C. for 2 h and then quenched by the addition of methanol (10 mL) for 30 min. The mixture was concentrated under reduced pressure and the residue was chromatographed on silica gel (500 g, hexanes-ethyl acetate-triethylamine 60:40:1 and then ethyl acetate-triethylamine 99:1). The appropriate fractions were combined, evaporated under reduced pressure and dried at 40° C./0.2 mmHg for 2 h to give 26 g (74%, 16% from cytidine) of foam; TLC homogenous (Rf 0.45, ethyl acetate); PMR (DMSO) δ 11.3 (H-N$^4$), 8.4–6.9 (H-6, H-5, Bz), 5.95 (H-2'), 5.2 (HO-3'), 3.7 (s, 6, CH$_3$O—trit.), 3.5 (s, 3, CH$_3$O-2').

[N$^4$-Benzoyl-5'-O-(4,4'-dimethoxytriphenylmethyl)-2'-O-methylcytidin-3'-O-yl]-N,N-diisopropylaminocyanoethoxyphosphoramidite The product was prepared in the same manner as the adenosine analog above by starting with intermediate N$^4$-benzoyl-5'-O-(4,4'-dimethoxytriphenylmethyl)-2'-O-methylcytidine and using ethyl acetate-hexanes-triethylamine 59:40:1 as the chromatography eluent to give the product as a solid foam in 71% yield (11 from cytidine); TLC homogenous diastereomers (Rf 0.46; 0.33, ethyl acetate-hexanes-triethylamine 59:40:1); $^{31}$P-NMR (CD$_3$CN, H$_3$PO$_4$ std.) δ 150.34; 151.02 (diastereomers).

D. 2'-Deoxy-2'-octadecyl-5'-O-(4,4'-dimethoxytrityl)-guanosine-3'-O-(N,N-diisopropyl-β-cyanoethylphosphoramidite).

2,6-Diamino-9-(2-O-octadecyl-β-D-ribofuranosyl)purine 2,6-Diamino-9-(β-D-ribofuranosyl)purine (50 g, 180 mmol) and sodium hydride (7 g) in DMF (1 L) were heated to boiling for 2 hr. Iodooctadecane (100 g) was added at 150° C. and the reaction mixture allowed to cool to RT. The reaction mixture was stirred for 11 days at RT. The solvent was evaporated and the residue purified by silica gel chromatography. The product was eluted with 5% MeOH/CH$_2$Cl$_2$. The appropriate fractions were evaporated to yield the product (11 g). $^1$H NMR (DMSO-d$_6$) δ 0.84 (t, 3, CH$_2$), 1.22 (m, 32, O—CH$_2$—CH$_2$—(CH$_2$)$_{16}$), 1.86 (m, 2, O—CH$_2$CH$_2$), 3.25 (m, 2, O—CH$_2$), 3.93 (d, 1, 4'H), 4.25 (m, 1, 3'H), 4.38 (t, 1, 2' H), 5.08 (d, 1, 3'-OH), 5.48 (t, 1, 5'-OH, 5.75 (s, 2, 6-NH$_2$), 5.84 (d, 1, 1'-H), 6.8 (s, 2, 2-NH$_2$), and 7.95 (s, 1, 8-H).

2'-O-Octadecylguanosine 2,6-Diamino-9-(2-O-octadecyl-β-D-ribofuranosyl)purine (10 g) in 0.1M sodium phosphate buffer (50 ml, pH 7.4), 0.1M tris buffer (1000 ml, pH 7.4) and DMSO (1000 ml) was treated with adenosine deaminase (1.5 g) at RT. At day 3, day 5 and day 7 an additional aliquot (500 mg, 880 mg and 200 mg, respectively) of adenosine deaminase was added. The reaction was stirred for a total of 9 day and purification by silica gel chromatography yielded the product (2 g). An analytical sample was recrystallized from MeOH. $^1$H NMR (DMSO-d$_6$) δ 0.84 (t, 3, CH$_3$), 1.22 (s, 32, O—CH$_2$—CH$_2$—(CH$_2$)$_{16}$), 5.07 (m, 2, 3'-OH and 5'-OH), 5.78 (d, 1, 1'H), 6.43 (s, 2, NH$_2$), 7.97 (s, 1, 8H) and 10.64 (s, 1, NH$_2$). Anal. Calcd. for C$_{28}$H$_{49}$N$_5$O$_5$: C, 62.80; H, 9.16; N, 12.95. Found: C, 62.54; H, 9.18; N, 12.95.

N$^2$-Isobutyryl-2'-O-octadecylquanosine

2'-O-Octadecylguanosine (1.9 g) inpyridine (150 ml) was cooled in an ice bath, and treated with trimethylsilyl chloride (2 g, 5 eq) and isobutyryl chloride (2 g, 5 eq). The reaction mixture was stirred for 4 hours, during which time it was allowed to warm to room temperature. The solution was cooled, water added (10 mL) and stirred for an additional 30 minutes. Concentrated ammonium hydroxide (10 mL) was added and the solution concentrated in vacuo. The residue was purified by silica gel chromatography (eluted with 3% MeOH/EtOAc) to yield 1.2 g of product. $^1$H NMR (DMSO-$d_6$) δ 0.85 (t, 3, $CH_3$), 1.15 (m, 38, O—$CH_2CH_2(CH_2)_{16}$ and $CH(CH_3)_2$), 2.77 (m, 1, $CH(CH_3)_2$), 4.25 (m, 2, 2'H, 3'H), 5.08 (t, 1, 5'-OH), 5.12 (d, 1, 3'-OH), 5.87 (d, 1, 1'-H), 8.27 (s, 1, 8-H), 11.68 (s, 1, $NH_2$) and 12.08 (s, 1, $NH_2$). Anal. Calcd. for $C_{32}H_{55}N_5O_6$: C, 63.47; H, 9.09; N, 11.57. Found: C, 63.53; H, 9.20; N, 11.52.

$N^2$-Isobutyryl-5'-dimethoxytrityl-2'-O-octadecylquanosine $N^2$-Isobutyryl-2'-O-octadecylguanosine was converted to the $N^2$-isobutyryl-5'-dimethoxytrityl-2'-O-octadecylguanosine as per the procedure for adenosine above.

[$N^2$-Isobutyryl-5'-dimethoxytrityl-2'-O-octadecylquan-3'-O-yl]-N,N-diisopropylamino-cyanothoxyphosphoramidite The product was prepared in the same manner as the adenosine analog above by starting with intermediate $N^2$-isobutyryl-5'-dimethoxytrityl-2'-O-octadecylguanosine.

2'-O-[(N-phthalimido)prop-3-yl]adenosine

The title compound was prepared as per the 2'-O-nonyladenosine procedure using N-(3-bromopropyl) phthalimide. Chromatography on silica gel give a white solid, m.p. 123°–124° C. Analysis for: $C_{21}H_{22}N_6O_6$. Calculated: C, 55.03; H, 4.88; N, 18.49. Found: C, 55.38; H, 4.85; N, 18.46.

2'-O-[(N-phthalmido)prop-3-yl]-$N^6$-benzoyladenosine

Benzoylation of 2'-O-[(N-phthalimido)prop-3-yl] adenosine as per the 2'-O-nonyladenosine procedure above give the title compound. Analysis for: $C_{28}H_{26}N_6O_7$. Calculated: C, 60.21; H, 4.69; N, 15.05. Found: C, 59.94; H, 4.66; N, 14.76.

2'-O-[(N-phthalimido)prop-3-yl]-5'-O-dimethoxytrityl-$N^6$-benzoyladenosine

The title compound was prepared from 2'-O-[(N-phthalimido)prop-3-yl]-$N^6$-benzoyladenosine as per the 2'-O-nonyladenosine above. Analysis for: $C_{49}H_{44}N_6O_9$. Calculated: C, 68.36; H, 5.15; N, 9.76. Found: C, 68.16; H, 5.03; N, 9.43.

$N_6$-benzoyl-5'-O-dimethoxytrityl-2'-O-[(N-phthalimido) prop-3-yl]adenosine-3'-O,N,N-diiscpropyl-β-cyanoethylphosphoramidite The title compound was prepared from 2'-O-[(N-phthalimido)prop-3-yl] -5'-O-dimethoxytrityl-$N^6$-benzoyladenosine as above for the 2'-O-nonyladenosine compound. A white foam was obtained.

F. $N^6$-Benzoyl-2'-[(imidazol-1-yl)butyl-4-yl]5'O-(4,4' dimethoxytrityl)]adenosine3'-O(N,N-diisopropyl-β-cyanoethylphosphoramidite).

2'-O-[imidizo-1-yl-(but-4-yl)]adenosine

The title compound can be prepared as per the 2'-O-nonyladenosine procedure using 1-(4-bromobutyl)imidazole in place of 1-bromononane.

2'-O-[(imidizol-1-yl)but-4-yl]-$N^6$-benzoyladenosine

Benoylation of 2'-O-[(imidizol-1-yl)but-4-yl)]adenosine as per the 2'-O-nonyladenosine procedure above will give the title compound.

2'-O-[(imidizol-1-yl)but-4-yl]-5'-O-dimethoxytrityl-$N^6$-benzoyladenosine

The title compcund can be prepared from 2'-O-[(imidizol-1-yl)but-4-yl]adenosine as per the 2'-O-nonyladenosine procedure above.

$N^6$-benzoyl-5'-O-dimethoxytrityl-2'-O-[(imidizol-1-yl)but-4-yl]adenosine-3'-O,N,N-diisdpropyl-β-cyanoethyl phosphoramidite The title compcund can be prepared from 2'-O-[(imidizol-1-yl)but-4-yl)]-5'-O-dimethoxytrityl-$N^6$-benzoyladenosine as per the 2'-O-nonyladenosine procedure above.

EXAMPLE 6

Preparation of 2'-Deoxy-2'-(vinyloxy) Modified Oligonucleotides.

The requisite 2'-deoxy-2'-O-vinyl ribosides of nucleic acid bases A, G, U(T), and C are prepared by modifications of literature procedures described by Sproat et al. [*Nucleic Acids Research*, 18, 41 (1990)] and Inoue et al. [*Nucleic Acids Research*, 15, 6131 (1987)]. In this case 1,2-dibromoethane is coupled to the 2'-hydroxyl and subsequent dehydrobromination affords the desired blocked 2'-vinyl nucleoside. Standard procedures, as described in Example 1A, are employed to prepare the 5'-DMT and 3'-phosphoramidites as listed below.

A. $N^6$-Benzoyl-[2'-deoxy-2'-(vinyloxy)-5'-O-(4,4'-dimethoxytrityl)]adenosine-3'-O-(N,N-diisopropyl-β-cyanoethylphosphoramidite).

B. 2'-Deoxy-2'-(vinyloxy)-5'-O-(4,4'-dimethoxytrityl)-uridine-3'-O-(N,N-diisopropyl-β-cyanoethylphosphoramidite).

C. 2'-Deoxy-2'-(vinyloxy)-5'-O-(4,4'-dimethoxytrityl)-cytidine-3'-O-(N,N-diisopropyl-β-cyanoethylphosphoramidite).

D. 2'-Deoxy-2-(vinyloxy)-5'-O-(4,4'-dimethoxytrityl)-guanosine-3'-O-(N,N-diisopropyl-β-cyanoethylphosphoramidite).

EXAMPLE 7

Preparation of 2'-Deoxy-2'-(allyloxy) Modified Oligonucleotides.

The requisite 2'-deoxy-2'-O-allyl ribosides of nucleic acid bases A, G, U(T), and C are prepared by modifications of literature procedures described by Sproat et al. [*Nucleic Acids Research*, 18, 41 (1990)] and Inoue et al. [*Nucleic Acids Research*, 15, 6131 (1987)]. Standard procedures, as described in Example 1A, are employed to prepare the 5'-DMT and 3'-phosphoramidites as listed below.

A. $N^6$-Benzoyl-[2'-deoxy-2'-(allyloxy)-5'-O-(4,4'-dimethoxytrityl)]adenosine-3'-O-(N,N-diisopropyl-β-cyanoethylphosphoramidite).

B. 2'-Deoxy-2'-(allyloxy)-5'-O-(4,4'-dimethoxytrityl)-uridine-3'-O-(N,N-diisopropyl-O-cyanoethylphosphoramidite).

C. 2'-Deoxy-2'-(allyloxy)-5'-O-(4,4'-dimethoxytrityl)-cytidine-3'-O-(N,N-diisopropyl-β-cyanoethylphosphoramidite).

D. 2'-Deoxy-2'-(allyloxy)-5'-O-(4,4'-dimethoxytrityl)-guanosine-3'-O-(N,N-diisopropyl-β-cyanoethylphosphoramidite).

EXAMPLE 8

Preparation of 2'-deoxy-2'-(methylthio), (methylsulfinyl) and (methylsulfonyl) modified oligonucleotides.

A. 2'-Deoxy-2'-methylthiouridine. 2,2' Anhydrouridine (15.5 g, 68.2 mmol) [Rao and Reese, *J. Chem. Soc., Chem. Commun.*, 997], methanethiol (15.7 g, 327 mmol), 1,1,3,3-tetramethylguanidine (39.2 g, 341 mmol) and DMF (150 mL) were heated at 60° C. After 12 hours, the reaction mixture was cooled and concentrated under reduced pressure. The residual oil was purified by flash column chromatography on silica gel (300 g). Concentration of the appropriate fractions, which were eluted with $CH_2Cl_2$-MeOH (9:1), and drying the residue under reduced pressure gave 2'-deoxy-2'-methylthiouridine as a pale yellow solid (14.11 g, 75.4%). Attempts to crystallize the solids from EtOH-hexanes [as reported by Imazawa et al., Chem. Pharm. Bull., 23, 604 (1975)] failed and the material turned into a hygroscopic foam.

$^1$H NMR (DMSO-$d_6$) δ 2.0 (3H, s, $SCH_3$), 3.34 (1H, dd, $J_{3',2'}$=5.4 Hz, 2' H), 3.59 (2H, br m, 5' $CH_2$), 3.84 (1H, m, 4' H), 4.2 (1H, dd, $J_{3',4'}$=2.2 Hz, 3' H), 5.15 (1H, t, 5' OH), 5.62 (1H, t, 3' OH), 5.64 (1H, d, $J_{C6,C5}$=8.2 Hz), 6.02 (1H, d, $J_{1',2'}$=6 Hz, 1'H), 7.82 (1H, d, $J_{C5,C6}$=8.2 Hz, C6H), 11.38 (1H, br s, NH).

B. 2,2'-Anhydro-5-methyluridine.

A mixture of 5-methyluridine (16.77 g, 69.2 mmol), diphenyl carbonate (17.8 g. 83.1 mmol) and $NaHCO_3$ (100 mg) in hexamethylphosphoramide (175 mL) was heated to 150° C. with stirring until evolution of $CO_2$ ceased (approximately 1 hour). The reaction mixture was cooled and then poured into diethyl ether (1 L) while stirring to furnish a brown gum. Repeated washings with diethyl ether (4×250 mL) furnished a straw-colored hygroscopic powder. The solid was purified by short column chromatography on silica gel (400 g). Pooling and concentrating appropriate fraction, which were eluted with $CH_2Cl_2$-MeOH (85:15), furnished the title compound as a straw-colored solid (12 g, 77.3%), which crystallized from EtOH as long needles, m.p. 226°–227° C.

C. 2'-Deoxy-2'-methylthio-5-methyluridine.

2,2'-Anhydro-5-methyluridine (17.02 g, 70.6 mmol), methanethiol (16.3 g, 339 mmol), 1,1,3,3-tetramethylguanidine (40.6 g, 353 mmol) and DMF (150 mL) were heated at 60° C. After 12 hours, the products were cooled and concentrated under reduced pressure. The residual oil was purified by short silica gel column chromatography (300 g). Pooling and concentrating appropriate fractions, which were eluted with $CH_2Cl_2$-MeOH (93:7), furnished the title compound as a white foam (15.08 g, 74.1%), which was crystallized from EtOH-$CH_2Cl_2$ as white needles.

D. 2'-Deoxy-2'-methylsulfinyluridine.

To a stirred solution of 2'-deoxy-2'-methylthiouridine (1 g, 3.65 mmol) in EtOH (50 mL) was added a solution of m-chloroperbenzoic acid (50%, 1.26 g, 3.65 mmol) in EtOH (50 mL) over a period of 45 minutes at 0° C. the solyent was removed under reduced pressure and the residue purified by short silica gel (30 g) column chromatography. Concentration of the appropriate fractions, which were eluted with $CH_2Cl_2$-MeOH (75:25), afforded the title compound as a white solid (0.65 g, 61.4%). Crystallization from EtOH furnished white granules, m.p. 219°–221° C.

$^1$H NMR (DMSO-$d_6$) δ 2.5 (3H, s, $SOCH_3$), 3.56 (2H, br s, 5' $CH_2$), 3.8 (1H, m, 4' H), 3.91 (1H, m, 2' H), 4.57 (1H, m, 3' H), 5.2 (1H, br s, 5' OH), 5.75 (1H, d, $C_5H$), 6.19 (1H, d, 3' OH), 6.35 (1H, d, 1' H), 7.88 (1H, d, $C_6H$), 11.43 (1H, br s, NH).

E. 2'-Deoxy-2'-methylsulfonyluridine.

To a stirred solution of 2'-deoxy-2'-methyluridine (1 g, 3.65 mmol) in EtOH (50 mL) was added a solution of m-chloroperbenzoic acid (50%, 3.27 g, 14.6 mmol) in one portion at room temperature. After 2 hours, the solution was filtered to separate the white precipitate which was formed, which upon washing (2×20 mL EtOH and 2×20 mL diethyl ether) and drying, furnished the title compound as a fine powder (0.76 g, 68%), m.p. 227°–228° C.

$^1$H NMR (DMSO-$d_6$) δ 3.1 (3H, s, $SO_2CH_3$), 3.58 (2H, m, 5' $CH_2$), 3.95 (1H, m, 2' H), 3.98 (1H, m, 4' H), 4.5 (1H, br s, 3' H), 5.2 (1H, br s, 5' OH), 5.75 (1H, d, $C_5H$), 6.25 (1H, d, 3' OH), 6.5 (1H, d, 1' H), 7.8 (1H, d, $C_6H$), 11.45 (1H, br s, NH).

F. 2'-Deoxy-5'-O-(4,4'-dimethoxytrityl)-2'-methylthiouridirLe.

To a stirred solution of 2'-deoxy-2'-methylthiouridine (1.09 g, 4 mmol) in dry pyridine (10 mL) was added 4,4'-dimethoxytritylchloride (1.69 g, 5 mmol) and 4-dimethylaminopyridine (50 mg) at room temperature. The solution was stirred for 12 hours and the reaction mixture quenched by adding MeOH (1 mL). The reaction mixture was concentrated under reduced pressure and the residue was dissolved in $CH_2Cl_2$ (100 mL), washed with saturated aqueous $NaHCO_3$ (2×50 mL) and saturated aqueous NaCl (2×50 mL), and dried with $MgSO_4$. The solution was concentrated under reduced pressure and the residue purified by silica gel (30 g) column chromatography. Elution with $CH_2Cl_2$-MeOH-triethylamine (89:1:1) furnished the title compound as a homogenous material. Pooling and concentrating the appropriate fractions furnished the 5'-O-DMT nucleoside as a foam (1.5 g, 66.5%).

$^1$H NMR (DMSO-$d_6$) δ 2.02 (3H, s, $SCH_3$), 3.15–3.55 (1H, m, 2' CH), 3.75 (6H, s, 2 $OCH_3$), 3.97 (1H, m, 4' H), 4.24 (1H, m, 3' H), 5.48 (1H, d, $C_5H$), 5.73 (1H, d, 3' OH), 6.03 (1H, d, C1' H), 6.82–7.4 (13H, m, ArH), 6.65 (1H, d, $C_6H$), 11.4 (1H, br s, NH).

G. 2'-Deoxy-3'-O-[(N,N-diisopropyl)-O-β-cyanoethylphosphoramide]-5'-O-(4,4'-dimethoxytrityl)-2'-methylthiouridine.

To a stirred solution of 2'-deoxy-5'-O-(4,4'-dimethoxytrityl)-2'-methylthiouridine (1.5 g, 2.67 mmol) in dry THF (25 mL) was added diisopropylethylamine (1.4 mL, 8 mmol) and the solution was cooled to 0° C. N,N,-Diisopropyl-β-cyanoethylphosphoramidic chloride (1.26 mL, 5.34 mmol) was added dropwise over a period of 15 minutes. The reaction mixture was then stirred at room temperature for 2 hours. Ethyl acetate (100 mL, containing 1% triethylamine) was added and the solution washed with saturated NaCl (2×50 mL) and the organic layer dried over $MgSO_4$. The solyent was removed under reduced pressure and the residue purified by short silica gel (30 g) column chromatography. Elution with $CH_2Cl_2$-MeOH-triethylamine (98:1:1) furnished the product as a mixture of diastereomers. Evaporation of the appropriate fractions provided the title compound as a foam (1.32 g, 64.7%).

$^1$H NMR ($CDCl_3$) δ 2.0 and 2.02 (3H, s, $SCH_3$), 5.3 and 5.35 (1H, 2d, $C_5H$), 6.23 (1H, d, 1'H), 7.8 and 7.88 (1H, 2d, $C_6H$) and other protons.

$^{31}$P NMR ($CDCl_3$) δ 151.68 and 152.2 ppm.

H. 2'-Deoxy-3',5'-di-O-acetyl-2'-methylthiouridine.

2'-Deoxy-2'-methylthiouridine (5.0 g, 18.24 mmol) and acetic anhydride (5.6 mL, 54.74 mmol) were stirred in dry pyridine (30 mL) at room temperature for 12 hours. The products were then concentrated under reduced pressure and the residue obtained was purified by short silica gel column chromatography. The appropriate fractions, which were eluted with $CH_2Cl_2$-MeOH (9:1), were combined, evaporated under reduced pressure and the residue crystallized from EtOH to give the title compound (6.0 g, 91.8%) as white needles, m.p. 132° C.

$^1$H NMR ($CDCl_3$) δ 2.17 (3H, s, $SCH_3$), 2.20 (6H, s, 2 $COCH_3$), 3.40 (1H, t, 2'H), 4.31–4.40 (3H, m, 4',5'H), 5.31 (1H, m, 3'H), 5.80 (1H, d, $C_5H$), 6.11 (1H, d, 1' H), 7.45 (1H, d, $C_6H$), 8.7 (1H, br s, NH).

I. 2'-Deoxy-3',5'-di-O-acetyl-4-(1,2,4-triazol-yl)-2'-methylthiouridine.

Triethylamine (8.4 mL, 60.3 mmol) and phosphoryl chloride (1.2 mL, 12.9 mmol) were added to a stirred solution of 2'-deoxy-3',5'-di-O-acetyl-2'-methylthiouridine (4.6 g, 13 mmol) in MeCN (50 mL). 1,2,4-Triazole (4.14 g, 59.9 mmol) was then added and the reactants were stirred at room temperature. After 16 hours, triethylamine-$H_2O$ (6:1, 20 mL) was added, followed by saturated aqueous $NaHCO_3$ (100 mL), and the resulting mixture was extracted with $CH_2Cl_2$ (2×100 mL). The organic layer was dried with $MgSO_4$ and evaporated under reduced pressure. The residue was purified by short silica gel column chromatography. The appropriate fractions, which were eluted with $CH_2Cl_2$-MeOH (9:1), were evaporated under reduced pressure and the residue was crystallized from EtOH to give the title compound (3.01 g, 56.4%) as needles, m.p. 127°–130° C.

$^1$H NMR (CDCl$_3$) δ 2.18 (6H, s, 2 COCH$_3$), 2.30 (3H, s, SCH$_3$), 3.67 (1H, m, 2'H), 4.38–4.50 (3H, m, 4',5'H), 5.17 (1H, t, 3'H), 6.21 (1H, d, 1'H), 7.08 (1H, d, C$_5$H), 8.16 (1H, s, CH), 8.33 (1H, d, C$_6$H), 9.25 (1H, s, NH).

J. 2'-Deoxy-2'-methylthiocytidine.

2'-Deoxy-3',5'-di-O-acetyl-4-(1,2,4-triazol-1-yl)-2'-methylthiouridine (3.0 g, 7.5 mmol) was dissolved in a saturated solution of ammonia in MeOH (70 mL) and the solution was stirred at room temperature in a pressure bottle for 3 days. The products were then concentrated under reduced pressure and the residue was crystallized from EtOH-$CH_2Cl_2$ to give the title compound (1.06 g, 51.7%) as crystals, m.p. 201° C.

$^1$H NMR (DMSO-d$_6$) δ 1.95 (3H, s, SCH$_3$), 3.36 (1H, m, 2'H), 3.55 (2H, m, 5'CH$_2$), 3.82 (1H, m, 4' H), 4.18 (1H, dd, 3'H), 5.75 (1H, d, C$_5$H), 6.1 (1H, d, 1'H), 7.77 (1H, d, C$_6$H).

Anal calcd. for $C_{10}H_{15}N_3O_4S$: C, 43.94; H, 5.53; N, 15.37: S, 11.73. Found: C, 44.07; H, 5.45; N, 15.47; S, 11.80.

K. 2'-Deoxy-N$^4$-benzoyl-2'-methylthiocytidine.

To a stirred solution of 2'-deoxy-2'-methylthiocytidine (0.86 g, 3.15 mmol) in dry pyridine (20 mL) was added trimethylchlorosilane (2 mL, 15.75 mmol), and stirring continued for 15 minutes. Benzoyl chloride (2.18 mL, 18.9 mmol) was added to the solution followed by stirring for 2 hours. The mixture was then cooled in an ice bath and MeOH (10 mL) was added. After 5 minutes, ammonium hydroxide (30% aq., 20 mL) was added and the mixture stirred for 30 minutes. The reaction mixture was then concentrated under reduced pressure and the residue purified by short silica gel (70 g) column chromatography. Elution with $CH_2Cl_2$-MeOH (9:1), pooling of the appropriate fractions and evaporation furnished the title compound (0.55 g, 46.6%), which crystallized from EtOH as needles, m.p. 193°–194° C.

L. N$^4$-Benzoylamino-1-[2'-deoxy-5'-(4,4'-dimethoxytrityl)-2-methylthio-β-D-ribofuranosyl]pyrimidin-3(2H)-one or 2'-deoxy-N$^4$-benzoyl-5'-(4,4'-dimethoxytrityl)-2'-methylthiocytidine).

To a stirred solution of 2'-deoxy-N$^4$-benzoyl-2'-methylthiocytidine (0.80 g, 2.12 mmol) in dry pyridine (10 mL) was added 4,4'-dimethoxytrityl chloride (1.16 g, 3.41 mmol) and DMAP (10 mg) at room temperature. The solution was stirred for 2 hours and the product concentrated under reduced pressure. The residue was dissolved in $CH_2Cl_2$ (70 mL), washed with saturated $NaHCO_3$ (50 mL), saturated NaCl (2×50 mL), dried with $MgSO_4$ and evaporated under reduced pressure. The residue was purified by short silica gel (50 g) column chromatography. Elution with $CH_2Cl_2$-triethylamine (99:1), pooling and concentrating the appropriate fractions furnished the title compound (1.29 g, 90%) as a white foam. $^1$H NMR (DMSO-d,) δ 2.1 (3H, s, SCH$_3$), 3.5 (1H, m, 2'H), 3.75 (6H, s, OCH$_3$), 4.15 (1H, m, 4' H), 4.4 (1H, t, 3'H), 5.74 (1H, br d, 3'OH), 6.15 (1H, d, C1H), 6.8–8.0 (25H, m, ArH and C$_5$H), 8.24 (1H, d, C$_6$H), 11.3 (1H, br s, NH).

M. 2'-Deoxy-N$^4$-Benzoyl-3-O-[(N,N-diisopropyl)-β-cyanoethylphosphoramide]-5'-O-(4,4'-dimethoxytrityl)-2'-methylthiocytidine).

2'-Deoxy-N$^4$-benzoyl-5'-(4,4'-dimethoxytrityl)-2'-methylthiocytidine (1.41 g, 2.07 mmol) was treated with diisopropylethylamine (1.4 mL, 8 mmol) and N,N-diisopropyl-β-cyanoethylphosphoramide chloride (1.26 mL, 5.34 mmol) in dry THF (25 mL) as described in Example 8-G above. The crude product was purified by short silica gel (50 g) column chromatography using $CH_2Cl_2$-hexanes-triethylamine (89:10:1) as the eluent. The appropriate fractions were pooled and evaporated under reduced pressure to give the title compound (1.30 g, 71%) as a white foam (mixture of diastereoisomers).

$^1$H NMR (CDCl$_3$) δ 2.31 (3H, s, SCH$_3$), 3.45–3.7 (3H, m, 2'H and 5'CH$_2$), 3.83 (6H, m, OCH$_3$), 4.27–4.35 (1H, m, 4'H) 4.6–4.8 (1H, m, 3'H), 6.35 (1H, 2d, 1'H), 6.82–7.8 (25H, m, ArH and C$_5$H), 8.38 and 8.45 (1H, 2d, C$_6$H) and other protons.

$^{31}$P NMR δ 151.03 and 151.08 ppm.

N. 2'-Deoxy-2'-methylsulfinylcytidine.

2'-Deoxy-2'-methylthiocytidine of Example 8-J was treated as per the procedure of Example 8-D to yield the title compound as a mixture of diastereoisomers having a complex $^1$H NMR spectrum.

O. 2'-Deoxy-2'-methylsulfonylcytidine.

2'-Deoxy-2'-methylthiocytidine of Example 8-J was treated as per the procedure of Example 8-E to yield the title compound.

P. N$^6$-Benzoyl-3',5'-di-O-[Tetrahydropyran-2-yl]-2'-deoxy-2'-methylthioadenosine.

N$^6$-Benzoyl-9-[2'-O-trifluoromethylsulfonyl-3',5'-di-O-(tetrahydropyran-2-yl)-β-D-arabinofuranosyl]adenine from Example 1-D is prepared by treatment with methanethiol in the presence of tetramethylguanidine to yield the title compound.

Q. N$^6$-Benzoyl-2'-deoxy-2'-methylthioadenosine.

N$^6$-Benzoyl-3',5'-di-O-(tetrahydropyran-2-yl)-β-D-arabinofuranosyl]adenosine from Example 8-P is treated as per Example 1-F to yield the title compound.

R. N6-Benzoyl-2'-deoxy-2'-methylsulfinyladenosine.

N$^6$-Benzoyl-2'-deoxy-2'methylthioadenosine from Example 8-Q is treated as per the procedure of Example 8-D to yield the title compound.

S. N$^6$-Benzoyl-2'-deoxy-2'-methylsulfonyladenosine.

N$^6$-Benzoyl-2'-deoxy-2'methylthioadenosine from Example 8-Q is treated as per the procedure of Example 8-E to yield the title compound.

T. N$^2$-Isobutyryl-3',5'-di-O-(tetrahydropyran-2-yl)-2'-deoxy-2'-methylthioguanosine.

N$^2$-Isobutyryl-9-(3',5'-di-O-[tetrahydropyran-2-yl]-2'-O-trifluoromethylsulfonyl-β-D-arabinofuranosyl)guanine from Example 1-P is treated with methanethiol in the presence of 1,1,3,3-tetramethylguanidine to yield the title compound.

U. N$^2$-Isobutyryl-2'-deoxy-2'-methylthioguanosine.

N$^2$-Isobutyryl-3',5'-di-O-(tetrahydropyran-2-yl)-2'-deoxy-2'-methylthioguanosine is treated as per the procedure of Example 1-R to yield the title compound.

V. N$^2$-Isobutyryl-2'-deoxy-2'-methylsulfinylguanosine.

N$^2$-Isobutyryl-2'-deoxy-2'-methylthioguanosine from Example 8-U is treated as per the procedure of Example 8-D to yield the title compound.

W. N$^2$-Isobutyryl-2'-deoxy-2'-methylsulfonylguanosine.

N$^2$-Isobutyryl-2'-deoxy-2'-methylthioguanosine from Example 8-U is treated as per the procedure of Example 8-E to yield the title compound.

X. 2'-Deoxy-5'-O-(4,4'-dimethoxytrityl)-2'-methylsulfinyluridine.

2'-Deoxy-2'-methylsulfinyluridine from Example 8-D above is treated as per the procedure of Example 8-F to yield the title compound.

Y. 2'-Deoxy-3'-O-[(N,N-diisopropyl)-O-β-cyanoethylphosphoramide]-5'-(4,4'-dimethoxytrityl)-2'-methylsulfinyluridine.

2'-Deoxy-5'-O-(4,4'-dimethoxytrityl)-2'-methylsulfinyluridine is treated as per the procedure of Example 8-G to yield the title compound.

Z. $N^6$Benzoyl-2'-deoxy-5'-O-(4,4'-dimethoxytrityl)-2'-methylthioadenosine.

$N^6$-Benzoyl-2'-deoxy-2'-methylthioadenosine from Example 8-Q above is treated as per the procedure of Example 8-F to yield the title compound.

AA. $N^6$ Benzoyl-2'-deoxy-3'-O-[(N,N-diisopropyl)-O-β-cyanoethylphosphoramide]-5'-O-(4,4'-dimethoxytrityl)-2'-methylthioadenosine.

$N^6$-Benzoyl-2'-deoxy-5'-O-(4,4'-dimethoxytrityl)-2'-methylthioadenosine is treated as per the procedure of Example 8-G to yield the title compound.

BB. 2'-Deoxy-$N^2$-isobutyryl-5'-O-(4,4'-dimethoxytrityL)-2'-methylthioadenosine.

2'-Deoxy-$N^2$-isobutyryl-2'-methylthioguanosine from Example 8-U above is treated as per the procedure of Example 8-F to yield the title compound.

CC. 2'-Deoxy-$N^2$ -isobutyryl-3'-O-[(N,N-diisopropyl)-O-β-cyanoethylphosphoramide-5'-O-(4,4'-dimethoxytrityl-2'-methylthioguanosine.

2'-Deoxy-$N^2$-isobutyryl-5'-O-(4,4'-dimethoxytrityl)-2'-methylthioguanosine is treated as per the procedure of Example 8-G to yield the title compound.

DD. 2'-Deoxy-5'-O-(4,4'-dimethoxytrityl-2'-methylsulfonyluridine.

2'-Deoxy-2'-methylsulfonyluridine from Example 8-E above is treated as per the procedure of Example 8-F to yield the title compound.

EE. 2'-Deoxy-3'-O-[(N,N-diisopropyl)-O-β-cyanoethylphosphoramide]-5'-O-(4,4'-dimethoxytrityl-2'-methyl sulfinyluridine.

2'-Deoxy-5'-O-(4,4'dimethoxytrityl)-2'-methylsulfinyluridine is treated as per the procedure of Example 8-G to yield the title compound.

EXAMPLE 9

Chemical conversion of an thymine or cytosine (pyrimidine type base) to its β-D-2'-deoxy-2'-substituted erythropentofuranosyl nucleoside; 2'-substituted ribosylation).

The thymine or cytosine type analogs are trimethylsilylated under standard conditions such as hexamethyldisilazane (HMDS) and an acid catalyst (ie. ammonium chloride) and then treated with 3,5-O-ditoluoyl-2-deoxy-2-substituted-α-D-erythropentofuranosyl chloride in the presence of Lewis acid catalysts (i.e. stannic chloride, iodine, boron tetrafluoroborate, etc.). A specific procedure has recently been described by Freskos [*Nucleosides & Nucleotides*, 8, 1075 (1989)] in which copper (I) iodide is the catalyst employed.

EXAMPLE 10

Chemical conversion of an adenine or guanine (purine type base) to its β-D-2'-deoxy-2'-substituted erythropentofuranosyl nucleoside; 2'-substituted ribosylation).

The protected purine type analogs are converted to their sodium salts via sodium hydride in acetonitrile and are then treated with 3,5-O-ditoluoyl-2-deoxy-2-substituted-α-D-erythro-pentofuranosyl chloride at ambient temperature. A specific procedure has recently been described by Robins et al. [*Journal of American Chemical Society*, 106, 6379 (1984)].

EXAMPLE 11

Conversion of 2'-deoxy-2-substituted thymidines to the corresponding 2'-deoxy-2'-substituted cytidines (chemical conversion of an pyrimidine type 4-keto group to an 4-amino group).

The 3' and 5' sugar hydroxyls of the 2'modified nucleoside types are protected by acyl groups such as toluoyl, benzoyl, p-nitrobenzoyl, acetyl, isobutryl, trifluoroacetyl, etc. under standards conditions using acid chlorides or anhydrides, pyridine as the solyent and dimethylaminopyridine as a catalyst. The protected nucleoside is next chlorinated with thionyl chloride or phosphoryl chloride in pyridine or another appropriate basic solyent. The 4-chloro group is then displaced with ammonia in methanol. Deprotection of the sugar hydroxyls also takes place. The amino group is benzoylated and the acyl groups are selectively removed by aqueous sodium hydroxide solution. Alternatively, the in situ process of first treating the nucleoside with chlorotrimethylsilane and base to protect the sugar hydroxyls from subsequent acylation may be employed. [Ogilyie, *Can J. Chem.*, 67, 831 (1989)]. Another conversion approach is to replace the 4-chloro group with a 1,2,4-triazolo group which remains intact throughout the oligonucleotide synthesis on the automated synthesizer and is displaced by ammonia during treatment with ammonium hydroxide which cleaves the oligonucleotide from the CPG support and effects deprotection of the heterocycle. Furthermore, in many cases the 4-chloro group can be utilized as described and replaced at the end of oligonucleotide synthesis.

EXAMPLE 12

Procedure for the attachment of 2'-deoxy-2'-substituted 5'-dimethoxytriphenylmethyl ribonucleosides to the 5'-hydroxyl of nucleosides bound to CPG support.

The 2'-deoxy-2'-substituted nucleoside that will reside at the terminal 3'-position of the oligonucleotide is protected as a 5'-DMT group (the cytosine and adenine exocyclic amino groups are benzoylated and the guanine amino is isobutrylated) and treated with trifluoroacetic acid/ bromoacetic acid mixed anhydride in pyridine and dimethylaminopyridine at 50° C. for five hours. The solution is then evaporated under reduced pressure to a thin syrup which is dissolved in ethyl acetate and passed through a column of silica gel. The homogenous fractions are collected and evaporated to dryness. A solution of 10 mL of acetonitrile, 10 μM of the 3'-O-bromomethylester-modified pyrimidine nucleoside, and 1 mL of pyridine/dimethylaminopyridine (1:1) is syringed slowly (60 to 90 sec) through a 1 μM column of CPG thymidine (Applied Biosystems, Inc.) that had previously been treated with acid according to standard conditions to afford the free 5'-hydroxyl group. Other nucleoside-bound CPG columns may be employed. The eluent is collected and syringed again through the column. This process is repeated three times. The CPG column is washed slowly with 10 mL of acetonitrile and then attached to an ABI 380B nucleic acid synthesizer. Oligonucleotide synthesis is now initiated. The standard conditions of concentrated ammonium hydroxide deprotection that cleaves the thymidine ester linkage from the CPG support also cleaves the 3',5' ester linkage connecting the pyrimidine modified nucleoside to the thymidine that was initially bound to the CPG nucleoside. In this manner, any 2'-substituted nucleoside or generally any nucleoside with modifications in the heterocycle and/or sugar can be attached at the 3' end of an oligonucleotide.

EXAMPLE 13

Procedure for the conversion of 2'-deoxy-2'-substituted ribonucleoside-5'-DMT-3'-phosphoramidites into oligonucleotides.

The polyribonucleotide solid phase synthesis procedure of Sproat et al. [*Nucleic Acids Research*, 17, 3373 (1989)] is utilized to prepare 2'-modified oligonucleotides.

Oligonucleotides of the sequence CGACTATGCAAG-TAC (SEQ ID NO:21) having 2'-deoxy-2'-fluoro nucleotides were incorporated at various positions within this sequence. In a first oligonucleotide, each of the adenosine nucleotides at positions 3, 6, 10, 11 and 14 (5' to 3' direction) were modified to include a 2'-deoxy-2'-fluoro moiety. In a further oligonucleotide, the adenosine and the thymidine nucleotides at positions 3, 5, 6, 7, 10, 11, 13 and 14 were so modified. In a further oligonucleotide, the adenosine, thymidine and cytidine nucleotides at positions 1, 3, 4, 5, 6, 7, 9, 10, 11, 13 and 14 were so modified, and in even a further oligonucleotide, the nucleotides (adenosine, thymidine, cytidine and guanosine) at every position were so modified. Additionally, an oligonucleotide having the sequence CTCGTACCTTCCGGTCC (SEQ ID NO:22) was prepared having adenosine, thymidine and cytidine nucleotides at positions 1, 2, 3, 5, 6, 7, 8, 9, 10, 11, 12, 15 and 16 also modified to contain 2'-deoxy-2'-fluoro substituents.

Various oligonucleotides were prepared incorporating nucleotides having 2'-deoxy-2'-methylthio substituents. For ascertaining the coupling efficiencies of 2'-deoxy-2'-methylthio bearing nucleotides into oligonucleotides, the trimer TCC and the tetramer TUU U were synthesized. In the trimer, the central cytidine nucleotide (the second nucleotide) included a 2'-deoxy-2'-methylthio substituent. In the tetramer, each of the uridine nucleotides included a 2'-deoxy-2'methylthio substituent. In further oligonucleotides, 2'-deoxy-2'-methylthio substituent bearing nucleotides were incorporated within the oligonucleotide sequence in selected sequence positions. Each of the nucleotides at the remaining sequence positions incorporated a 2'-O-methyl substituent. Thus, all the nucleotides within the oligonucleotide included a substituent group thereon, either a 2'-deoxy-2'-methylthio substituent or a 2'-O-methyl substituent. These oligonucleotides are: GAGCUCCCAGGC (SEQ ID NO:23) having 2'-deoxy-2'-methylthio substituents at positions 4, 5, 6, 7 and 8; CGACUAUGCAAGUAC (SEQ ID NO:24) having 2'-deoxy-2'-methylthio substituents at positions 1, 4, 5, 7, 9 and 13; UCCAGGIJGTJCCGAUC (SEQ ID NO:25) having 2'-deoxy-2'-methylthio substituents at positions 1, 2, 3, 7, 9, 10, 11 and 14; TCCAGGCCGU-UUC (SEQ ID NO:26) having 2'-deoxy-2'-methylthio substituents at positions 10, 11 and 12; and TCCAGGTGTC-CCC (SEQ ID NO:27) having 2'-deoxy-2'-methylthio substituents at positiors 10, 11 and 12.

EXAMPLE 14

Preparation of 2'-Deoxy-2'-fluoro Modified Phosphorothioates Oligonucleotides.

2'-Deoxy-2'-substituted 5'-DMT nucleoside 3'-phosphoramidites prepared as described in Examples 1–7 were inserted into sequence-specific oligonucleotide phosphorothioates as described by Beaucage et al. [*Journal of American Chemical Society*, 112, 1253 (1990)] and Sproat et al. [*Nucleic Acids Research*, 17, 3373 (1989)]. oligonucleoticles of the sequence CGA CTA TGC AAG TAC having phosphorothioate backbone linkages and 2'-deoxy-2'-fluoro substituent bearing nucleotides were incorporated at various positions within this sequence. In a first oligonucleotide, each of the backbone linkages was a phosphorothioate linkage and each of the adenosine, thymidine and cytidine nucleotides at positions 1, 3, 4, 5, 6, 7, 9, 10, 11, 13 and 14 (5' to 3' direction) were modified to include a 2'-deoxy-2'-fluoro moiety. In a further oligonucleotide, each of the backbone linkages was a phosphorothioate linkage and the nucleotides (adenosine, thymidine, cytidine and guanosine) at every position were modified to include a 2'-deoxy-2'-fluoro moiety.

EXAMPLE 15

Preparation of 2'-Deoxy-2'-fluoro Modified Phosphate Methylated Oligonucleotides.

The protection; tosyl chloride mediated methanolysis, and mild deprotection described by Koole et al. [*Journal of Organic Chemistry*, 54, 1657 (1989)] is applied to 2'-substituted oligonucleotides to afford phosphate-methylated 2'-substituted oligonucleotides.

EXAMPLE 16

Hybridization Analysis.

A. Evaluation of the thermodynamics of hybridization of 2'-modified oligonucleotides.

The ability of the 2'-modified oligonucleotides to hybridize to their complementary RNA or DNA sequences was determined by thermal melting analysis. The RNA complement was synthesized from T7 RNA polymerase and a template-promoter of DNA synthesized with an Applied Biosystems, Inc. 380B RNA species was purified by ion exchange using FPLC (LKB Pharmacia, Inc.). Natural antisense oligonucleotides or those containing 2'-modifications at specific locations were added to either the RNA or DNA complement at stoichiometric concentrations and the absorbance (260 nm) hyperchromicity upon duplex to random coil transition was monitored using a Gilford Response II spectrophotometer. These measurements were performed in a buffer of 10 mM Na-phosphate, pH 7.4, 0.1 mM EDTA, and NaCl to yield an ionic strength of 10 either 0.1M or 1.0M. Data was analyzed by a graphic representation of $1/T_m$ vs $\ln[Ct]$, where $[Ct]$ was the total oligonucleotide concentration. From this analysis the thermodynamic parameters were determined. Based upon the information gained concerning the stability of the duplex of heteroduplex formed, the placement of modified pyrimidine into oligonucleotides were assessed for their effects on helix stability. Modifications that drastically alter the stability of the hybrid exhibit reductions in the free energy (delta G) and decisions concerning their usefulness as antisense oligonucleotides were made.

As is shown in the following table (Table 1), the incorporation of 2'-deoxy-2'-fluoro nucleotides into oligonucleotides resulted in significant increases in the duplex stability of the modified oligonucletide strand (the antisense strand) and its complementary RNA strand (the sense strand). In both, phosphodiester backbone and phosphorothioate backbone oligonucleotides, the stability of the duplex increased as the number of 2'-deoxy-2'-fluoro-containing nucleotides in the antisense strand increased. As is evident from Table 1, without exception, the addition of a 2'-deoxy-2'-fluoro bearing nucleotide, irrespective of the individual substituent bearing nucleotide or the position of that nucleotide in the oligonucleotide sequence, resulted in an increase in the duplex stability.

In Table 1, the underlined nucleotides represent nucleotides that include 1 2'-deoxy-2'-fluoro substituent. The oligonucleotides prefaced with the designation "ps" have a phosphorothioate backbone. Unlabeled oligonucleotides have phosphodiester backbones.

was determined by isolation of total cellular RNA by standard techniques and its analysis by agarose electrophoresis, membrane transfer and probing with the labeled 2'-modified oligonucleotides. Stringency was predetermined for the unmodified antisense oligonucleotides and the conditions used such that only the specifically targeted mRNA was capable of forming a heteroduplex with the 2'-modified oligonucleotide.

C. Base-pair specificity of oligonucleotides and RNA

Base-pair specificity of 2'-deoxy-2'-fluoro modified oligonucleotides with the RNA complement (a "Y" strand) was

TABLE 1

EFFECTS OF 2'-DEOXY-2'-FLUORO MODIFICATIONS ON DNA (ANTISENSE) RNA (SENSE) DUPLEX STABILITY

| Antisense Sequence | G°37 (kcal/mol) | G°37 (kcal/mol) | $T_m$ (°C.) | $T_m$ (°C.) | $T_m$ (°C.)/subst. |
|---|---|---|---|---|---|
| CGA CTA TGC AAG TAC (SEQ ID NO: 21) | −10.11 ± 0.04 | | 45.1 | | |
| CGA CTA TGC AAG TAC (SEQ ID NO: 21) | −13.61 ± 0.08 | −3.50 ± 0.09 | 53.0 | +7.9 | +1.6 |
| CGA CUA UGC AAG UAC (SEQ ID NO: 24) | −16.18 ± 0.08 | −6.07 ± 0.09 | 58.9 | +13.8 | +1.7 |
| CGA CUA UGC AAG UAC (SEQ ID NO: 24) | −19.85 ± 0.05 | −9.74 ± 0.06 | 65.2 | +20.1 | +1.8 |
| ps(CGA CTA AAG TAC) (SEQ ID NO: 21) | −7.58 ± 0.06 | | 33.9 | −11.2 | |
| ps(CG A CUA UGC AAG UAC) (SEQ ID NO: 24) | −15.90 ± 0.34 | −8.32 ± 0.34 | 60.9 | +27.0 | +2.5 |
| CTC GTA CCT TCC GGT CC (SEQ ID NO: 22) | −14.57 ± 0.13 | | 61.6 | | |
| CUC GUA CCU UCC GGU CC (SEQ ID NO: 28) | −27.81 ± 0.05 | −13.24 ± 0.14 | 81.6 | +1.4 | |

As is evident from Table 1, the duplexes formed between RNA and oligonucleotides containing 2'-deoxy-2'-fluoro substituted nucleotides exhibited increased binding stability as measured by the hybridization thermodynamic stability. Delta $T_m$s of greater than 20° C. were measured. By modifying the backbone to a phosphorothioate backbone, even greater delta $T_m$s were observed. In this instance, delta $T_m$s greater than 31° C. were measured. These fluoro-substituted oligonucleotides exhibited a consistent and additive increase in the thermodynamic stability of the duplexes formed with RNA. While we do not wish to be bound by theory, it is presently believed that the presence of a 2'-fluoro substituent results in the sugar moiety of the 2'-fluoro-substituted nucleotide assuming substantially a 3'-endo conformation and this results in the oligonucleotide-RNA complex assuming an A-type helical conformation.

B. Fidelity of hybridization of 2'-modified oligonucleotides

The ability of the 2'-modified antisense oligonucleotides to hybridize with absolute specificity to the targeted mRNA was shown by Northern blot analysis of purified target mRNA in the presence of total cellular RNA. Target mRNA was synthesized from a vector containing the cDNA for the target mRNA located downstream from a T7 RNA polymerase promoter. Synthesized mRNA was electrophoresed in an agarose gel and transferred to a suitable support membrane (i.e. nitrocellulose). The support membrane was blocked and probed using $^{32}$P-labeled antisense oligonucleotides. The stringency will be determined by replicate blots and washing in either elevated temperatures or decreased ionic strength of the wash buffer. Autoradiography was performed to assess the presence of heteroduplex formation and the autoradiogram quantitated by laser densitometry (LKB Pharmacia, Inc.). The specificity of hybrid formation determined by effecting single base-pair mismatches and a bulge. The results of these determinations are shown in Table 2. An 18mer "X" strand oligonucleotide containing 14 adenosine, thymidine and cytidine nucleotides having a 2'-deoxy-2'-fluoro substituent was hybridized with the RNA complement "Y" strand in which the 10th position was varied. In Table 2, the underlined nucleotides represent nucleotides that include a 2'-deoxy-2'-fluoro substituent.

As is evident from Table 2, the 2'-deoxy-2'-fluoro modified oligonucleotide formed a duplex with the RNA complement with greater specificity than a like-sequenced unmodified oligonucleotide.

TABLE 2

EFFECTS OF SINGLE BASE MISMATCHES ON 2'-DEOXY-2'-FLUORO MODIFIED DNA-RNA DUPLEX STABILITY

| Y | Base pair type | G°37 (kcal/mol) | G°37 (kcal/mol) | $T_m$ (°C.) | $T_m$ (°C.) |
|---|---|---|---|---|---|
| X strand: deoxy(CTC GTA CCT TTC CGG TCC) (SEQ ID NO: 29) Y strand: ribo($^3$'GAG CAU GGY AAG GCC AGG$^5$') (SEQ ID NO: 30) | | | | | |
| A | Watson-Crick | −14.57 ± 0.13 | | 61.6 | |
| C | T-C mismatch | −12.78 ± 0.11 | 1.79 ± 0.17 | 54.4 | −7.2 |
| G | T-G mismatch | −16.39 ± 0.25 | −1.82 ± 0.28 | 61.7 | 0.1 |
| U | T-U mismatch | −13.48 ± 0.17 | 1.09 ± 0.22 | 55.9 | −5.7 |
| None | Bulged T | −14.86 ± 0.35 | −0.284 ± 0.37 | 59.4 | −2.2 |
| X strand: deoxy(CUC GUA CCU UUC CGG UCC) (SEQ ID NO: 31) Y strand: ribo($^3$'GAG CAU GGY AAG GCC AGG$^5$') (SEQ ID NO: 30) | | | | | |
| A | Watson-Crick | −27.80 ± 0.05 | | 81.6 | |
| C | U-C mismatch | −21.98 ± 0.28 | 5.82 ± 0.28 | 73.8 | −7.8 |
| G | U-G mismatch | −21.69 ± 0.16 | 6.12 ± 0.17 | 77.8 | −3.8 |

TABLE 2-continued

EFFECTS OF SINGLE BASE MISMATCHES ON
2'-DEOXY-2'-FLUORO MODIFIED DNA-RNA DUPLEX STABILITY

| Y | Base pair type | G°37 (kcal/mol) | G°37 (kcal/mol) | $T_m$ (°C.) | $T_m$ (°C.) |
|---|---|---|---|---|---|
| U | U-U mismatch | −18.68 ± 0.15 | 9.13 ± 0.16 | 73.6 | −8.0 |
| None | Bulged U | −22.87 ± 0.27 | 4.94 ± 0.27 | 75.5 | −6.2 |

EXAMPLE 17

Nuclease Resistance

A. Evaluation of the resistance of 2'-modified oligonucleotides to serum and cytoplasmic nucleases.

Natural phosphorothioate, and 2-modified oligonucleotides were assessed for their resistance to serum nucleases by incubation of the oligonucleotides in media containing various concentrations of fetal calf serum or adult human serum. Labeled oligonucleotides were incubated for various times, treated with protease K and then analyzed by gel electrophoresis on 20% polyacrylamide-urea denaturing gels and subsequent autoradiography. Autoradiograms were quantitated by laser densitometry. Based upon the location of the modifications and the known length of the oligonucleotide it was possible to determine the effect on nuclease degradation by the particular 2'-modification. For the cytoplasmic nucleases, a HL60 cell line was used. A post-mitochondrial supernatant was prepared by differential centrifugation and the labeled oligonucleotides were incubated in this supernatant for various times. Following the incubation, oligonucleotides were assessed for degradation as outlined above for serum nucleolytic degradation. Autoradiography results were quantitated for comparison of the unmodified, the phosphorothioates, and the 2'-modified oligonucleotides.

Utilizing these test systems, the stability of a 15mer oligonucleotide having 2'-deoxy-2'-fluoro-substituted nucleotides at positions 12 and 14 and a phosphorothioate backbone were investigated. As a control, an unsubstituted phosphodiester oligonucleotide was 50% degraded within 1 hour, and 100% degraded within 20 hours. In comparison, for the 2'-deoxy-2'-fluoro-substituted oligonucleotide having a phosphorothioate backbone, degradation was limited to less that 10% after 20 hours.

B. Evaluation of the resistance of 2'-modified oligonucleotides to specific endo- and exonucleases.

Evaluation of the resistance of natural and 2'-modified oligonucleotides to specific nucleases (i.e., endonucleases, 3',5'-exo-, and 5',3'-exonucleases) was done to determine the exact effect of the modifications on degradation. Modified oligonucleotides were incubated in defined reaction buffers specific for various selected nucleases. Following treatment of the products with protease K, urea was added and analysis on 20% poly-acrylamide gels containing urea was done. Gel products were visualized by staining using StainsAll (Sigma Chemical Co.). Laser densitometry was used to quantitate the extend of degradation. The effects of the 2'-modifications were determined for specific nucleases and compared with the results obtained from the serum and cytoplasmic systems.

EXAMPLE 18

Oligonucleotide Synthesis

Unsubstituted and substituted oligonucleotides were synthesized on an automated DNA synthesizer (Applied Biosystems model 380B) using standard phosphoramidite chemistry with oxidation by iodine. For phosphorothioate oligonucleotides, the standard oxidation bottle was replaced by 0.2M solution of 3H-1,2-benzodithiole-3-one-1,1-dioxide in acetonitrile for the step wise thiation of the phosphite linkages. The thiation wait step was increased to 68 sec and was followed by the capping step. After cleavage from the CPG column and deblocking in concentrated ammonium hydroxide at 55° C. (18 hours), the oligonucleotides were purified by precipitating twice with 2.5 volumes of ethanol from a 0.5M NaCl solution. Analytical gel electrophoresis was accomplished in 20% acrylamide, 8M urea, 454 mM Tris-borate buffer, pH=7.0. Oligonucleotides and phosphorothioates were judged, based on polyacrylamide gel electrophoresis, to be greater than 80% full-length material.

EXAMPLE 19

Oligonucleotide Having 2'-Substituted Oligonucleotides Regions Flanking Central 2'-Deoxy Phosphorothioate Oligonucleotide Region A 15mer RNA target of the sequence 5'GCGTTTTTTTTTTGCG 3' (SEQ ID NO:32) was prepared in the normal manner on the DNA sequencer using RNA protocols. A series of complementary phosphorothioate oligonucleotides having 2'-O-substituted nucleotides in regions that flank a 2'-deoxy region were prepared utilizing 2'-O-substituted nucleotide precursors prepared as per known literature preparations, i.e. 2'-O-methyl, or as per the procedure of International Publication Number WO 92/03568, published Mar. 5, 1992. The 2'-O-substituted nucleotides were added as their 5'-O-dimethoxytrityl-3'-phosphoramidites in the normal manner on the DNA synthesizer. The complementary oligonucleotides have the sequence of 5' CGCAAAAAAAAAAAAACGC 3' (SEQ ID NO:33). The 2'-O-substituent was located in CGC and CG regions of these oligonucleotides. The following 2'-O-substituents were used: 2'-fluoro; 2'-O-methyl; 2'-O-propyl; 2'-O-allyl; 2'-O-aminopropoxy; 2'-O-(methoxyethoxyethyl), 2'-O-imidazolebutoxy and 2-O-imidazolepropoxy.

EXAMPLE 20

Ras-Luciferase Reporter Gene Assembly

The ras-luciferase reporter genes described in this study were assembled using PCR technology. Oligonucleotide primers were synthesized for use as primers for PCR cloning of the 5'-regions of exon 1 of both the mutant (codon 12) and non-mutant (wild-type) human H-ras genes. H-ras gene templates were purchased from the American Type Culture Collection (ATCC numbers 41000 and 41001) in Bethesda, Md. The oligonucleotide PCR primers 5'-ACA-TTA-TGC-TAG-CTT-TTT-GAG-TAA-ACT-TGT-GGG-GCA-GGA-GAC-CCT-GT-3' (sense) (SEQ ID NO:34), and 5'-GAG-ATC-TGA-AGC-TTC-TGG-ATG-GTC-AGC-GC-3' (antisense) (SEQ ID NO:35), were used in standard PCR reactions using mutant and non-mutant H-ras genes as templates. These primers are expected to produce a DNA product of 145 base pairs corresponding to sequences −53 to +65 (relative to the translational initiation site) of normal and mutant H-ras, flanked by NheI and HindIII restriction endonuclease sites. The PCR product was gel purified, precipitated, washed and resuspended in water using standard procedures.

PCR primers for the cloning of the *P. pyralis* (firefly) luciferase gene were designed such that the PCR product would code for the full-length luciferase protein with the exception of the amino-terminal methionine residue, which would be replaced with two amino acids, an amino-terminal lysine residue followed by a leucine residue. The oligonucleotide PCR primers used for the cloning of the luciferase gene were 5'-GAG-ATC-TGA-AGC-TTG-AAG-ACG-CCA-AAA-ACA-TAA-AG-3' (sense) (SEQ ID NO:36), and 5'-ACG-CAT-CTG-GCG-CGC-CGA-TAC-CGT-CGA-CCT-CGA-3' (antisense) (SEQ ID NO:37), were used in standard PCR reactions using a commercially available plasmid (pT3/T7-Luc) (Clontech), containing the luciferase reporter gene, as a template. These primers were expected to yield a product of approximately 1.9 kb corresponding to the luciferase gene, flanked by HindIII and BssHII restriction endonuclease sites. This fragment was gel purified, precipitated, washed and resuspended in water using standard procedures.

To complete the assembly of the ras-luciferase fusion reporter gene, the ras and luciferase PCR products were digested with the appropriate restriction endonucleases and cloned by three-part ligation into an expression vector containing the steroid-inducible mouse mammary tumor virus promotor MMTV using the restriction endonucleases NheI, HindIII and BssHII. The resulting clone results in the insertion of H-ras 5' sequences (−53 to +65) fused in frame with the firefly luciferase gene. The resulting expression vector encodes a ras-luciferase fusion product which is expressed under control of the steroid-inducible MMTV promoter.

EXAMPLE 21

Transfection of Cells with Plasmid DNA

Transfections were performed as described by Greenberg in *Current Protocols in Molecular Biology*, Ausubel et al., Eds., John Wiley and Sons, New York, with the following modifications: HeLa cells were plated on 60 mm dishes at $5 \times 10^5$ cells/dish. A total of 10 µg of DNA was added to each dish, of which 9 µg was ras-luciferase reporter plasmid and 1 µg was a vector expressing the rat glucocorticoid receptor under control of the constitutive Rous sarcoma virus (RSV) promoter. Calcium phosphate-DNA coprecipitates were removed after 16–20 hours by washing with Tris-buffered saline [50Mm Tris-Cl (pH 7.5), 150 mM NaCl] containing 3 mM EGTA. Fresh medium supplemented with 10% fetal bovine serum was then added to the cells. At this time, cells were pretreated with antisense oligonucleotides prior to activation of reporter gene expression by dexamethasone.

EXAMPLE 22

Oligonucleotide Treatment of Cells

Immediately following plasmid transfection, cells were thrice washed with OptiMEM (GIBCO), and prewarmed to 37° C. 2 ml of OptiMEM containing 10 µg/ml N-[1-(2,3-diolethyloxy)propyl]-N,N,N,-trimethylammonium chloride (DOTMA) (Bethesda Research Labs, Gaithersburg, Md.) was added to each dish and oligonucleotides were added directly and incubated for 4 hours at 37° C. OptiMEM was then removed and replaced with the appropriate cell growth medium containing oligonucleotide. At this time, reporter gene expression was activated by treatment of cells with dexamethasone to a final concentration of 0.2 µM. Cells were harvested 12–16 hours following steroid treatment.

EXAMPLE 23

Luciferase Assays

Luciferase was extracted from cells by lysis with the detergent Triton X-100, as described by Greenberg in *Current Protocols in Molecular Biology*, Ausubel et al., Eds., John Wiley and Sons, New York. A Dynatech ML1000 luminometer was used to measure peak luminescence upon addition of luciferin (Sigma) to 625 µM. For each extract, luciferase assays were performed multiple times, using differing amounts of extract to ensure that the data were gathered in the linear range of the assay.

EXAMPLE 24

Antisense Oligonucleotide Inhibition of ras-Luciferase Gene Expression

A series of antisense phosphorothioate oligonucleotide analogs targeted to the codon-12 point mutation of activated H-ras were tested using the ras-luciferase reporter gene system described in the foregoing examples. This series comprised a basic sequence and analogs of that basic sequence. The basic sequence was of known activity as reported in International Publication Number WO 92/22651 identified above. In both the basic sequence and its analogs, each of the nucleotide subunits incorporated phosphorothioate linkages to provide nuclease resistance. Each of the analogs incorporated nucleotide subunits that contained 2'-O-methyl substitutions and 2'-deoxy-erythro-pentofuranosyl sugars. In the analogs, a subsequence of the 2'-deoxy-erythro-pentofuranosyl sugar-containing subunits was flanked on both ends by subsequences of 2'-O-methyl substituted subunits. The analogs differed from one another with respect to the length of the subsequence of the 2'-deoxy-erythro-pentofuranosyl sugar containing nucleotides. The length of these subsequences varied by 2 nucleotides between 1 and 9 total nucleotides. The 2'-deoxy-erythro-pentofuranosyl nucleotide sub-sequences were centered at the point mutation of the codon-12 point mutation of the activated ras.

The base sequences, sequence reference numbers and sequence ID numbers of these oligonucleotides (all are phosphorothioate analogs) are shown in Table 3. In this table those nucleotides identified with a "$^M$" contain a 2'-O-methyl substituent group and the remainder of the nucleotides identified with a "$_d$" are 2'-deoxy-erythro-pentofuranosyl nucleotides.

TABLE 3

Chimeric 2'-O-methyl P=S oligonucleotides

| OLIGO | SEQUENCE | | | | | | SEQ ID NO: |
|---|---|---|---|---|---|---|---|
| 2570 | $C_dC_dA_d$ | $C_dA_dC_d$ | $C_dG_dA_d$ | $C_dG_dG_d$ | $C_dG_dC_d$ | $C_dC_d$ | 1 |
| 3975 | $C^MC^MA^M$ | $C^MA^MC^M$ | $C^MG^MA_d$ | $C^MG^MG^M$ | $C^MG^MC^M$ | $C^MC^M$ | 1 |
| 3979 | $C^MC^MA^M$ | $C^MA^MC^M$ | $C^MG_dA_d$ | $C_dG^MG^M$ | $C^MG^MC^M$ | $C^MC^M$ | 1 |
| 3980 | $C^MC^MA^M$ | $C^MA^MC^M$ | $C_dG_dA_d$ | $C_dG_dG^M$ | $C^MG^MC^M$ | $C^MC^M$ | 1 |

TABLE 3-continued

Chimeric 2'-O-methyl P=S oligonucleotides

| OLIGO | SEQUENCE | | | | | SEQ ID NO: |
|-------|----------|---|---|---|---|------------|
| 3985  | $C^M C^M A^M$ | $C^M A^M C_d$ | $C_d G_d A_d$ | $C_d G_d G_d$ | $C^M G^M C^M$ $C^M C^M$ | 1 |
| 3984  | $C^M C^M A^M$ | $C^M A_d C_d$ | $C_d G_d A_d$ | $C_d G_d G_d$ | $C_d G^M C^M$ $C^M C^M$ | 1 |

FIG. 1 shows dose-response data in which cells were treated with the phosphorothioate oligonucleotides of Table 3. Oligonucleotide 2570 is targeted to the codon-12 point mutation of mutant (activated) H-ras RNA. The other nucleotides have 2'-O-methyl substituents groups thereon to increase binding affinity with sections of various lengths of interspaced 2'-deoxy-erythro-pentofuranosyl nucleotides. The control oligonucleotide is a random phosphorothioate oligonucleotide analog, 20 bases long. Results are expressed as percentage of luciferase activity in transfected cells not treated with oligonucleotide. As the figure shows, treatment of cells with increasing concentrations of oligonucleotide 2570 resulted in a dose-dependent inhibition of ras-luciferase activity in cells expressing the mutant form of ras-luciferase. Oligonucleotide 2570 displays an approximate threefold selectivity toward the mutant form of ras-luciferase as compared to the normal form. As is further seen in FIG. 1, each of the oligonucleotides 3980, 3985 and 3984 exhibited greater inhibition of ras-luciferase activity than did oligonucleotide 2570. The greatest inhibition was displayed by oligonucleotide 3985 that has a subsequence of 2'-deoxy-erythro-pentofuranosyl nucleotides seven nucleotides long. Oligonucleotide 3980, having a five nucleotide long 2'-deoxy-erythro-pentofuranosyl nucleotide subsequence exhibited the next greatest inhibition followed by oligonucleotide 3984 that has a nine nucleotide 2'-deoxy-erythro-pentofuranosyl nucleotide subsequence.

Figure 2:
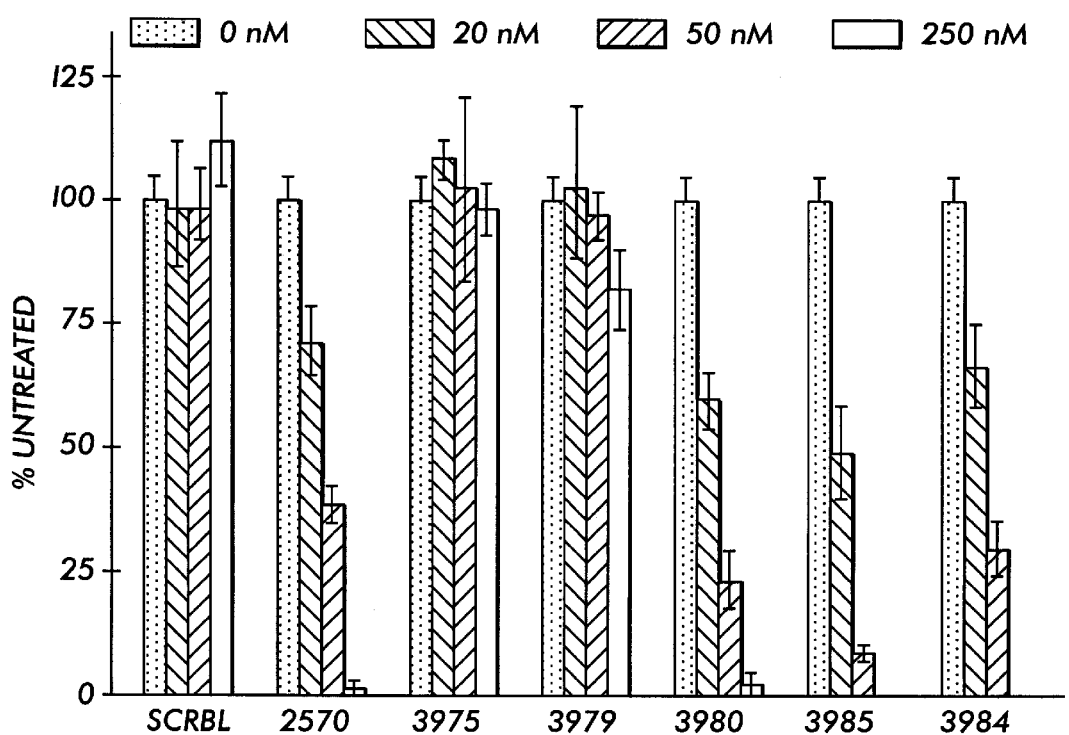
FIG. 2 is a bar chart showing dose response activity of oligonucleotides of the invention and reference compounds.

FIG. 2 shows the results similar to FIG. 1 except it is in bar graph form. Further seen on FIG. 2 is the activity of oligonucleotide 3975 and oligonucleotide 3979. These oligonucleotides have subsequences of 2'-deoxy-erythro-pentofuranosyl nucleotides one and three nucleotides long, respectively. As is evident from FIG. 2, neither of the oligonucleotides having either the one or the three 2'-deoxy-erythro-pentofuranosyl nucleotide subsequences showed significant activity. There was measurable activity for the three nucleotide subsequence oligonucleotide 3979 at the highest concentration dose.

The increases in activity of oligonucleotides 3980, 3985 and 3984 compared to oligonucleotide 2570 is attributed to the increase in binding affinity imparted to these compounds by the 2'-O-methyl substituent groups located on the compounds and by the RNase H activation imparted to these compounds by incorporation of a subsequence of 2'-deoxy-erythro-pentofuranosyl nucleotides within the main sequence of nucleotides. In contrast to the active compounds of the invention, it is interesting to note that sequences identical to those of the active oligonucleotides 2570, 3980, 3985 and 3984 but having phosphodiester linkages in stead of the phosphorothioate linkages of the active oligonucleotides of the invention showed no activity. This is attributed to these phosphodiester compounds being substrates for nucleases that degrade such phosphodiester compounds thus preventing them potentially activating RNase H.

Other sugar modifications: The effects of other 2' sugar modifications besides 2'-O-methyl on antisense activity in chimeric oligonucleotides have been examined. These modifications are listed in Table 4, along with the $T_m$ values obtained when 17mer oligonucleotides having 2'-modified nucleotides flanking a 7-base deoxy gap were hybridized with a 25mer oligoribonucleotide complement as described in Example 25. A relationship was observed for these oligonucleotides between alkyl length at the 2' position and $T_m$. As alkyl length increased, $T_m$ decreased. The 2'-fluoro chimeric oligonucleotide displayed the highest $T_m$ of the series.

TABLE 4

Correlation of $T_m$ with Antisense Activity
2'-modified 17-mer with 7-deoxy gap
CCACACCGACGGCGCCC (SEQ ID NO: 1)

| 2' MODIFICATION | $T_m$ (°C.) | $ID_{50}$ (nM) |
|-----------------|-------------|----------------|
| Deoxy    | 64.2 | 150 |
| O-Pentyl | 68.5 | 150 |
| O-Propyl | 70.4 | 70  |
| O-Methyl | 74.7 | 20  |
| Fluoro   | 76.9 | 10  |

These 2' modified oligonucleotides were tested for antisense activity against H-ras using the transactivation reporter gene assay described in Example 26. All of these 2' modified chimeric compounds inhibited ras expression, with the 2'-fluoro 7-deoxy-gap compound being the most active. A 2'-fluoro chimeric oligonucleotide with a centered 5-deoxy gap was also active.

Chimeric phosphorothioate oligonucleotides having SEQ ID NO:1 having 2'-O-propyl regions surrounding a 5-base or 7-base deoxy gap were compared to 2'-O-methyl chimeric oligonucleotides. ras expression in T24 cells was inhibited by both 2'-O-methyl and 2'-O-propyl chimeric oligonucleotides with a 7-deoxy gap and a uniform phosphorothioate backbone. When the deoxy gap was decreased to five nucleotides, only the 2'-O-methyl oligonucleotide inhibited ras expression.

Antisense oligonucleotide inhibition of H-ras gene expression in cancer cells: Two phosphorothioate oligonucleotides (2502, 2503) complementary to the ras AUG region were tested as described in Example 27, along with chimeric oligonucleotides (4998, 5122) having the same sequence and 7-base deoxy gaps flanked by 2'-O-methyl regions. These chimeric oligonucleotides are shown in Table 5.

TABLE 5

Chimeric phosphorothioate oligonucleotides having
2'-O-methyl ends (bold) and central deoxy gap (AUG target)

| OLIGO | # DEOXY | SEQUENCE | SEQ ID NO: |
|-------|---------|----------|------------|
| 2502 | 20 | CTTATATTCCGTCATCGCTC | 2 |
| 4998 | 7  | CTTATATTCCGTCATCGCTC | 2 |

TABLE 5-continued

Chimeric phosphorothioate oligonucleotides having
2'-O-methyl ends (bold) and central deoxy gap (AUG target)

| OLIGO | # DEOXY | SEQUENCE | SEQ ID NO: |
|---|---|---|---|
| 2503 | 20 | TCCGTCATCGCTCCTCAGGG | 3 |
| 5122 | 7 | TCCGTCATCGCTCCTCAGGG | 3 |

Compound 2503 inhibited ras expression in T24 cells by 71%, and the chimeric compound (4998) inhibited ras mRNA even further (84% inhibition). Compound 2502, also complementary to the AUG region, decreased ras RNA levels by 26% and the chimeric version of this oligonucleotide (5122) demonstrated 15% inhibition. Also included in this assay were two oligonucleotides targeted to the mutant codon 12. Compound 2570 (SEQ ID NO:1) decreased ras RNA by 82% and the 2'-O-methyl chimeric version of this oligonucleotide with a seven-deoxy gap (3985) decreased ras RNA by 95%.

Oligonucleotides 2570 and 2503 were also tested to determine their effects on ras expression in HeLa cells, which have a wild-type (i.e., not activated) H-ras codon-12. While both of these oligonucleotides inhibited ras expression in T24 cells (having activated codon-12), only the oligonucleotide (2503) specifically hybridizable with the ras AUG inhibited ras expression in HeLa cells. oligonucleotide 2570 (SEQ ID NO:1), specifically hybridizable with the activated codon-12, did not inhibit ras expression in HeLa cells, because these cells lack the activated codon-12 target.

Oligonucleotide 2570, a 17mer phosphorothioate oligonucleotide complementary to the codon-12 region of activated H-ras, was tested for inhibition of ras expression (as described in Example 25) in T24 cells along with chimeric phosphorothioate 2'-O-methyl oligonucleotides 3980, 3985 and 3984, which have the same sequence as 2570 and have deoxy gaps of 5, 7 and 9 bases, respectively (shown in Table 3). The fully 2'-deoxy oligonucleotide 2570 and the three chimeric oligonucleotides decreased ras mRNA levels in T24 cells. Compounds 3985 (7-deoxy gap) and 3984 (9-deoxy gap) decreased ras mRNA by 81%; compound 3980 (5-deoxy gap) decreased ras mRNA by 61%. Chimeric oligonucleotides having this sequence, but having 2'-fluoro-modified nucleotides flanking a 5-deoxy (4689) or 7-deoxy (4690) gap, inhibited ras mRNA expression in T24 cells, with the 7-deoxy gap being preferred (82% inhibition, vs 63% inhibition for the 2'-fluoro chimera with a 5-deoxy gap).

Antisense oligonucleotide inhibition of proliferation of cancer cells: Three 17mer oligonucleotides having the same sequence (SEQ ID NO:1), complementary to the codon 12 region of activated ras, were tested for effects on T24 cancer cell proliferation as described in Example 28. 3985 is a full phosphorothioate oligonucleotide having a 7-deoxy gap flanked by 2'-O-methyl nucleotides, and 4690 is a full phosphorothioate oligonucleotide having a 7-deoxy gap flanked by 2'-F nucleotides ($C^FC^FA^F$ $C^FA^FC_d$ $C_dG_dA_d$ $C_dG_dG_d$ $C^FG^FC^F$ $C^FC^F$, SEQ ID NO:1, nucleotides identified with an "$^F$" contain a 2'-O-fluoro substituent group and the remainder of the nucleotides identified with a "$_d$" are 2'-deoxy-erythro-pentofuranosyl nucleotides). Effects of these oligonucleotides on cancer cell proliferation correlated well with their effects on ras mRNA expression shown by Northern blot analysis: oligonucleotide 2570 inhibited cell proliferation by 61%, the 2'-O-methyl chimeric oligonucleotide 3985 inhibited cell proliferation by 82%, and the 2'-fluoro chimeric analog inhibited cell proliferation by 93%.

In dose-response studies of these oligonucleotides on cell proliferation, the inhibition was shown to be dose-dependent in the 25 nM-100 nM range. $IC_{50}$ values of 44 nM, 61 nM and 98 nM could be assigned to oligonucleotides 4690, 3985 and 2570, respectively. The random oligonucleotide control had no effect at the doses tested.

The effect of ISIS 2570 on cell proliferation was cell type-specific. The inhibition of T24 cell proliferation by this oligonucleotide was four times as severe as the inhibition of HeLa cells by the same oligonucleotide (100 nM oligonucleotide concentration). ISIS 2570 is targeted to the activated (mutant) ras codon-12, which is present in T24 but lacking in HeLa cells, which have the wild-type codon-12.

Chimeric backbone-modified oligonucleotides: Oligonucleotides discussed in previous examples have had uniform phosphorothioate backbones. The 2'modified chimeric oligonucleotides discussed above are not active in uniform phosphodiester backbones. A chimeric oligonucleotide was synthesized (ISIS 4226) having 2'-O-methyl regions flanking a 5-nucleotide deoxy gap, with the gap region having a P=S backbone and the flanking regions having a P=O backbone. Another chimeric oligonucleotide (ISIS 4223) having a P=O backbone in the gap and P=S in flanking regions was also made. These oligonucleotides are shown in Table 6.

Additional oligonucleotides were synthesized, completely 2'deoxy and having phosphorothioate backbones containing either a single phosphodiester (ISIS 4248), two phosphodiesters (ISIS 4546), three phosphodiesters (ISIS 4551), four phosphodiesters (ISIS 4593), five phosphodiesters (ISIS 4606) or ten phosphodiester linkages (ISIS-4241) in the center of the molecule. These oligonucleotides are also shown in Table 6.

TABLE 6

Chimeric backbone (P=S/P=O) oligonucleotides
having 2'-O-methyl wings (bold) and central deoxy gap
(backbone linkages indicated by s (P=S) or o (P=O))

| OLIGO | # P=S | SEQUENCE | SEQ ID NO: |
|---|---|---|---|
| 2570 | 16 | CsCsAsCsAsCsCsGsAsCsGsGsCsGsCsC | 1 |
| 4226 | 5 | CoCoAoCoAoCsCsGsAsCsGoGoCoGoCoC | 1 |
| 4233 | 11 | CsCsAsCsAsCoCoGsAoCoGsGsCsGsCsC | 1 |
| 4248 | 15 | CsCsAsCsAsCsCsGsAoCsGsGsCsGsCsC | 1 |
| 4546 | 14 | CsCsAsCsAsCsCsGoAoCsGsGsCsGsCsC | 1 |
| 4551 | 13 | CsCsAsCsAsCsCsGoAoCoGsGsCsGsCsC | 1 |
| 4593 | 12 | CsCsAsCsAsCsCoGoAoCoGsGsCsGsCsC | 1 |
| 4606 | 11 | CsCsAsCsAsCsCoGoAoCoGoGsCsGsCsC | 1 |
| 4241 | 6 | CsCsAsCoAoCoCoGoAoCoGoGoCoGsCsC | 1 |

Oligonucleotides were incubated in crude HeLa cellular extracts at 37° C. to determine their sensitivity to nuclease degradation as described in Dignam et al. [*Nucleic Acids Res.*, 11, 1475 (1983)]. The oligonucleotide (4233) with a 5-diester gap between phosphorothioate/2'-O-methyl wings had a $T_{1/2}$ of 7 hr. The oligonucleotide with a five-phosphorothioate gap in a phosphorothioate/2'-O-methyl molecule had a $T_{1/2}$ of 30 hours. In the set of oligonucleotides having one to ten diester linkages, the oligonucleotide (4248) with a single phosphodiester linkage was as stable to nucleases as was the full-phosphorothioate molecule, ISIS 2570, showing no degradation after 5 hours in HeLa cell extract. Oligonucleotides with two-, three and four-diester gaps had $T_{1/2}$ of approximately 5.5 hours, 3.75 hours, and 3.2 hours, and oligonucleotides with five or ten deoxy linkages had $T_{1/2}$ of 1.75 hours and 0.9 hours, respectively.

Antisense activity of chimeric backbone-modified oligonucleotides: A uniform phosphorothioate backbone is not required for antisense activity. ISIS 4226 and ISIS 4233 were tested in the ras-luciferase reporter system for effect on ras expression along with ISIS 2570 (fully phosphorothioate/all deoxy), ISIS 3980 (fully phosphorothioate, 2'-O-methyl wings with deoxy gap) and ISIS 3961 (fully phosphodiester, 2'-O-methyl wings with deoxy gap). All of the oligonucleotides having a P=S (i.e., nuclease-resistant) gap region inhibited ras expression. The two completely 2'deoxy oligonucleotides having phosphorothioate backbones containing either a single phosphodiester (ISIS 4248) or ten phosphodiester linkages (ISIS 4241) in the center of the molecule were also assayed for activity. The compound containing a single P=O was just as active as a full P=S molecule, while the same compound containing ten P=O was completely inactive.

Chimeric phosphorothioate oligonucleotides of SEQ ID NO:1 were made, having a phosphorothioate backbone in the 7-base deoxy gap region only, and phosphodiester in the flanking regions, which were either 2'-O-methyl or 2'-O-propyl. The oligonucleotide with the 2'-O-propyl diester flanking regions was able to inhibit ras expression.

EXAMPLE 25

Melting Curves

Absorbance vs. temperature curves were measured at 260 nm using a Gilford 260 spectrophotometer interfaced to an IBM PC computer and a Gilford Response II spectrophotometer. The buffer contained 100 mM Na$^+$, 10 mM phosphate and 0.1 mM EDTA, pH 7. Oligonucleotide concentration was 4 μM each strand determined from the absorbance at 85° C. and extinction coefficients calculated according to Puglisi and Tinoco [*Methods in Enzymol.*, 180, 304 (1989). $T_m$ values, free energies of duplex formation and association constants were obtained from fits of data to a two state model with linear sloping baselines. [Petersheim and Turner, *Biochemistry*, 22, 256 (1983). Reported parameters are averages of at least three experiments. For some oligonucleotides, free energies of duplex formation were also obtained from plots of $T_m^{-1}$ vs $\log_{10}$ (concentration). Borer et al., *J. Mol. Biol.*, 86, 843 (1974).

EXAMPLE 26 ras Transactivation Reporter Gene System

The expression plasmid pSV2-oli, containing an activated (codon 12, GGC→GTC) H-ras cDNA insert under control of the constitutive SV40 promoter, was a gift from Dr. Bruno Tocque (Rhone-Poulenc Sante, Vitry, France). This plasmid was used as a template to construct, by PCR, a H-ras expression plasmid under regulation of the steroid-inducible mouse mammary tumor virus (MMTV) promoter. To obtain H-ras coding sequences, the 570 bp coding region of the H-ras gene was amplified by PCR. The PCR primers were designed with unique restriction endonuclease sites in their 5'-regions to facilitate cloning. The PCR product containing the coding region of the H-ras codon 12 mutant oncogene was gel purified, digested, and gel purified once again prior to cloning. This construction was completed by cloning the insert into the expression plasmid pMAMneo (Clontech Laboratories, CA).

The ras-responsive reporter gene pRDO53 was used to detect ras expression. [Owen et al., *Proc. Natl. Acad. Sci. U.S.A.*, 87, 3866 (1990).

EXAMPLE 27

Northern Blot Analysis of ras Expression in vivo

The human urinary bladder cancer cell line T24 was obtained from the American Type Culture Collection (Rockville Md.). Cells were grown in McCoy's 5A medium with L-glutamine (GIBCO-BRL, Gaithersburg, Md.), supplemented with 10% heat-inactivated fetal calf serum and 50 U/ml each of penicillin and streptomycin. Cells were seeded on 100 mm plates. When they reached 70% confluency, they were treated with oligonucleotide. Plates were washed with 10 ml prewarmed PBS and 5 ml of OptiMEM (GIBCO) reduced-serum medium containing 2.5 μl DOTMA. Oligonucleotide was then added to the desired concentration. After 4 hours of treatment, the medium was replaced with McCoy's medium. Cells were harvested 48 hours after oligonucleotide treatment and RNA was isolated using a standard CsCl purification method. [Kingston in *Current Protocols in Molecular Biology*, F. M. Ausubel, R. Brent, R. E. Kingston, D. D. Moore, J. A. Smith, J. G. Seidman and K. Strahl, Eds., John Wiley and Sons, New York.] The human epithelioid carcinoma cell line HeLa 229 was obtained from the American Type Culture Collection (Bethesda, Md.). HeLa cells were maintained as monolayers on 6-well plates in Dulbecco's Modified Eagle's medium (DMEM) supplemented with 10% fetal bovine serum and 100 U/ml penicillin. Treatment with oligonucleotide and isolation of RNA were essentially as described above for T24 cells.

Northern hybridization: 10 μg of each RNA was electrophoresed on a 1.2% agarose/formaldehyde gel and transferred overnight to GeneBind 45 nylon membrane (Pharmacia LKB, Piscataway, N.J.) using standard methods. [Kingston in *Current Protocols in Molecular Biology*, F. M. Ausubel, R. Brent, R. E. Kingston, D. D. Moore, J. A. Smith, J. G. Seidman and K. Strahl, Eds., John Wiley and Sons, New York.] RNA was UV-crosslinked to the membrane. Double-stranded $^{32}$P-labeled probes were synthesized using the Prime a Gene labeling kit (Promega, Madison Wis.). The ras probe was a SalI-NheI fragment of a cDNA clone of the activated (mutant) H-ras mRNA having a GGC-to-GTC mutation at codon-12. The control probe was G3PDH. Blots were prehybridized for 15 minutes at 68° C. with the QuickHyb hybridization solution (Stratagene, La Jolla, Calif.). The heat-denatured radioactive probe (2.5×10$^6$ counts/2 ml hybridization solution) mixed with 100 μl of 10 mg/ml salmon sperm DNA was added and the membrane was hybridized for 1 hour at 68° C. The blots were washed twice for 15 minutes at room temperature in 2× SSC/0.1% SDS and once for 30 minutes at 60° C. with 0.1× SSC/0.1%SDS. Blots were autoradiographed and the intensity of signal was quantitated using an ImageQuant PhosphorImager (Molecular Dynamics, Sunnyvale, Calif.). Northern blots were first hybridized with the ras probe, then stripped by boiling for 15 minutes in 0.1× SSC/0.1%SDS and rehybridized with the control G3PDH probe to check for correct sample loading.

EXAMPLE 28

Antisense Oligonucleotide Inhibition of Proliferation of Cancer Cells

Cells were cultured and treated with oligonucleotide essentially as described in Example 27. Cells were seeded on 60 mm plates and were treated with oligonucleotide in the presence of DOTMA when they reached 70% confluency.

Time course experiment: On day 1, cells were treated with a single dose of oligonucleotide at a final concentration of 100 nM. The growth medium was changed once on day 3 and cells were counted every day for 5 days, using a counting chamber. Dose-response experiment: Various concentrations of oligonucleotide (10, 25, 50, 100 or 250 nM) were added to the cells and cells were harvested and counted 3 days later. Oligonucleotides 2570, 3985 and 4690 were tested for effects on T24 cancer cell proliferation.

EXAMPLE 29

Inhibition of PKC-α mRNA Expression by Chimeric (deoxy gapped) 2'-O-methyl Oligonucleotides Oligonucleotides having SEQ ID NO:4 were synthesized as uniformly phosphorothioate chimeric oligonucleotides having a centered deoxy gap of varying lengths flanked by 2'-O-methylated regions. These oligonucleotides (500 nM concentration) were tested for effects on PKC-α mRNA levels by Northern blot analysis. Deoxy gaps of eight nucleotides or more gave maximal reduction of PKC-α mRNA levels (both transcripts) in all cases. These oligonucleotides reduced PKC-α mRNA by approximately 83% with a deoxy gap length of four nucleotides, and gave nearly complete reduction of PKC-α mRNA with a deoxy gap length of six or more.

The 2'-O-methyl chimeric oligonucleotides with four-or six-nucleotide deoxy gaps have an $IC_{50}$ for PKC-α mRNA reduction (concentration of oligonucleotide needed to give a 50% reduction in PKC-α mRNA levels) of 200–250 nM, as did the full-deoxy oligonuclectide (all are phosphorothioates throughout). The 2'-O-methyl chimeric oligonucleotide with an 8-nucleotide deoxy gap had an $IC_{50}$ of approximately 85 nM.

Several variations of this chimeric oligonucleotide (SEQ ID NO:4) were compared for ability to lower PKC-α mRNA levels. These oligonucleotides are shown in Table 7.

TABLE 7

Chimeric 2'-O-methyl/deoxy P=S oligonucleotides
bold = 2'-O-methyl; s = P=S linkage, o = P=O linkage

| OLIGO | SEQUENCE | SEQ ID NO: |
|---|---|---|
| 3522 | AsAsAsAsCsGsTsCsAsGsCsCsAsTsGsGsTsCsCsC | 4 |
| 5352 | AsAsAsAsCsGsTsCsAsGsCsCsAsTsGsGsTsCsCsC | 4 |
| 6996 | AoAoAoAoCoGsTsCsAsGsCsCsAsTsGoGoToCoCoC | 4 |
| 7008 | AsAoAoAoCoGsTsCsAsGsCsCsAsTsGoGoToCoCsC | 4 |
| 7024 | AsAoAoAoCoGsToCsAoGsCoCsAsTsGoGoToCoCsC | 4 |

Figure 3:
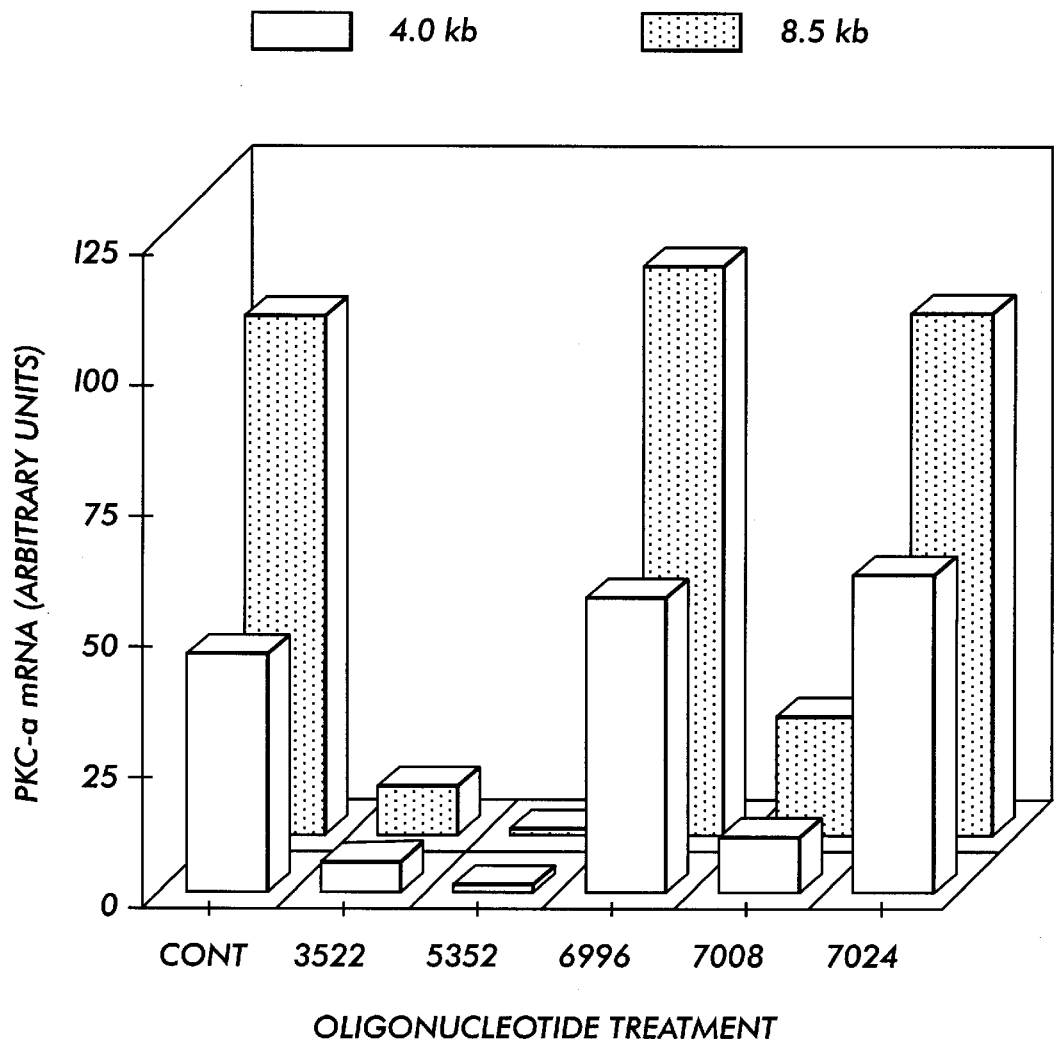
FIG. 3 is a bar graph showing the effects of several 2'-O-methyl chimeric oligonucleotides on PKC-α mRNA levels. Hatched bars represent the 8.5 kb transcript, and plain bars represent the 4.0 kb transcript.

Effect of these oligonucleotides on PKC-α mRNA levels is shown in FIG. 3. Oligonucleotides 7008, 3522 and 5352 show reduction of PKC-α mRNA, with 5352 being most active.

A series of 2'-O-propyl chimeric oligonucleotides was synthesized having SEQ ID NO:4. These oligonucleotides are shown in Table 8.

TABLE 8

Chimeric 2'-O-propyl/deoxy P=S oligonucleotides
bold = 2'-O-propyl; s = P=S linkage, o = P=O linkage

| OLIGO | SEQUENCE | SEQ ID NO. |
|---|---|---|
| 7199 | AsAsAsAsCsGsTsCsAsGsCsCsAsTsGsGsTsCsC | 4 |
| 7273 | AoAoAoAoCoGsTsCsAsGsCsCsAsTsGoGoToCoCoC | 4 |
| 7294 | AsAoAoAoCoGsTsCsAsGsCsCsAsTsGoGoToCoCsC | 4 |
| 7295 | AsAoAoAoCoGsToCsAoGsCoCsAsTsGoGoToCoCsC | 4 |

Figure 4:
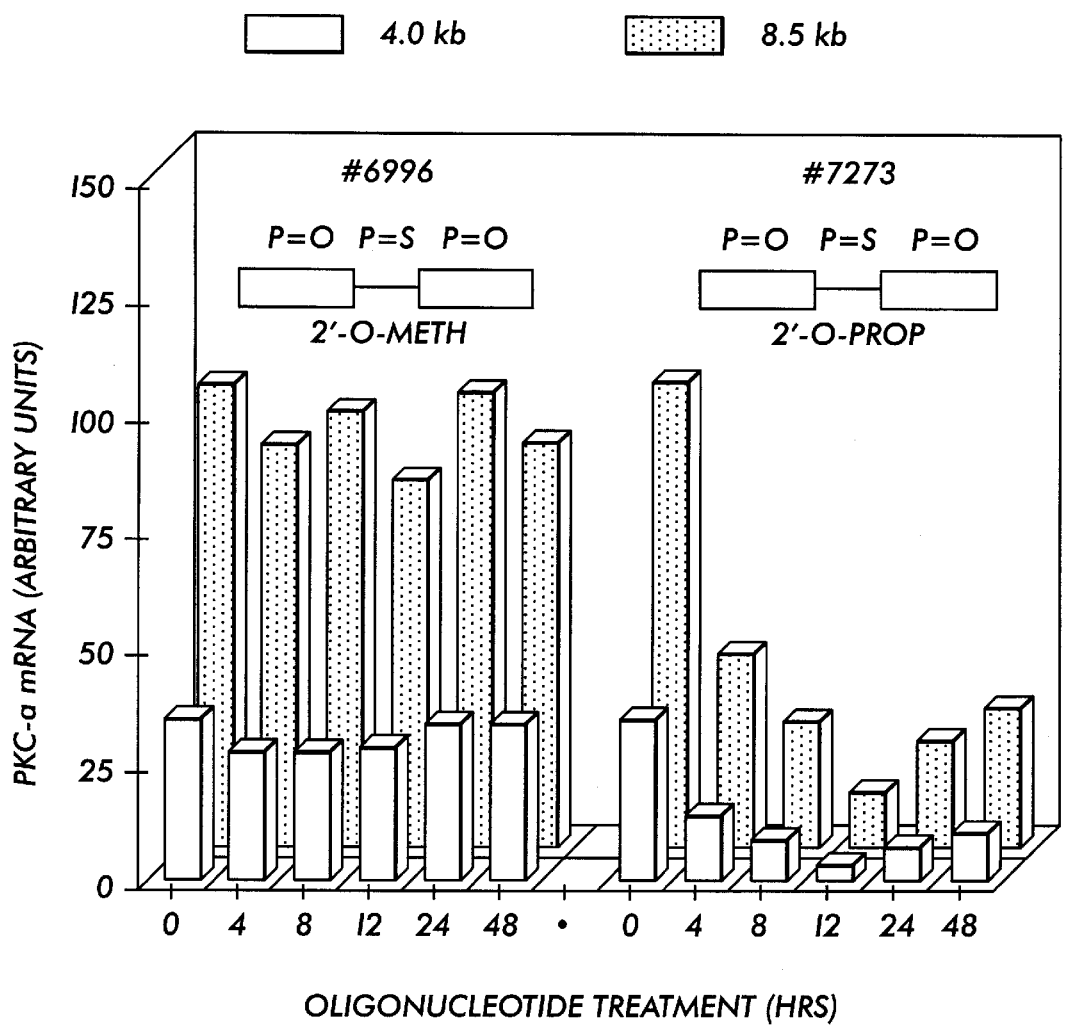
FIG. 4 is a bar graph showing the effects of several 2'-O-methyl and 2'-O-propyl chimeric oligonucleotides on PKC-α mRNA levels. Hatched bars represent the 8.5 kb transcript, and plain bars represent the 4.0 kb transcript.
Figure 5:
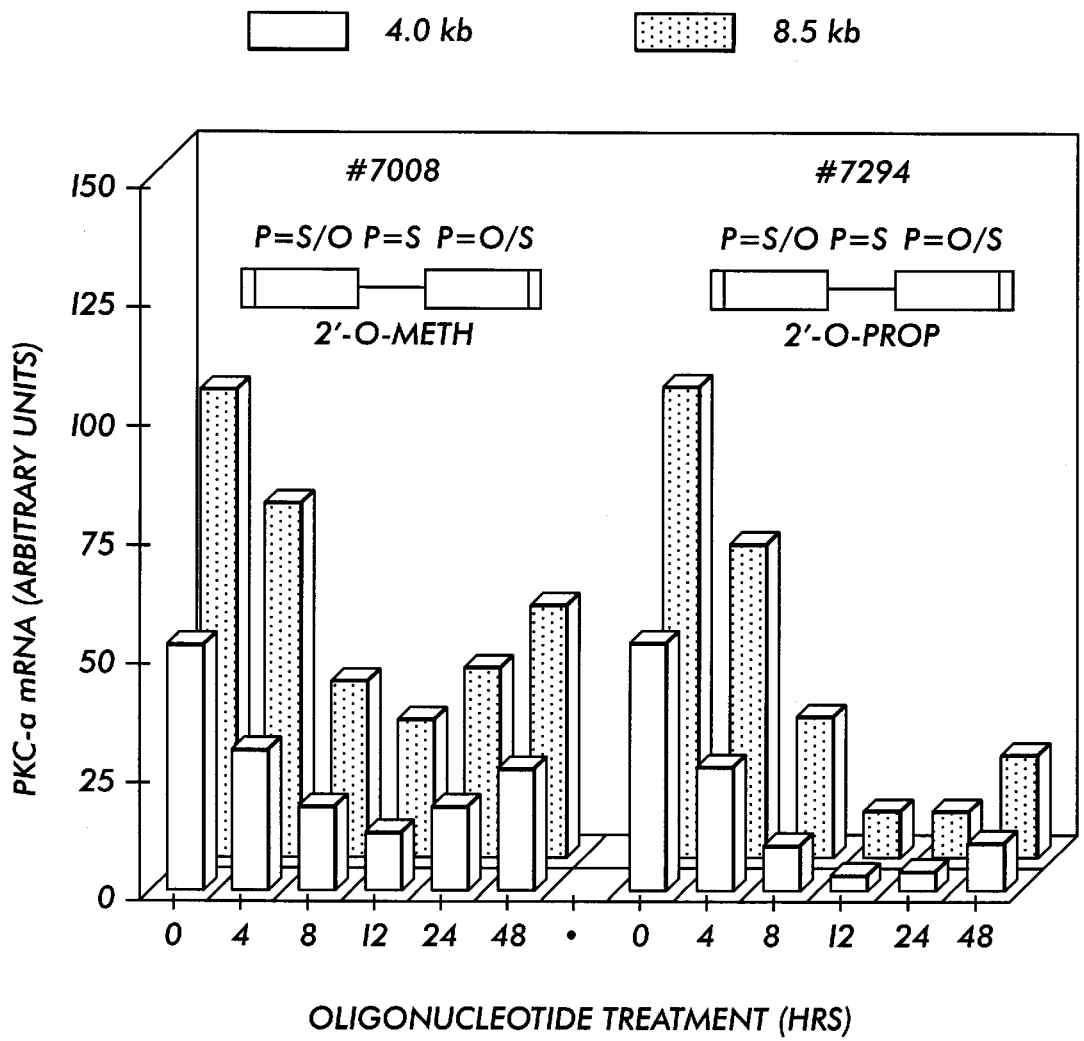
FIG. 5 is a bar graph showing the effects of additional 2'-O-methyl and 2'-O-propyl chimeric oligonucleotides on PKC-α mRNA levels. Hatched bars represent the 8.5 kb transcript, and plain bars represent the 4.0 kb transcript.

These 2'-O-propyl chimeric oligonucleotides were compared to the 2'-O-methyl chimeric oligonucleotides. Oligonucleotides 7273 and 7294 were more active than their 2'-O-methyl counterparts at lowering PKC-α mRNA levels. This is shown in FIGS. 4 and 5.

EXAMPLE 30

Additional Oligonucleotides Which Decrease PKC-α mRNA Expression

Additional phosphorothioate oligonucleotides targeted to the human PKC-α 3' untranslated region were designed and synthesized. These sequences are shown in Table 9.

TABLE 9

Chimeric 2'-O-propyl/deoxy P=S oligonucleotides
targeted to PKC-α 3'-UTR
bold = 2'-O-propyl; s = P=S linkage, o = P=O linkage

| OLIGO | SEQUENCE | | | | | | SEQ ID NO: |
|---|---|---|---|---|---|---|---|
| 6632 | TsTsCs | TsCsGs | CsTsGs | GsTsGs | AsGsTs | TsTsC | 5 |
| 6653 | TsTsCs | TsCsGs | CsTsGs | GsTsGs | AsGsTs | TsTsC | 5 |
| 6665 | ToToCo | TsCsGs | CsTsGs | GsTsGs | AsGsTo | ToToC | 5 |
| 7082 | TsCsTs | CsGsCs | TsGsGs | TsGsAs | GsTsTs | TsC | 6 |
| 7083 | TsCsTs | CsGsCs | TsGsGs | TsGsAs | GsTsTs | TsC | 6 |
| 7084 | ToCoTo | CsGsCs | TsGsGs | TsGsAs | GsToTo | ToC | 6 |

Oligonucleotides 6632, 6653, 7082 and 7083 are most active in reducing PKC-α mRNA levels.

EXAMPLE 31

Inhibition of c-raf Expression by Chimeric Oligonucleotides

Chimeric oligonucleotides having SEQ ID NO:7 were designed using the Genbank c-raf sequence HUMRAFR (Genbank listing x03484), synthesized and tested for inhibition of c-raf mRNA expression in T24 bladder carcinoma cells using a Northern blot assay. These chimeric oligonucleotides have central "gap" regions of 6, 8 or 10 deoxynucleotides flanked by two regions of 2'-O-methyl modified nucleotides, and are shown in Table 10. Backbones were uniformly phosphorothioate. In a Northern blot analysis, as described in Example 32, all three of these oligonucleotides (ISIS 6720, 6-deoxy gap; ISIS 6717, 8-deoxy gap; ISIS 6729, 10-deoxy gap) showed greater than 70% inhibition of c-raf mRNA expression in T24 cells. These oligonucleotides are preferred. The 8-deoxy gap compound (6717) showed greater than 90% inhibition and is more preferred.

TABLE 10

Chimeric 2'-O-methyl P=S deoxy "gap" oligonucleotides
bold = 2'-O-methyl

| OLIGO | SEQUENCE | Target site | SEQ ID NO: |
|---|---|---|---|
| 6720 | TCCCGCCTGTGACATGCATT | 3'UTR | 7 |
| 6717 | TCCCGCCTGTGACATGCATT | 3'UTR | 7 |
| 6729 | TCCCGCCTGTGACATGCATT | 3'UTR | 7 |

Additional chimeric oligonucleotides were synthesized having one or more regions of 2'-O-methyl modification and uniform phosphorothioate backbones. These are shown in Table 11. All are phosphorothioates; bold regions indicate 2'-O-methyl modified regions.

TABLE 11

Chimeric 2'-O-methyl P=S c-raf oligonucleotides

| OLIGO | SEQUENCE | Target site | SEQ ID NO: |
|---|---|---|---|
| 7848 | TCCTCCTCCCCGCGGCGGGT | 5'UTR | 8 |
| 7852 | TCCTCCTCCCCGCGGCGGGT | 5'UTR | 8 |
| 7849 | CTCGCCCGCTCCTCCTCCCC | 5'UTR | 9 |
| 7851 | CTCGCCCGCTCCTCCTCCCC | 5'UTR | 9 |
| 7856 | TTCTCGCCCGCTCCTCCTCC | 5'UTR | 10 |
| 7855 | TTCTCGCCCGCTCCTCCTCC | 5'UTR | 10 |
| 7854 | TTCTCCTCCTCCCCTGGCAG | 3'UTR | 11 |
| 7847 | CTGGCTTCTCCTCCTCCCCT | 3'UTR | 12 |
| 7850 | CTGGCTTCTCCTCCTCCCCT | 3'UTR | 12 |
| 7853 | CCTGCTGGCTTCTCCTCCTC | 3'UTR | 13 |

When tested for their ability to inhibit c-raf mRNA by Northern blot analysis, ISIS 7848, 7849, 7851, 7856, 7855, 7854, 7847, and 7853 gave better than 70% inhibition and are therefore preferred. Of these, 7851, 7855, 7847 and 7853 gave greater than 90% inhibition and are more preferred.

Additional chimeric oligonucleotides with various 2' modifications were prepared and tested. These are shown in Table 12. All are phosphorothioates; bold regions indicate 2'-modified regions.

Of these, oligonucleotides 6720, 6717, 6729, 9720 and 9058 are preferred. Oligonucleotides 6717, 6729, 9720 and 9058 are more preferred.

EXAMPLE 32

Northern Blot Analysis of Inhibition of c-raf mRNA Expression

The human urinary bladder cancer cell line T24 was obtained from the American Type Culture Collection (Rockville, Md.). Cells were grown in McCoy's 5A medium with L-glutamine (GIBCO-BRL, Gaithersburg, Md.), supplemented with 10% heat-inactivated fetal calf serum and 50 U/ml each of penicillin and streptomycin. Cells were seeded on 100 mm plates. When they reached 70% confluency, they were treated with oligonucleotide. Plates were washed with 10 ml prewarmed PBS and 5 ml of OptiMEM reduced-serum medium containing 2.5 μl DOTMA. Oligonucleotide with lipofectin was then added to the desired concentration. After 4 hours of treatment, the medium was replaced with McCoy's medium. Cells were harvested 24 to 72 hours after oligonucleotide treatment and RNA was isolated using a standard CsCl purification method. [Kingston in *Current Protocols in Molecular Biology*, F. M. Ausubel, R. Brent, R. E. Kingston, D. D. Moore, J. A. Smith, J. G. Seidman and K. Strahl, Eds., John Wiley and Sons, New York.] Total RNA was isolated by centrifugation of cell lysates over a CsCl cushion. RNA samples were electrophoresed through 1.2% agarose-formaldehyde gels and transferred to hybridization membranes by capillary diffusion over a 12–14 hour period. The RNA was cross-linked to the membrane by exposure to UV light in a Stratalinker (Stratagene, La Jolla, Calif.) and hybridized to random-primed $^{32}$P-labeled c-raf cDNA probe (obtained from ATCC) or G3PDH probe as a control. RNA was quantitated using a Phosphorimager (Molecular Dynamics, Sunnyvale, Calif.).

EXAMPLE 33

Oligonucleotide Inhibition of Rev Gene Expression

The chimeric oligonucleotides used in this assay are shown in Table 13 below.

TABLE 12

Chimeric 2'-modified P=S c-raf oligonucleotides

| OLIGO | SEQUENCE | TARGET SITE | MODIFIC. | SEQ ID NO: |
|---|---|---|---|---|
| 6720 | TCCCGCCTGTGACATGCATT | 3'UTR | 2'-O—Me | 7 |
| 6717 | TCCCGCCTGTGACATGCATT | 3'UTR | 2'-O—Me | 7 |
| 6729 | TCCCGCCTGTGACATGCATT | 3'UTR | 2'-O—Me | 7 |
| 8097 | TCTGGCGCTGCACCACTCTC | 3'UTR | 2'-O—Me | 14 |
| 9270 | TCCCGCCTGTGACATGCATT | 3'UTR | 2'-O—Pr | 7 |
| 9058 | TCCCGCCTGTGACATGCATT | 3'UTR | 2'-F | 7 |
| 9057 | TCTGGCGCTGCACCACTCTC | 3'UTR | 2'-F | 14 |

TABLE 13

Chimeric 2'-O-propyl/deoxy P=S oligonucleotides
targeted to HIV rev gene
bold = 2'-O-propyl; s = P=S linkage; o = P=O linkage

| OLIGO | SEQUENCE | SEQ ID NO: |
|---|---|---|
| 8907 | UoAoGoGoAoGoAsUsGsCsCsUsAsAoGoGoCoUoUoU | 15 |
| 8908 | GoCoUoAoUoGoUsCsGsAsCsAsCsCoCoAoAoUoUoC | 16 |
| 8909 | CoAoUoAoGoGoAsGsAsUsGsCsCsUoAoAoGoGoCoT | 17 |

Transfection and Luciferase assay: 3T3 cells were maintained in DMEM with glucose, L-glutamine, sodium pyruvate and 10% fetal bovine serum (GIBCO). For all experiments, cells were seeded the previous night at 75,000 cells/well in 6-well plates (Falcon). Transfections were performed using the standard CaPO$_4$ method. For each set of replicates, 15 μg/mL of pSG5/rev plasmid, 18 μg/mL pHIVenu-luc and 2 μg/mL of Rep 6 were precipitated and 200 μL of this was dripped on each well. The precipitate was allowed to incubate on cells for 7 hours at 37° C. The media was then aspirated, the cells washed once with PBS, and fresh complete media added for overnight incubation. Following incubation, the media was removed, cells washed with 2 mL of OPTIMEM (GIBCO) and 1 mL of OPTIMEM containing 2.5 μg/mL of Lipofectin (GIBCO-BRL) and the oligonucleotide added. The mixture was incubated for 4 hours at 37° C., at which point it was aspirated off the cells and complete media was added. Two hours after this treatment, 0.2 μM/mL of dexamethasone (Sigma) was added to all wells to allow induction of the MMTV promoter of pHIVenu-luc.

The Luciferase assay was performed 24 hours later, as follows: The wells were washed twice with PBS and the cells were harvested by scraping in 200 μL of lysis buffer (1% Triton, 25 mM glycylglycine, pH 7.8, 15 mM MgSO$_4$, 4 mM EGTA and 1 mM DTT)> The lysate was clarified by microfuging for 5 minutes at 11,500 rpm in the cold. 100 μL of the lysate was then combined in a microtiter plate with 50 μL of assay buffer (25 mM glycylglycine, pH 7.8, 15 mM MgSO$_4$, 4 mM EGTA, 15 mM potassium phosphate, pH 7.8, 1 mM DTT and 7.5 mM ATP). Luc detection was performed using a microtiter luminescent reader (Dynatech Laboratories). The reactions were started by injecting 50 μL of 1× luciferase solution (Sigma). The 1× solution was diluted in luciferin buffer (25 mM glycylglycine, pH 7.8, 15 mM MgSO$_4$, 4mM EGTA and 4 mM DTT) prior to use from a 10× stock (10 mM luciferin in 10 mM DTT). Samples were counted for 20 seconds. The kinetics of firefly luc light emission are characterized by a flash period lasting a few seconds followed by a period of lower light intensity emission lasting several minutes.

Rev and RRE RNA synthesis: pSG%-Rev contains the Rev gene adjacent to a T7 promoter. BglII linearized pSG5-Rev was used as a DNA template for transcription with T7 RNA polymerase. A template for the production of RRE RNA was produced by PCR. For RNA synthesis, DNA templates were used at 0.2 to 1.0 mg/mL, with 5 mM each of ATP, CTP and GTP, 0.5 mM of UTP, 10 mM of DTT, 40 mM of Tris-HCl, pH 7.5, 6 mM of MgCl$_2$, 4 mM of Spermidine, 500 U/mL of RNAsin at 20 U/μL, 2500 μCi/mL of α $^{32}$P UTP at 10 mCi/mL and 1000 U/mL of T7 RNA polymerase. The reaction was incubated for 1 hour at 37° C. The transcription reaction was terminated by adding formamide loading buffer and was run in a denaturing polyacrylamide gel containing 8M urea. The RNA was eluted from the gel according to the procedure of Schwartz et al. (*Gene*, 1990, 88, 197).

EXAMPLE 34

Immunoassay for Antiviral Screening

NHDF cells were seeded in 96-well culture plates at a density of 15,000 cells/well in serum-free FGM. Established monolayers were pretreated with the oligonucleotide overnight in FGM prior to infection. After pretreatment, cells were rinsed thrice with fresh, prewarmed FGM, and virus in 100 μL of FGM/well was added to achieve an MOI of 0.05 PFU/cell. After 2 hours of incubation at 37° C., virus was removed and fresh medium (100 μL/well) containing the oligonucleotide was added. Medium was exchanged 2 days after infection with fresh medium containing the oligonucleotide, and 6 days after infection, the cells were fixed in absolute ethanol and dried in preparation for antibody staining. A modified protocol was used for some assays in which FGM was supplemented with low levels of FBS (0.2%), and the incubation period after infection was shortened from 6 days to 3 days. The shorter assay eliminated the need to exchange medium 2 days after infection. Both assays yielded comparable values for 50% effective concentrations (EC50s).

Fixed cells were blocked in a solution of PBS containing 2% bovine serum albumin (BSA), and mouse monoclonal antibody (1H10, supplied by Eisai Co., Ltd., Japan) was added in a 1:2000 dilution in PBS-1% BSA. The 1H10 antibody recognizes an abundant late HCMV polypeptide approximately 65 kDa in size. Detection of bound monoclonal antibody was facilitated with biotinylated goat anti-mouse immunoglobulin G abd streptavidin-coupled β-galactosidase (GIBCO-BRL, Gaithersburg, Md.). Chlorophenol red β-D-galactopyranoside was used as a substrate for β-galactosidase, and activity was determined by measuring the optical density at 575 nm of individual wells with a BioTex model EL312e microplate reader.

The oligonucleotides used in this assay are shown in Table 14 below.

TABLE 14

Inhibition of CMV replication by
chimeric 2'-O-methyl P=S oligonucleotides
bold = 2'-O-methyl

| OLIGO | SEQUENCE | SEQ ID NO: |
|---|---|---|
| 4325 | GCG UUT GCT CTT CTT CUU GCG | 18 |
| 4326 | GCG UUU GCT CTT CTU CUU GCG | 19 |

EXAMPLE 35

Diagnostic Assay for the Detection of mRNA overexpression

Oligonucleotides are radiolabeled after synthesis by 32P labeling at the 5' end with polynucleotide kinase. Sambrook et al. [*"Molecular Cloning. A Laboratory Manual,"* Cold Spring Harbor Laboratory Press, 1989, Volume 2, pg. 11.31–11.32]. Radiolabeled oligonucleotide is contacted with tissue or cell samples suspected of mRNA overexpression, such as a sample from a patient, under conditions in which specific hybridization can occur, and the sample is washed to remove unbound oligonucleotide. A similar control is maintained wherein the radiolabeled. oligonucleotide is contacted with normal cell or tissue sample under conditions that allow specific hybridization, and the sample is washed to remove unbound oligonucleotide. Radioactivity remaining in the sample indicates bound oligonucleotide and is quantitated using a scintillation counter or other routine means. Comparison of the radioactivity remaining in the samples from normal and diseased cells indicates overexpression of the mRNA of interest.

Radiolabeled oligonucleotides of the invention are also useful in autoradiography. Tissue sections are treated with radiolabeled oligonucleotide and washed as described above, then exposed to photographic emulsion according to standard autoradiography procedures. A control with normal cell or tissue sample is also maintained. The emulsion, when developed, yields an image of silver grains over the regions overexpressing the mRNA, which is quantitated. The extent of mRNA overexpression is determined by comparison of the silver grains observed with normal and diseased cells.

Analogous assays for fluorescent detection of mRNA expression use oligonucleotides of the invention which are labeled with fluorescein or other fluorescent tags. Labeled DNA oligonucleotides are synthesized on an automated DNA synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling, Va.). Incubation of oligonucleotide and biological sample is carried out as described for radiolabeled oligonucleotides except that instead of a scintillation counter, a fluorescence microscope is used to detect the fluorescence. Comparison of the fluorescence observed in samples from normal and diseased cells enables detection of mRNA overexpression.

EXAMPLE 36

Detection of Abnormal mRNA Expression

Tissue or cell samples suspected of expressing abnormal mRNA are incubated with a first $^{32}P$ or fluorescein-labeled oligonucleotide which is targeted to the wild-type (normal) mRNA. An identical sample of cells or tissues is incubated with a second labeled oligonucleotide which is targeted to the abnormal mRNA, under conditions in which specific hybridization can occur, and the sample is washed to remove unbound oligonucleotide. Label remaining in the sample indicates bound oligonucleotide and can be quantitated using a scintillation counter, fluorimeter, or other routine means. The presence of abnormal mRNA is indicated if binding is observed in the case of the second but not the first sample.

Double labeling can also be used with the oligonucleotides and methods of the invention to specifically detect expression of abnormal mRNA. A single tissue sample is incubated with a first $^{32}P$-labeled oligonucleotide which is targeted to wild-type mRNA, and a second fluorescein-labeled oligonucleotide which is targeted to the abnormal mRNA, under conditions in which specific hybridization can occur. The sample is washed to remove unbound oligonucleotide and the labels are detected by scintillation counting and fluorimetry. The presence of abnormal mRNA is indicated if the sample does not bind the $^{32}P$-labeled oligonucleotide (i.e., is not radioactive) but does retain the fluorescent label (i.e., is fluorescent).

EXAMPLE 37

Plasma uptake and tissue distribution of oligonucleotides in mice

The following oligonucleotides were prepared:

UsGsCsAsTsCsCsCsCsCsAsGsGsCsCsAsCsCsAsT, SEQ ID NO:20

UsGsCsAsTsCsCsCsAsGsGsCsCsAsCsCsAsT, SEQ ID NO:20

UsGsCsAsTsCsCCCCAGGCsCsAsCsCsAsT, SEQ ID NO:20 wherein bold type indicated a 2'-O-propyl substituent, "s" indicates a phosphorothioate linkage and the absence of "s" indicates a phosphodiester linkage in the respective oligonucleotides. The first oligonucleotide is identified as Isis 3082, the second as Isis 9045 and the third as Isis 9046 in the FIGS. 6, 7, 8 and 9. The oligonucleotides were tritiated as per the procedure of Graham et al., *Nuc. Acids Res.*, 1993, 16, 3737–3743.

Animals and Experimental Procedure

For each oligonucleotide studied, twenty male Balb/c mice (Charles River), weighing about 25 gm, were randomly assigned into one of four treatment groups. Following a one-week acclimation, mice received a single tail vein injection of $^3$H-radiolabeled oligonucleotide (approximately 750 nmoles/kg; ranging from 124–170 µCi/kg) administered in phosphate buffered saline, pH 7.0. The concentration of oligonucleotide in the dosing solution was approximately 60 µM. One retro-orbital bleed (at either 0.25, 0.5, 2, or 4 hours post-dose) and a terminal bleed (either 1, 3, 8 or 24 hours post-dose) was collected from each group. The terminal bleed was collected by cardiac puncture following ketamine/xylazine anesthesia. An aliquot of each blood sample was reserved for radioactivity determination and the remaining blood was transferred to an EDTA-coated collection tube and centrifuged to obtain plasma. Urine and feces were collected at intervals (0–4, 4–8 and 8–24 hours) from the group terminated at 24 hours.

At termination, the liver, kidneys, spleen, lungs, heart, brain, sample of skeletal muscle, portion of the small intestine, sample of skin, pancreas, bone (both femurs containing marrow) and two lymph nodes were collected from each mouse and weighed. Feces were weighed, then homogenized 1:1 with distilled water using a Brinkmann Polytron homogenizer (Westbury, N.Y.). Plasma, tissues, urine and feces homogenate were divided for the analysis of radioactivity by combustion and for determination of intact oligonucleotide content. All samples were immediately frozen on dry ice after collection and stored at –80° C. until analysis.

Analysis of Radioactivity in Plasma, Tissue, and Excreta

Plasma and urine samples were weighed directly into scintillation vials and analyzed directly by liquid scintillation counting after the addition of 15 ml of BetaBlend (ICN Biomedicals, Costa Mesa, Calif.). All other samples (tissues, blood and homogenized feces) were weighed into combustion boats and oxidized in a Biological Materials Oxidizer (Model OX-100; R. J. Harvey Instrument Corp., Hillsdale, N.J.). The $^3$H$_2$O was collected in 20 ml of cocktail, composed of 15 ml of BetaBlend and 5 ml of Harvey Tritium Cocktail (R. J. Harvey Instrument Corp., Hillsdale, N.J.). The combustion efficiency was determined daily by combustion of samples spiked with a solution of $^3$H-mannitol and ranged between 73.9–88.3%. Liquid scintillation counting was performed using a Beckman LS 9800 or LS 6500 Liquid Scintillation System (Beckman Instruments, Fullerton, Calif.). Samples were counted for 10 minutes with automatic quench correction. Disintergration per minute values were corrected for the efficiency of the combustion process.

Analysis of Data

Radioactivity in samples was expressed as disintergrations per minute per gram of sample. These values were divided by the specific activity of the radiolabel to express the data in nanomole-equivalents of total oligonucleotide per gram of sample, then converted to percent of dose administered per organ or tissue. Assuming a tissue density of 1 gm/ml, the nmole/gram data were converted to a total $\mu M$ concentration. To calculate the concentration of intact oligonucleotide in plasma, liver or kidney at each time point, the mean total $\mu M$ concentrations were divided by the percent of intact oligonucleotide in the dosing solution (82–97%), then multiplied by the mean percentage of intact oligonucleotide at each time point as determined by CGE or HPLC. This data was then used for the calculation of tissue half-lives by linear regression and to compare the plasma pharmacokinetics of the different modified oligonucleotides. The pharmacokinetic parameters were determined using PCNONLIN 4.0 (Statistical Consultants, Inc., Apex, N.C.). After examination of the data, a one-compartment bolus input, first order output model (library model 1) was selected for use.

Figure 6:
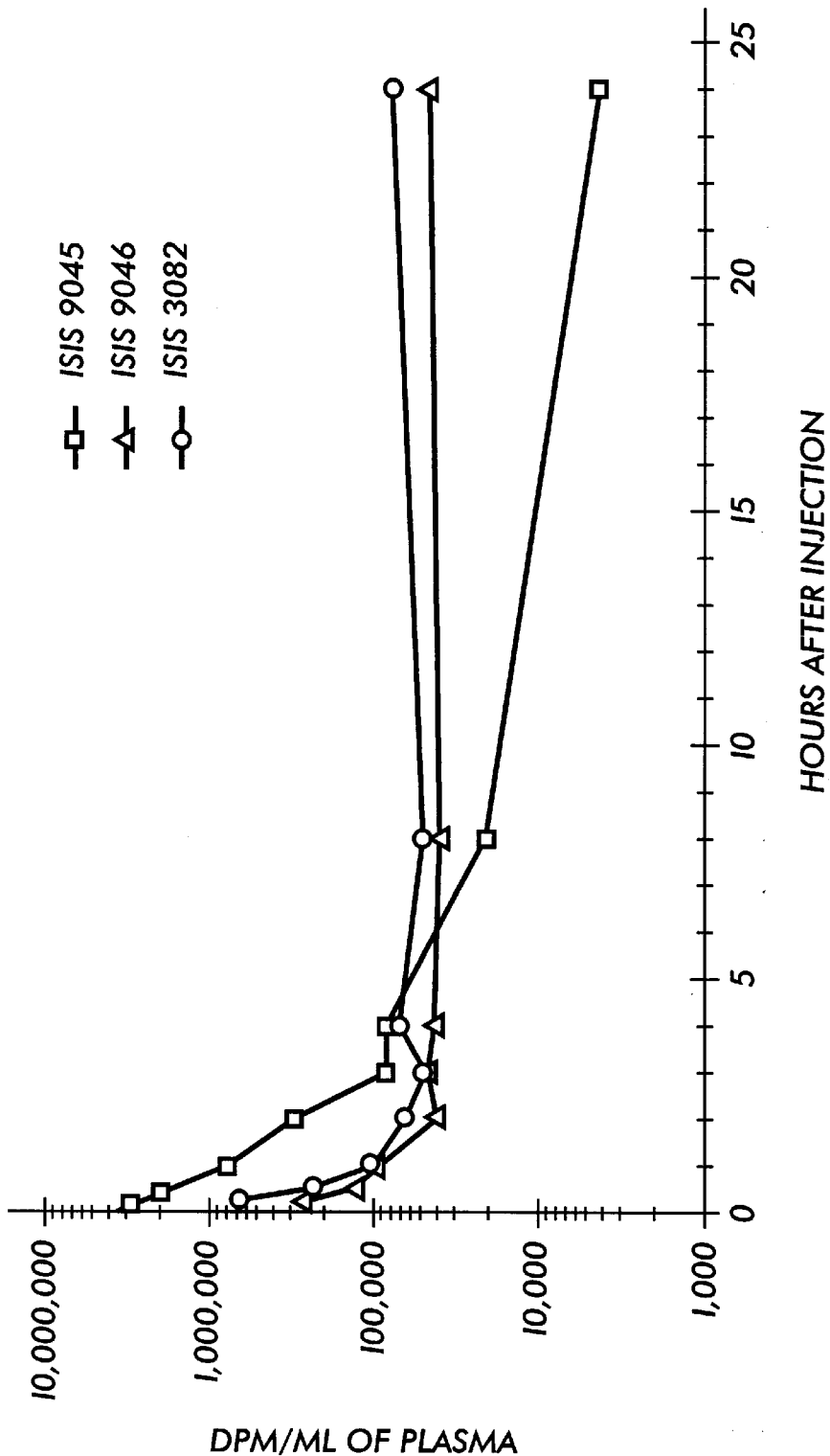
FIG. 6 is a graph showing mouse plasma concentrations of a control compound and two of the compounds of the invention. The plasma concentration is plotted verses time.
Figure 7:
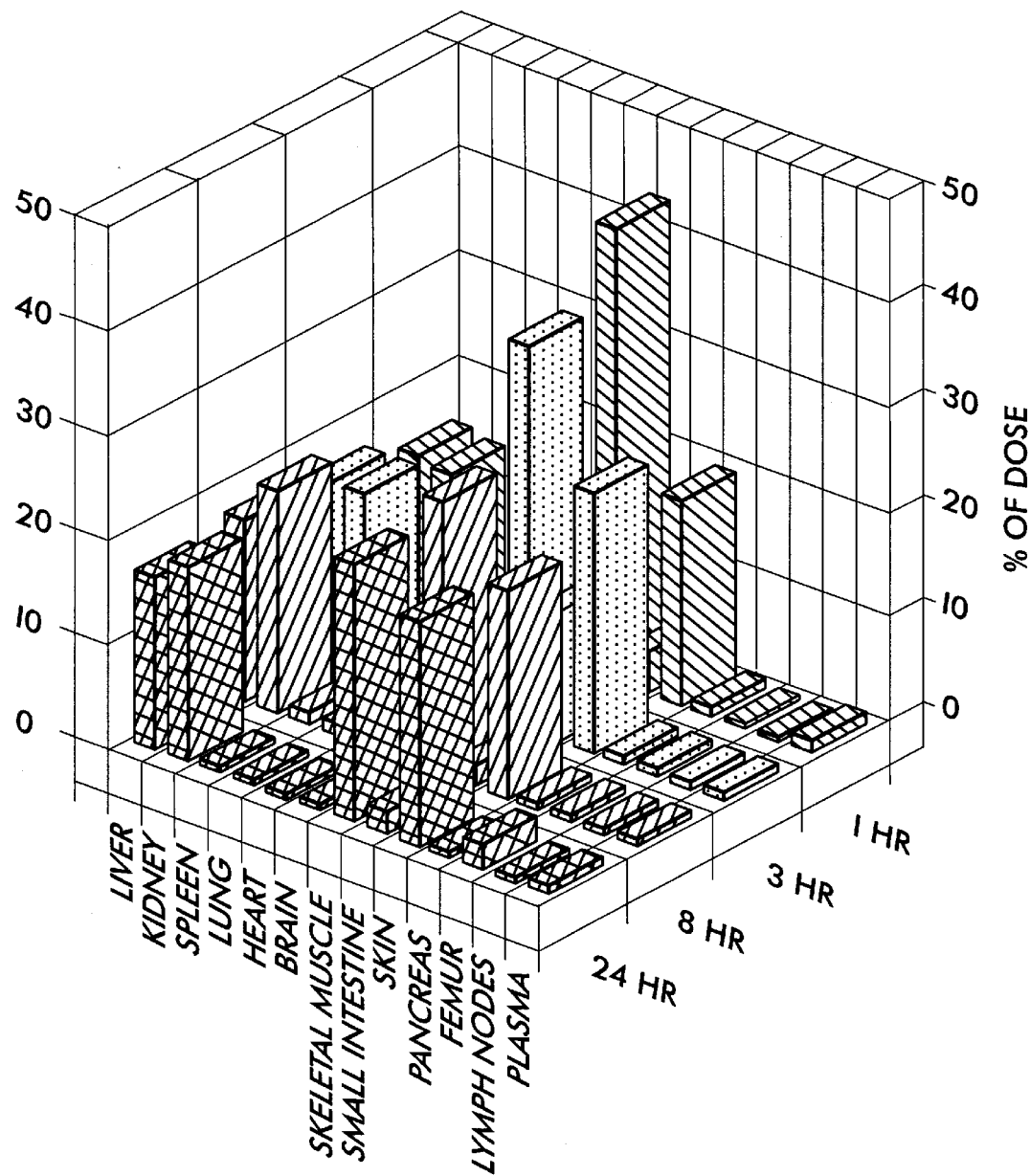
FIG. 7 is a three dimensional graph showing distribution of a control compound among various tissue in the mouse. Specific tissues are shown on one axis, time on a second axis and percent of dose on the third axis. The compound was delivered by intravenous injected.
Figure 8:
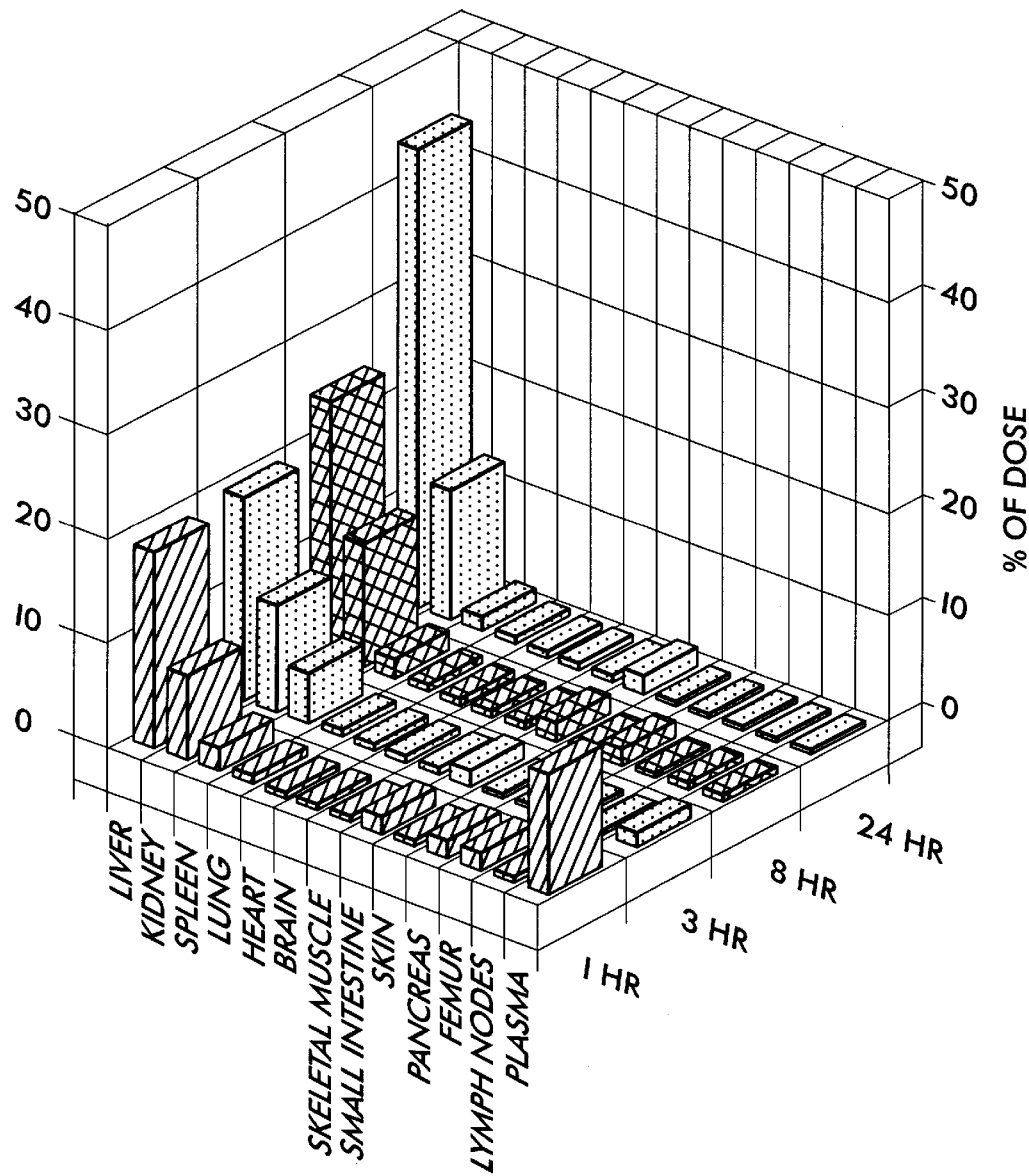
FIG. 8 is a three dimensional graph showing distribution of a compound of the invention among various tissue in the mouse. Specific tissues are shown on one axis, time on a second axis ard percent of dose on the third axis. The compound was delivered by intravenous injected.
Figure 9:
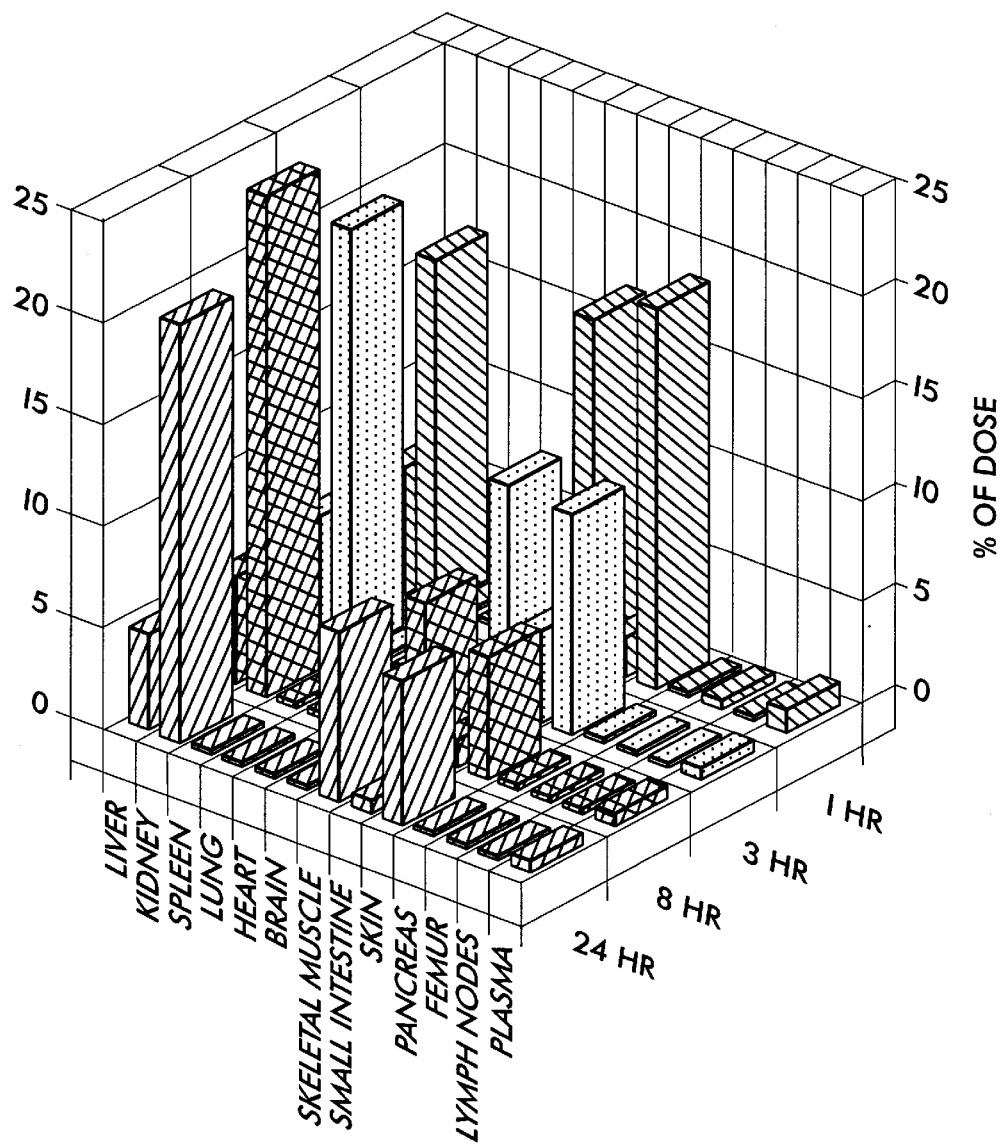
FIG. 9 is a three dimensional graph showing distribution of a further compound of the invention among various tissue in the mouse. Specific tissues are shown on one axis, time on a second axis and percent of dose on the third axis. The compound was delivered by intravenous injected.

The result of the animal plasma uptake and tissue distribution tests are illustrated graphically in FIGS. 6, 7, 8 and 9. As is seen in FIG. 6, plasma concentration of each of the test oligonucleotides decrease from the initial injection levels to lower levels over the twenty-four hour test period. Plasma concentrations of the oligonucleotides of the invention were maintained at levels equivalent to those of the non-conjugate bearing phosphorothioate. All of the test compounds were taken up from the plasma to tissues as is shown in FIGS. 7, 8 and 9. The compounds of the invention had different distribution between the various tissues. FIG. 7 shows the distribution pattern for the control oligonucleotide, identified as ISIS 3082, a phosphorothioate oligonucleotide. FIG. 8 shows the distribution pattern for a first compound of the invention, an oligonucleotide, identified as ISIS 9045, having a 2'-substituent at each nucleotide. FIG. 9 shows the distribution pattern for a further compound of the invention, "gap mer" oligonucleotide, identified as ISIS 9046, having a 2'-substituent and phosphodiester linkages at each nucleotide at "flanking" sections of the oligonucleotide and 2'-deoxy, phosphorothioate nucleotides in a central or gap region.

What is claimed is:

1. A nuclease resistant compound that hybridizes with RNA or DNA, comprising a plurality of covalently-bound nucleosides that individually include a ribose or deoxyribose sugar portion and a base portion, wherein:
   said nucleosides are joined together by internucleoside linkages such that the base portion of said nucleosides form a mixed base sequence that is complementary to a RNA base sequence or to a DNA base sequence; and
   at least one of said nucleosides includes a modified deoxyfuranosyl moiety bearing a 2'-substituent selected from the group consisting of cyano, fluoromethyl, thioalkoxyl, fluoroalkoxyl, alkylsulfinyl, alkylsulfonyl, allyloxy and alkeneoxy.

2. A compound of claim 1 wherein said 2'-substituent is 2'-alkylsulfinyl or alkylsulfonyl.

3. A compound of claim 1 wherein said 2'-substituent is 2'-thioalkoxyl.

4. A compound of claim 3 wherein said 2'-thioalkoxyl is 2'-S-($C_1$–$C_{20}$ alkyl).

5. The compound of claim 1 having 5 to 50 nucleoside linked nucleosides.

6. The compound of claim 1 wherein at least two of said nucleosides are covalently bound through phosphorothioate, methyl phosphonate, or phosphate alkylate internucleoside linkages.

* * * * *

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:1:

CCACACCGAC GGCGCCC 17

( 2 ) INFORMATION FOR SEQ ID NO:2:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:2:

CTTATATTCC GTCATCGCTC 20

( 2 ) INFORMATION FOR SEQ ID NO:3:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:3:

TCCGTCATCG CTCCTCAGGG 20

( 2 ) INFORMATION FOR SEQ ID NO:4:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:4:

AAAACGTCAG CCATGGTCCC 20

( 2 ) INFORMATION FOR SEQ ID NO:5:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:5:

TTCTCGCTGG TGAGTTTC 18

( 2 ) INFORMATION FOR SEQ ID NO:6:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:6:

TCTCGCTGGT GAGTTTC 17

( 2 ) INFORMATION FOR SEQ ID NO:7:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:7:

TCCCGCCTGT GACATGCATT 20

( 2 ) INFORMATION FOR SEQ ID NO:8:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:8:

TCCTCCTCCC CGCGGCGGGT 20

( 2 ) INFORMATION FOR SEQ ID NO:9:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:9:

CTCGCCCGCT CCTCCTCCCC 20

( 2 ) INFORMATION FOR SEQ ID NO:10:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:10:

TTCTCGCCCG CTCCTCCTCC 20

( 2 ) INFORMATION FOR SEQ ID NO:11:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:11:

TTCTCCTCCT CCCCTGGCAG 20

( 2 ) INFORMATION FOR SEQ ID NO:12:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:12:

CTGGCTTCTC CTCCTCCCCT 20

( 2 ) INFORMATION FOR SEQ ID NO:13:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:13:

CCTGCTGGCT TCTCCTCCTC 20

( 2 ) INFORMATION FOR SEQ ID NO:14:

( i ) SEQUENCE CHARACTERISTICS:

(A) LENGTH: 20 bases
(B) TYPE: nucleic acid
(C) STRANDEDNESS: single
(D) TOPOLOGY: linear (iv) ANTI-SENSE: yes (xi) SEQUENCE DESCRIPTION: SEQ ID NO:14:

TCTGGCGCTG CACCACTCTC   20

(2) INFORMATION FOR SEQ ID NO:15:

(i) SEQUENCE CHARACTERISTICS:
(A) LENGTH: 20 bases
(B) TYPE: nucleic acid
(C) STRANDEDNESS: single
(D) TOPOLOGY: linear (iv) ANTI-SENSE: yes (xi) SEQUENCE DESCRIPTION: SEQ ID NO:15:

UAGGAGAUGC CUAAGGCUUU   20

(2) INFORMATION FOR SEQ ID NO:16:

(i) SEQUENCE CHARACTERISTICS:
(A) LENGTH: 20 bases
(B) TYPE: nucleic acid
(C) STRANDEDNESS: single
(D) TOPOLOGY: linear (iv) ANTI-SENSE: yes (xi) SEQUENCE DESCRIPTION: SEQ ID NO:16:

GCUAUGUCGA CACCCAAUUC   20

(2) INFORMATION FOR SEQ ID NO:17:

(i) SEQUENCE CHARACTERISTICS:
(A) LENGTH: 20 bases
(B) TYPE: nucleic acid
(C) STRANDEDNESS: single
(D) TOPOLOGY: linear (iv) ANTI-SENSE: yes (xi) SEQUENCE DESCRIPTION: SEQ ID NO:17:

CAUAGGAGAU GCCUAAGGCT   20

(2) INFORMATION FOR SEQ ID NO:18:

(i) SEQUENCE CHARACTERISTICS:
(A) LENGTH: 21 bases
(B) TYPE: nucleic acid
(C) STRANDEDNESS: single
(D) TOPOLOGY: linear (iv) ANTI-SENSE: yes (xi) SEQUENCE DESCRIPTION: SEQ ID NO:18:

GCGUUTGCTC TTCTTCUUGC G   21

(2) INFORMATION FOR SEQ ID NO:19:

(i) SEQUENCE CHARACTERISTICS:
(A) LENGTH: 21 bases
(B) TYPE: nucleic acid
(C) STRANDEDNESS: single
(D) TOPOLOGY: linear ( i v ) ANTI-SENSE: yes ( x i ) SEQUENCE DESCRIPTION: SEQ ID NO:19:

GCGUUUGCTC TTCTUCUUGC G 21

( 2 ) INFORMATION FOR SEQ ID NO:20:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:20:

UGCATCCCCC AGGCCACCAT 20

( 2 ) INFORMATION FOR SEQ ID NO:21:

( i ) SEQUENCE CHARACTERISTICS:
        ( A ) LENGTH: 15 bases
        ( B ) TYPE: nucleic acid
        ( C ) STRANDEDNESS: single
        ( D ) TOPOLOGY: linear ( x i ) SEQUENCE DESCRIPTION: SEQ ID NO:21:

CGACTATGCA AGTAC 15

( 2 ) INFORMATION FOR SEQ ID NO:22:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( x i ) SEQUENCE DESCRIPTION: SEQ ID NO:22:

CTCGTACCTT CCGGTCC 17

( 2 ) INFORMATION FOR SEQ ID NO:23:

( i ) SEQUENCE CHARACTERISTICS:
        ( A ) LENGTH: 12 bases
        ( B ) TYPE: nucleic acid
        ( C ) STRANDEDNESS: single
        ( D ) TOPOLOGY: linear ( x i ) SEQUENCE DESCRIPTION: SEQ ID NO:23:

GAGCUCCCAG GC 12

( 2 ) INFORMATION FOR SEQ ID NO:24:

( i ) SEQUENCE CHARACTERISTICS:
        ( A ) LENGTH: 15 bases
        ( B ) TYPE: nucleic acid
        ( C ) STRANDEDNESS: single
        ( D ) TOPOLOGY: linear ( x i ) SEQUENCE DESCRIPTION: SEQ ID NO:24:

CGACUAUGCA AGUAC 15

( 2 ) INFORMATION FOR SEQ ID NO:25:

( i ) SEQUENCE CHARACTERISTICS:
        ( A ) LENGTH: 15 bases
        ( B ) TYPE: nucleic acid
        ( C ) STRANDEDNESS: single ( D ) TOPOLOGY: linear ( x i ) SEQUENCE DESCRIPTION: SEQ ID NO:25:

UCCAGGUGUC CGAUC 15

( 2 ) INFORMATION FOR SEQ ID NO:26:

( i ) SEQUENCE CHARACTERISTICS:
        ( A ) LENGTH: 13 bases
        ( B ) TYPE: nucleic acid
        ( C ) STRANDEDNESS: single
        ( D ) TOPOLOGY: linear ( x i ) SEQUENCE DESCRIPTION: SEQ ID NO:26:

TCCAGGCCGU UUC 13

( 2 ) INFORMATION FOR SEQ ID NO:27:

( i ) SEQUENCE CHARACTERISTICS:
        ( A ) LENGTH: 13 bases
        ( B ) TYPE: nucleic acid
        ( C ) STRANDEDNESS: single
        ( D ) TOPOLOGY: linear ( x i ) SEQUENCE DESCRIPTION: SEQ ID NO:27:

TCCAGGTGTC CCC 13

( 2 ) INFORMATION FOR SEQ ID NO:28:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( x i ) SEQUENCE DESCRIPTION: SEQ ID NO:28:

CUCGUACCUU CCGGUCC 17

( 2 ) INFORMATION FOR SEQ ID NO:29:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:29:

CTCGTACCTT TCCGGTCC 18

( 2 ) INFORMATION FOR SEQ ID NO:30:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:30:

GAGCAUGGYA AGGCCAGG 18

( 2 ) INFORMATION FOR SEQ ID NO:31:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:31:

CUCGUACCUU UCCGGUCC 18

( 2 ) INFORMATION FOR SEQ ID NO:32:

( i ) SEQUENCE CHARACTERISTICS:
        ( A ) LENGTH: 16 bases
        ( B ) TYPE: nucleic acid
        ( C ) STRANDEDNESS: single
        ( D ) TOPOLOGY: linear ( x i ) SEQUENCE DESCRIPTION: SEQ ID NO:32:

GCGTTTTTTT TTTGCG 16

( 2 ) INFORMATION FOR SEQ ID NO:33:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( x i ) SEQUENCE DESCRIPTION: SEQ ID NO:33:

CGCAAAAAAA AAAAAACGC 19

( 2 ) INFORMATION FOR SEQ ID NO:34:

( i ) SEQUENCE CHARACTERISTICS:
        ( A ) LENGTH: 47 bases
        ( B ) TYPE: nucleic acid
        ( C ) STRANDEDNESS: single
        ( D ) TOPOLOGY: linear ( x i ) SEQUENCE DESCRIPTION: SEQ ID NO:34:

ACATTATGCT AGCTTTTTGA GTAAACTTGT GGGGCAGGAG ACCCTGT 47

( 2 ) INFORMATION FOR SEQ ID NO:35:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( x i ) SEQUENCE DESCRIPTION: SEQ ID NO:35:

GAGATCTGAA GCTTCTGGAT GGTCAGCGC 29

( 2 ) INFORMATION FOR SEQ ID NO:36:

( i ) SEQUENCE CHARACTERISTICS:
        ( A ) LENGTH: 35 bases
        ( B ) TYPE: nucleic acid
        ( C ) STRANDEDNESS: single
        ( D ) TOPOLOGY: linear ( x i ) SEQUENCE DESCRIPTION: SEQ ID NO:36:

GAGATCTGAA GCTTGAAGAC GCCAAAAACA TAAAG 35

( 2 ) INFORMATION FOR SEQ ID NO:37:

( i ) SEQUENCE CHARACTERISTICS:
    ( A ) LENGTH: 33 bases
    ( B ) TYPE: nucleic acid
    ( C ) STRANDEDNESS: single
    ( D ) TOPOLOGY: linear ( x i ) SEQUENCE DESCRIPTION: SEQ ID NO:37:

ACGCATCTGG CGCGCCGATA CCGTCGACCT CGA    33